United States Patent
Tafesse

(10) Patent No.: US 8,389,549 B2
(45) Date of Patent: Mar. 5, 2013

(54) SUBSTITUTED PYRIDINES USEFUL FOR TREATING PAIN

(75) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 36 days.

(21) Appl. No.: 12/596,997

(22) PCT Filed: Apr. 25, 2008

(86) PCT No.: PCT/US2008/005329
§ 371 (c)(1),
(2), (4) Date: Oct. 22, 2009

(87) PCT Pub. No.: WO2008/133973
PCT Pub. Date: Nov. 6, 2008

(65) Prior Publication Data
US 2010/0130552 A1    May 27, 2010

Related U.S. Application Data

(60) Provisional application No. 60/924,056, filed on Apr. 27, 2007, provisional application No. 60/924,377, filed on May 11, 2007.

(51) Int. Cl.
*A61K 31/44* (2006.01)

(52) U.S. Cl. ................... 514/340; 546/268.1
(58) Field of Classification Search ............ 514/340; 546/268.1
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,797,419 A | 1/1989 | Moos et al. | |
| 5,039,680 A | 8/1991 | Imperato et al. | |
| 5,059,595 A | 10/1991 | Le Grazie | |
| 5,073,543 A | 12/1991 | Marshall et al. | |
| 5,075,341 A | 12/1991 | Mendelson et al. | |
| 5,120,548 A | 6/1992 | McClelland et al. | |
| 5,198,459 A | 3/1993 | Imperato et al. | |
| 5,232,934 A | 8/1993 | Downs | |
| 5,354,556 A | 10/1994 | Sparks et al. | |
| 5,399,574 A | 3/1995 | Robertson et al. | |
| 5,442,064 A | 8/1995 | Pieper et al. | |
| 5,474,996 A | 12/1995 | Caille et al. | |
| 5,529,998 A | 6/1996 | Häbich et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 5,762,925 A | 6/1998 | Sagen | |
| 5,891,889 A | 4/1999 | Anthony et al. | |
| 6,063,930 A | 5/2000 | Dinsmore et al. | |
| 6,136,839 A | 10/2000 | Isakson et al. | |
| 6,150,129 A | 11/2000 | Cook et al. | |
| 6,166,038 A | 12/2000 | Fukami et al. | |
| 6,204,284 B1 | 3/2001 | Beer et al. | |
| 6,239,267 B1 | 5/2001 | Duckworth et al. | |
| 6,248,756 B1 | 6/2001 | Anthony et al. | |
| 6,335,180 B1 | 1/2002 | Julius et al. | |
| 6,406,908 B1 | 6/2002 | McIntyre et al. | |
| 6,482,479 B1 | 11/2002 | Dubal et al. | |
| 6,635,657 B1 | 10/2003 | Beight et al. | |
| 6,689,780 B1 | 2/2004 | Beight et al. | |
| 6,703,362 B1 | 3/2004 | Alvarez et al. | |
| 7,129,235 B2 | 10/2006 | Zheng et al. | |

(Continued)

FOREIGN PATENT DOCUMENTS

DE    199 34 799 A1    2/2001
EP    1 939 189 A1    7/2008

(Continued)

OTHER PUBLICATIONS

Badham, N., et al., "A Practical Synthesis of the PDE4 Inhibitor, SB-207499, from a Cyclohexanone Precursor," *Org. Proc. Res. Dev.* 7:101-108, American Chemical Society, United States (2003).

(Continued)

*Primary Examiner* — Douglas M Willis
(74) *Attorney, Agent, or Firm* — Sterne, Kessler, Goldstein & Fox, P.L.L.C.

(57) ABSTRACT

A compound of Formula: (I) or a pharmaceutically acceptable derivative thereof, where $Ar_1$, $Ar_2$, X, $R_3$, and m are as disclosed herein. Compounds of Formulae (I)-(V) and pharmaceutically acceptable derivatives thereof; compositions comprising an effective amount of a compound of Formulae (I)-(V) or a pharmaceutically acceptable derivative thereof; and methods for treating or preventing pain, UI, an ulcer, IBD, or IBS in an animal comprising administering to an animal in need thereof an effective amount of a compound of Formulae (I)-(V) or a pharmaceutically acceptable derivative thereof are disclosed herein.

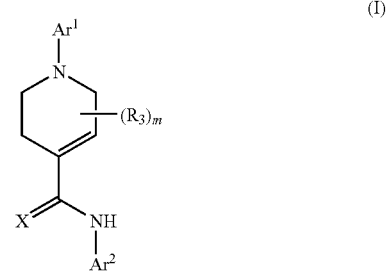

(I)

30 Claims, No Drawings

U.S. PATENT DOCUMENTS

| | | | |
|---|---|---|---|
| 7,348,343 | B2 | 3/2008 | Zheng et al. |
| 7,572,815 | B2 | 8/2009 | Nakagawa et al. |
| 7,683,063 | B2 | 3/2010 | Kyle et al. |
| 2002/0091116 | A1 | 7/2002 | Zhu et al. |
| 2003/0087917 | A1 | 5/2003 | Strack et al. |
| 2004/0044003 | A1 | 3/2004 | Kyle et al. |
| 2004/0077628 | A1 | 4/2004 | Ishihara et al. |
| 2004/0152690 | A1 | 8/2004 | Balan et al. |
| 2004/0186111 | A1 | 9/2004 | Sun et al. |
| 2004/0259931 | A1 | 12/2004 | Goodfellow et al. |
| 2005/0009841 | A1 | 1/2005 | Zheng et al. |
| 2006/0128717 | A1 | 6/2006 | Sun et al. |
| 2006/0128775 | A1 | 6/2006 | Patel et al. |
| 2006/0199824 | A1 | 9/2006 | Sun et al. |
| 2008/0153809 | A1 | 6/2008 | Lee et al. |
| 2009/0062261 | A1 | 3/2009 | Masui et al. |
| 2009/0258900 | A1 | 10/2009 | Nakagawa et al. |

FOREIGN PATENT DOCUMENTS

| | | | |
|---|---|---|---|
| JP | 62-089679 | A | 4/1987 |
| JP | 11-199573 | A | 7/1999 |
| JP | 2003-142681 | | 5/2003 |
| JP | 2003-192673 | A | 7/2003 |
| WO | WO 97/28140 | A1 | 8/1997 |
| WO | WO 97/38665 | A2 | 10/1997 |
| WO | WO 98/31669 | A1 | 7/1998 |
| WO | WO 98/31677 | A1 | 7/1998 |
| WO | WO 99/37304 | A1 | 7/1999 |
| WO | WO 00/59510 | A1 | 10/2000 |
| WO | WO 01/27107 | A2 | 4/2001 |
| WO | WO 01/57008 | A1 | 8/2001 |
| WO | WO 02/02549 | | 1/2002 |
| WO | WO 02/08221 | A2 | 1/2002 |
| WO | WO 03/066595 | A2 | 8/2003 |
| WO | WO 03/068749 | A1 | 8/2003 |
| WO | WO 2004/058754 | A1 | 7/2004 |
| WO | WO 2004/089286 | A2 | 10/2004 |
| WO | WO 2004/103954 | A1 | 12/2004 |
| WO | WO 2005/004866 | A1 | 1/2005 |
| WO | WO 2005/009987 | A1 | 2/2005 |
| WO | WO 2005/009988 | A1 | 2/2005 |

OTHER PUBLICATIONS

Barthó, L., et al., "Involvement of Capsaicin-sensitive Neurones in Hyperalgesia and Enhanced Opioid Antinociception in Inflammation," *Naunyn-Schmiedeberg's Archives of Pharmacol. 342*:666-670, Springer-Verlag, Netherlands (1990).

Berkow, R., et al., "Crohn's Disease," in The Merck Manual of Medical Information, R. Berkow ed., pp. 528-530, Merck Research Laboratories, Whitehouse Station, N.J., United States (1997).

Berkow, R., et al., "Irritable Bowel Syndrome," in The Merck Manual of Medical Information, R. Berkow ed., pp. 525-526, Merck Research Laboratories, Whitehouse Station, N.J., United States (1997).

Berkow, R., et al., eds, "Peptic Ulcer," The Merck Manual of Medical Information, Home Edition, pp. 496-500, Merck Research Laboratories, Whitehouse Station, N.J., United States (1997).

Berkow, R., et al., eds, "Seizure Disorder," The Merck Manual of Medical Information, Home Edition, pp. 345-350, Merck Research Laboratories, Whitehouse Station, N.J., United States (1997).

Berkow, R., et al., eds, "Stroke," The Merck Manual of Medical Information, Home Edition, pp. 352-355, Merck Research Laboratories, Whitehouse Station, N.J., United States (1997).

Berkow, R., et al., eds, "Ulcerative Colitis," The Merck Manual of Medical Information, Home Edition, pp. 530-532, Merck Research Laboratories, Whitehouse Station, N.J., United States (1997).

Berkow, R., et al., eds, "Urinary Incontinence," The Merck Manual of Medical Information, Home Edition, pp. 631-634, Merck Research Laboratories, Whitehouse Station, N.J., United States (1997).

Brunton, L., "Agents for Control of Gastric Acidity and Treatment of Peptic Ulcers," in Goodman and Gilman's The Pharmacological Basis of Therapeutics, 9th Edition, pp. 901-915, J. Hardman, et al., eds., New York: McGraw-Hill, United States (1996).

Buchwald, C., et al., "Observer variations in the evaluation of facial nerve function after acoustic neuroma surgery," *J. Laryngol. Otol. 107*:1119-1121, Cambridge University Press, United Kingdom (1993).

Buchwald, H., et al., "Long-term, continuous intravenousd heparin administration by an implantable infusion pump in ambulatory patients with recurrent venous thrombosis," *Surgery 88*:507-516, The C.V. Mosby Co., United States (1980).

Bundgaard, H., et al., "(C)Means to Enhance Penetrations: (1) Prodrugs as a means to improve the delivery of peptide drugs," *Adv. Drug Delivery Revs. 8*:1-38, Elsevier Science Publishers B.V., Netherlands (1992).

Bundgaard, H., "Design and Application of Prodrugs," Chapter 5 in *A Textbook of Drug Design and Development*, P. Krogsgaard-Larsen and H. Bundgaard, eds. pp. 113-191, Harwood Academic Publishers, Netherlands (1991).

Chiamulera, C., et al., "Reinforcing and locomotor stimulant effects of cocaine are absent in mGluR5 null mutant mice," *Nat. Neurosci. 4*:873-884, Nature Publishing Group, United States (2001).

Chu-Moyer, M., et al., "Orally-effective, Long-Acting Sorbitol Dehydrogenase Inhibitors: Synthesis, Structure-Activity Relationships, and in Vivo Evaluations of Novel Heterocycle-Substituted Piperazino-Pyrimidines," *J. Med. Chem. 45*:511-528, American Chemical Society, United States (2002).

Cooke, R., "Glycopyrrolate in bladder dysfunction," *S. Afr. Med J. 63*:3, South African Medical Association, South Africa (1983).

Cope, A. and Schmitz, W., "Cyclic Polyolefins, VII. Structure of the Eight-membered Cyclic Dimer of Chloroprene," *J. Am. Chem. Soc. 72*:3056-3062, American Chemical Society, United States (1950).

Cope, A. and Brown, M., "Proximity Effects. XV. The Reaction of Phenylmagnesium Bromide with Methyl Cyclooctene-1-carboxylate," *J. Am. Chem. Soc. 80*:2859-2864, American Chemical Society, United States (1958).

D'Amour, F. and Smith, D., "A Method for Determining Loss of Pain Sensation," *J. Pharmacol. Exp. Ther. 72*:74-79, American Society for Pharmacology and Experimental Therapeutics, United States (1941).

Di Marzo, V., et al., "Endovanilloid signaling in pain," *Curr. Opin. Neurobiol. 12*:372-389, Current Biology, England (2002).

Dogrul, A., et al., "Peripheral and spinal antihyperalgesic activity of SIB-1757, a metabotropic glutamate receptor (mGLUR$_5$) antagonist, in experimental neuropathic pain in rats," *Neurosci. Lett. 292*:115-118, Elsevier Science Ireland Ltd., Ireland (2000).

During, M., et al., "Controlled release of dopamine from a polymeric brain implant: in vivo characterization," *Ann. Neurol. 25*:351-356, American Neurological Association, United States (1989).

Foley, K., "Pain," in *Cecil Textbook of Medicine*, 20th Edition, pp. 100-107, Plum, F., et al., eds., W. B. Saunders Company, United States (1996).

Fundytus, M., "Glutamate receptors and nociception: implications for the drug treatment of pain," *CNS Drugs 15*:29-58, Adis International Limited, New Zealand (2001).

Fundytus, M., et al., "Antisense oligonucleotide knockdown of mGluR$_1$ alleviates hyperalgesia and allodynia associated with chronic inflammation," *Pharmacal. Biochem. Behav. 73*:401-410, Elsevier Science Inc., United States (2002).

Fundytus, M., et al., "In vivo anti nociceptive activity of anti-rat mGluR1 and mGluR$_5$ antibodies in rats," *Neuroreport. 9*:731-735, Rapid Science Publishers, United Kingdom (1998).

Fundytus, M., et al., "Knockdown of spinal metabotropic glutamate receptor 1(mGluR$_1$) alleviates pain and restores opioid efficacy after nerve injury in rats," *Br. J. Pharmacal. 132*:354-367, Nature Publishing Group, United Kingdom (2001).

Goodson, J., "Dental Applications," in *Medical Applications of Controlled Release*, vol. 2, Chapter 6, pp. 115-138, R., Langer and L. Wise (eds.), CRC Press, Boca Raton, Florida, United States (1984).

Grupp, I., et al., "Protection against hypoxia-reoxygenation in the absense of poly (ADP-ribose) synthetase in isolated working hearts," *J. Mol. Cell Cardiol. 31*:297-303, Academic Press, United Kingdom (1999).

Hanson, G.,"Analgesic, Antipyretic and Anti-Inflammatory Drugs," in *Remington:The Science and Practice of Pharmacy Valli*, 19th Edition, pp. 1196-1221, Gennaro, A., ed., Mack Publishing Co., Easton, Pensylvania, United States (1995).

Hargreaves, K., et al., "A New and Sensitive Method for Measuring Thermal Nociception in Cutaneous Hyperalgesia," *Pain 32*:77-88, Elsevier/North-Holland, Netherlands (1988).

Howard, M., III, et al., "Intracerebral drug delivery in rats with lesion-induced memory deficits," *J. Neurosurg. 71*:105-112, American Association of Neurological Surgeons, United States (1989).

Insel, P., "Analgesic-Antipyretic and Anti-inflammatory Agents and Drugs Employed in the Treatment of Gout", in Goodman & Gilman's The Pharmacological Basis of Therapeutics, 9th Edition, pp. 617-657, Hardman, J., et al., eds., New York: McGraw-Hill, United States (1996).

Kaiho, T., et al., "Cardiotonic agents. 1-Methyl-7-(4-pyridyl)-5,6,7,8-tetrahydro-3 (2H)-isoquinolinones and related compounds. Synthesis and Activity," *J. Med. Chem. 32*:351-357, American Chemical Society, United States (1989).

Kakeya, N., et al., "Studies on prodrugs of cephalosporins. I. Synthesis and biological properties of glycyloxybenzoyloxymethyl and glycylaminobenzoyloxymethly esters of 7 β-[2-(2- aminothiazol-4-yl)-(Z)-2-methoxyiminoactemido]-3-methyl-3-cephem-4-carboxyic acid," *Chem. Pharm. Bull. (Tokyo) 32*:692-698, Pharmaceutical Society of Japan, Japan (1984).

Khadse, B., et al., "Antihelmintic Agents: Synthesis and Study of 2-($N^4$- substituted-$N^1$-piperazinyl) pyrido (3,2-d) thiazoles, 5-nitro-2-($N^4$-substituted-$N^1$-piperazinyl) Benzthiazoles and allied compounds as possible anthelminthic agents," *Bull. Haff. Inst. 1*:27-32, Haffkine Institute, India (1975).

Kim, S. and Chung, J., "An experimental model for peripheral neuropathy produced by segmental spinal nerve ligation in the rat," *Pain 50*:355-363, Elsevier Science Publishers, Netherlands (1992).

Langer, R. and Peppas, N., "Chemical and Physical Structure of Polymers as Carriers for Controlled Release of Bioactive Agents: A Review," *Macromol. Sci. Rev. Macromol. Chem. Phys. 23*:61-126, Marcel Dekker, Inc., United States (1983).

Langer, R., "New methods of drug delivery," *Science 249*:1527-1533. American Assoc. for the Advancement of Science, United States (1990).

Levin, R. and Wein, A., "Direct measurement of the anticholinergic activity of a series of pharmacological compounds on the canine and rabbit urinary bladder," *J. Urol.128*:128-396-398,The Williams & Wilkins Co., United States (1982).

Levy, R., et al., "Inhibitionof calcificationo f bioprosthetic heart valves by local controlled-release diphosphonate," *Science 228*:190-192, American Assoc. for the Advancement of Science, United States (1985).

Li, G., et al., "An Improved Procedure for the Preparation of Isothiocyanates from Primary Amines by Using Peroxide as the Dehydrosulfurization Reagent," *J. Org. Chem. 62*:4539-4540, American Chemistry Society, United States (1997).

Masu, M., et al., "Sequence and expressiono f a metabotropic glutamate receptor," *Nature 349*:760-765, Nature Publishing Group, United Kingdom (1991).

Maya, I., et al., "A practical one-pot synthesis of O-unprotected glycosyl thioureas," *Tetrahedron Lett. 42*:5413-5416, Elsevier Science Ltd., Netherlands (2001).

Meyers, A., et al., "The synthesis of chiral α, β-unsaturated and aryl oxazolines from ketones and arols via their triflates and pd-catalyzed CO and amino alcohol coupling," *Tetrahedron Lett. 33*:1181-1184, Pergamon Press PLC, United Kingdom (1992).

Miller, S., et al., "Growth factor upregulation of a phosphoinositide-coupled metabotropic glutamate receptor in cortical astrocytes," *J. Neurosci. 15*:6103-6109, Society for Neuroscience, United States (1995).

Mirakhur, R. and Dundee, J., "Glycopyrrolate: pharmacology and clinical use," *Anaesthesia 38*:1195-1204, The Association of Anaesthetists of Great Britain and Ireland, United Kingdom (1983).

Morgenstern, O., et al., "Studies on the Reaction of 2-Aminoacetophenone with Thiophosgene," *J. Heterocycle Chem. 28*:1091-1097, HeteroCorporation, United States (1991).

Nielsen, N. and Bundgaard, H., "Glycolamide esters as biolabile prodrugs of carboxylic acid agents: synthesis, stability, bioconversion, and physiochemical properties," *J. Pharm. Sci. 77*:285-298, American Pharmaceutical Association, United States (1988).

Ossowska, K., et al., "Blockade of the metabotropic glutamate receptor subtype 5 ($mGluR_5$) produces anti parkinsonian-like effects in rats," *Neuropharmacology 41*:413-420, Elsevier Science Ltd., England (2001).

Ouadi, A., et al., "Synthesis of a novel bifunctional chelating agent for actinum complexation," *Tetrahedron Lett. 41*:7207-7209, Elsevier Science Ltd., Netherlands (2000).

Prakash, L., et al., "A novel synthesis of fluorinated pyrido [2,3-d] pyrimidine derivatives," *J. Fluorine Chemistry 41*:303-310, Elsevier Sequoia, Netherlands (1988).

Radenbaugh, G. and Ravin, L., "Preformulation," in Remington: The Science and Practice of Pharmacy, 19th Edition, pp. 1447-1676, Gennaro, A., ed., Mack Pub. Co., Easton, Pennsylvania, United States (1995).

Ramalingam, K. and Nowotnik, D., "Syntheses of Some Isothiocyanatophenylboronic Acids," *Org. Prep. Proced. Int. 23*:729-734, Organic Preparations and Procedures Inc., Germany (1991).

Saudek, C., et al., "A preliminary trial of the programmable implantable medication system for insulin delivery," *N. Engl. J Med. 321*:574-579, Massachusetts Medical Society, United States (1989).

Scott, W., et al., "Palladium-Catalyzed Coupling of Vinyl Triflates with Organostannanes: 4-tert-Butyl-1-Vinylcyclohexene and 1-(4-tert-Butylcyclohexen-1-YL)-2-Propen-1-0ne," *Organic Synth. 68*:116-129, Wiley, United States (1990).

Sefton, M., "Implantable pumps," *Crit. Rev. Biomed. Eng. 14*:201-240, Begell House, Inc., United States (1987).

Seltzer, Z., et al., "A Novel Behavioral Model of Neuropathic Pain Disorders Produced in Rats by Partial Sciatic Nerve Injury," *Pain 43*:205-218, Elsevier Science B.V., Netherlands (1990).

Spooren, W., et al., "Novel allosteric antagonists shed light on $mglu_5$ receptors and CNS disorders," *Trends. Pharmacol. Sci. 22*:331-377, Elsevier Science Ltd., England (2001).

Stein, C., "Unilateral Inflammation of the Hindpaw in Rats as a Model of Prolonged Noxious Stimulation: Alterations in Behavior and Nociceptive Thresholds," *Pharmacol. Biochem. Behav. 31*:445-451, Pergamon Press, Plc., United States (1988).

Tatarczyńska, E., et al., "Potential anxiolytic- and antidepressant-like effects of MPEP, a potent, selective and systemically active mGlu5 recepotr antagonist," *Br. J. Pharmacol. 132*:1423-1430, Nature Publishing Group, England (2001).

Treat, J., et al., "Liposome Encapsulated Doxorubicin: Preliminary Results of Phase I and Phase II Trials," in Liposomes in the Therapy of Infectious Disease and Cancer: Proceedinhgs of a Ciba-Geigy-Squibb-UCLA Colloquium, Held at Lake Tahoe, California, Feb. 16-20, 1988, pp. 317-327 and 353-365, by Lopez-Berestein, G., et al., eds., Alan R. Liss, Inc., United States (Jan. 1989).

Treit, D., "Animal models for the study of anti-anxiety agents: a review," *Neurosci. Biobehav. Rev. 9*:203-222, Ankho International Inc., United States (1985).

Walker, K, et al., "Metabotropic glutamate receptor subtype 5 (mGlu5) and nociceptive function I. Selective blockade of mGlu5 receptors in models of acute, persistent and chronic pain," *Neutopharmacology 40*:1-9, Elsevier Science Ltd., United Kingdom (2001).

Wein, A., "Pharmacology of Incontinence," *Ural Clin. North. Am. 22*:557-577, Saunders, United States (1995).

Wong, L., et al., "New Synthesis of Nitroxyl Radicals of the Piperidine and Tetrahydropyridine Series," *Can. J. Chem. 52*:3381-3383, NRC Canada, Canada (1974).

Wright, M. and Pulley, S., "Vinyl triflates: a mechanistic study on their formation from carbonyl compounds and triflic anhydride," *J. Org. Chem. 54*:2886-2889, American Chemical Society, United States (1989).

International Search Report for International Application No. PCT/US2008/005329, European Patent Office, Netherlands, mailed on Jul. 23, 2008, 3 pages.

Unverified English language abstract of Japanese Patent Application No. JP 2003-192673A, European Patent Office, esp@ce.net Database (2003).

English language translation of Japanese Patent Publication No. JP 62-89679 A, Patent Bureau of Japan, Official Gazette of Unexamined Patents (1987).

Written Opinion for International Application No. PCT/US2008/005329, European Patent Office, Netherlands, mailed on Jul. 23, 2008, 6 pages.

English language abstract of Japanese Patent No. JP 11-199573, Kiyoshi, et al., Japanese Patent Office (1999).

Office Action mailed on Dec. 8, 2008 for U.S. Appl. No. 10/867,546, Kyle, et al., filed on Jun. 14, 2004.

Office Action mailed on Apr. 30, 2007 for U.S. Appl. No. 10/867,546, Kyle, et al., filed on Jun. 14, 2004.

Appendino, G. and Szallasi, A., "Clinically Useful Vanilloid Receptor TRPVI Antagonists: Just arround the Corner (or too Early to Tell)?" *Prog. Med. Chem. 44*:145-180, Elsevier B.V., Netherlands (2006).

Bianchi, B.R., et al., "[$^3$H]A-778317 [1-((R)-5-*tert*-Butyl-indan-1-yl)-3-isoquinolin-5-yl-urea]: a Novel, Steroselective, High-Affinity Antogonist Is a Useful Radioligand for the Human Transient Receptor Potential Vanilloid-1 (TRPV1) Receptor," *J. Pharmacol. Exp. Ther. 323*(1):285-293, The American Society for Pharmacology and Experimental Therapeutics, United States (2007).

Cui, M., et al., "TRPV1 Receptors in the CNS Play a Key Role in Broad-Spectrum Analgesia of TRPV1 Antagonists," *J. Neurosci. 26*(37):9385-9393, Society for Neuroscience, United States (2006).

Kanai, Y., et al., "Differential involvement of TRPV1 receptors at the central and peripheral nerves in CFA-induced mechanical and thermal hyperalgesia," *J. Pharm. Pharmacol. 59*:733-738, Pharmaceutical Society of Great Britain, England (2007).

Okuhara, D.Y., et al., "Transient receptor potential channels as drug targets," *Expert Opin. Ther. Targets 11*(3):391-401, Informa UK Ltd, England (2007).

Pomonis, J.D., et al., "*N*-(4-Tertiarybutylphenyl)-4-(3-cholorphyridin-2-yl)tetrahydropyrazine-1(2*h*)-carbox-amide (BCTC), a Novel, Orally Effective Vanilloid Receptor 1 Antagonist with Analgesic Properties: II. In Vivo Characterization in Rat Models of Inflammatory and Neuropathic Pain," *J. Pharmacol. Exp. Ther. 306*(1):387-393, The American Society for Pharmacology and Experimental Therapeutics, United States (2003).

Valenzano, K.J., et al., "*N*(4-Tertiarybutylphenyl)-4-(3-cholorphyridin-2-yl)tetrahydropyrazine-1(2*H*)-carbox-amide (BCTC), a Novel, Orally Effective Vanilloid Receptor 1 Antagonist with Analgesic Properties: I. In Vitro Characterization and Pharmacokinetic Properties," *J. Pharmacol. Exp. Ther. 306*(1):377-386, The American Society for Pharmacology and Experimental Therapeutics, United States (2003).

SUBSTITUTED PYRIDINES USEFUL FOR TREATING PAIN

This application is a National Stage of International Application No. PCT/US2008/005329, filed Apr. 25, 2008, which claims the benefit of U.S. provisional application No. 60/924,056, filed Apr. 27, 2007 and U.S. provisional application No. 60/924,377, filed May 11, 2007, the disclosure of each of which is incorporated by reference herein in its entirety.

BACKGROUND OF THE INVENTION

1. Field of the Invention

The present invention relates to novel compounds, pharmaceutically acceptable derivatives thereof, compositions thereof and methods for treating or preventing a condition such as pain comprising administering to an animal said compounds and compositions.

2. Background Art

Pain is the most common symptom for which patients seek medical advice and treatment. Pain can be acute or chronic. While acute pain is usually self-limited, chronic pain persists for three months or longer and can lead to significant changes in a patient's personality, lifestyle, functional ability and overall quality of life (K. M. Foley, Pain, in Cecil Textbook of Medicine 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vaniloid receptors to pain processing (V. Di Marzo et al., Current Opinions in Neurobiology, 12:372-379 (2002)).

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. K. M. Foley, Pain, in Cecil Textbook of Medicine 100-107 (J. C. Bennett and F. Plum eds., 20th ed. 1996). In addition to the above-listed treatments, neuropathic pain, which can be difficult to treat, has also been treated with anti-epileptics (e.g. gabapentin, carbamazepine, valproic acid, topiramate, phenytoin), NMDA antagonists (e.g. ketamine, dextromethorphan), topical lidocaine (for post-herpetic neuralgia), and tricyclic antidepressants (e.g. fluoxetine, sertraline and amitriptyline).

Urinary incontinence ("UI") is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority starts between the ages of 14 and 24. The disease typically affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. The Merck Manual of Medical Information 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

International publication no. WO 98/31677 describes a class of aromatic amines derived from cyclic amines that are useful as antidepressant drugs.

International publication no. WO 01/027107 describes a class of heterocyclic compounds that are sodium/proton exchange inhibitors.

International publication no. WO 99/37304 describes substituted oxoazaheterocycly compounds useful for inhibiting factor Xa.

U.S. Pat. No. 6,248,756 to Anthony et al. and international publication no. WO 97/38665 describes a class of piperidine-containing compounds that inhibit farnesyl-protein transferase (Ftase).

International publication no. WO 98/31669 describes a class of aromatic amines derived from cyclic amines useful as antidepressant drugs.

International publication no. WO 97/28140 describes a class of piperidines derived from 1-(piperazin-1-yl)aryl(oxy/amino)carbonyl-4-aryl-piperidine that are useful as 5-HT$_{1Db}$ receptor antagonists.

International publication no. WO 97/38665 describes a class of piperidine containing compounds that are useful as inhibitors of farnesyl-protein transferase.

U.S. Pat. No. 4,797,419 to Moos et al. describes a class of urea compounds for stimulating the release of acetylcholine and useful for treating symptoms of senile cognitive decline.

U.S. Pat. No. 5,891,889 describes a class of substituted piperidine compounds that are useful as inhibitors of farnesyl-protein transferase, and the farnesylation of the oncogene protein Ras.

U.S. Pat. No. 6,150,129 to Cook et al. describes a class of dinitrogen heterocycles useful as antibiotics.

U.S. Pat. No. 5,529,998 to Habich et al. describes a class of benzooxazolyl- and benzothiazolyloxazolidones useful as antibacterials.

International publication no. WO 01/57008 describes a class of 2-benzothiazolyl urea derivatives useful as inhibitors of serine/threonine and tyrosine kinases.

International publication no. WO 02/08221 describes aryl piperazine compounds useful for treating chronic and acute pain conditions, itch, and urinary incontinence.

International publication no. WO 00/59510 describes aminopyrimidines useful as sorbitol dehydrogenase inhibitors.

Japanese patent application no. 11-199573 to Kiyoshi et al. describes benzothiazole derivatives that are neuronal 5HT3 receptor agonists in the intestinal canal nervous system and useful for treating digestive disorders and pancreatic insufficiency.

German patent application no 199 34 799 to Rainer et al. describes a chiral-smectic liquid crystal mixture containing compounds with 2 linked (hetero)aromatic rings or compounds with 3 linked (hetero)aromatic rings.

M. Chu-Moyer et al., *J. Med. Chem.* 45:511-528 (2002) describes heterocycle-substituted piperazino-pyrimidines useful as sorbitol dehydrogenase inhibitors.

B. G. Khadse et al., *Bull. Haff. Instt.* 1(3):27-32 (1975) describes 2-(N$^4$-substituted-N$^1$-piperazinyl)pyrido(3,2-d)thiazoles and 5-nitro-2-(N$^4$-substituted-N$^1$-piperazinyl)benzthiazoles useful as anthelmintic agents.

U.S. Patent Application Publication No. US 2004/0186111 A1 and International publication no. WO 2004/058754 A1 describe a class of compounds that are useful for treating pain.

U.S. Patent Application Publication No. US 2006/0199824-A1 and International publication no. WO 2005/009987 A1 describe a class of compounds that are useful for treating pain.

U.S. Patent Application Publication No. US 2006/0128717 A1 and International publication no. WO 2005/009988 A1 describe a class of compounds that are useful for treating pain.

U.S. Published Application Nos. 20060128775, 20050009841, and 20070027159 describe classes of TRPV1 antagonists.

There remains, however, a clear need in the art for new drugs useful for treating or preventing pain, UI, an ulcer, IBD, and IBS. Citation of any reference in the Background of the Invention Section of this application is not to be construed as an admission that such reference is prior art to the present application.

BRIEF SUMMARY OF THE INVENTION

The invention encompasses compounds of Formula (I) as defined herein.

The invention further encompasses compounds of Formula (II) as defined herein.

The invention further encompasses compounds of Formula (III) as define herein.

The invention further encompasses compounds of Formula (IV) as defined herein.

The invention further encompasses compounds of Formula (V) as defined herein.

The invention further encompasses pharmaceutically acceptable derivatives of a compound of Formulae (I)-(V).

A compound of Formula (I)-(V) or a pharmaceutically acceptable derivative thereof is useful for treating or preventing pain, UI, an ulcer, IBD, or IBS (each being a "Condition") in an animal.

The invention also relates to compositions comprising an effective amount of a compound of Formulae (I)-(V) or a pharmaceutically acceptable derivative thereof and a pharmaceutically acceptable carrier or excipient. The compositions are useful for treating or preventing a Condition in an animal.

The invention further relates to methods for treating a Condition, comprising administering to an animal in need thereof an effective amount of a compound of Formulae (I)-(V), or a pharmaceutically acceptable derivative thereof.

The invention further relates to methods for preventing a Condition, comprising administering to an animal in need thereof an effective amount of a compound of Formulae (I)-(V), or a pharmaceutically acceptable derivative thereof.

The invention still further relates to methods for inhibiting Vanilloid Receptor 1 ("TRPV1") function in a cell, comprising contacting a cell capable of expressing TRPV1 with an effective amount of a compound of Formulae (I)-(V), or a pharmaceutically acceptable derivative thereof.

The invention still further relates to methods for preparing a composition, comprising the step of admixing a compound of Formulae (I)-(V), or a pharmaceutically acceptable derivative thereof and a pharmaceutically acceptable carrier or excipient.

The invention still further relates to a kit comprising a container containing an effective amount of a compound of Formulae (I)-(V), or a pharmaceutically acceptable derivative thereof.

Certain compounds of the present invention, especially those having one or more polar groups (e.g., hydroxy, —SO$_2$—, —PO$_3$—, etc.) on the R$_2$ substituent will have one or more of the following properties compared to prior art compounds: improved solubility, improved pharmacokinetics, and/or reduced side effects. Improved solubility allows for ease of formulation and greater predictability of exposure at target area. Improved pharmacokinetics allows for greater and/or more predictable bioavailability. Reduced side effects can allow for a greater clinical or commercial acceptance of a therapy. For pain medications, typically encountered side effects include sedation, ataxia, muscle relaxation, tremor, and flat body posture. An improved side effect profile in one or more of these areas would allow wider acceptance of compounds, provide less risk of adverse effects in the clinic, and provide a greater therapeutic index (i.e. gap between effective doses and doses that induce adverse effects).

Compounds of Formulae I-V are potent at TRPV1 receptors, and are highly soluble in aqueous solutions at either pH 6.8 or pH 1.2.

The present invention can be understood more fully by reference to the following detailed description and illustrative examples, which are intended to exemplify non-limiting embodiments of the invention.

DETAILED DESCRIPTION OF THE INVENTION

The invention encompasses compounds of Formula (I):

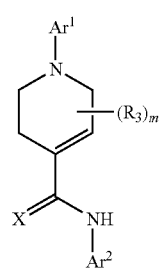

(I)

or a pharmaceutically acceptable derivative thereof, wherein:
Ar$^1$ is

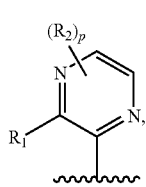

(i)

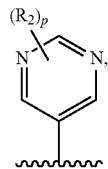

(ii)

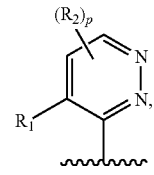

(iii)

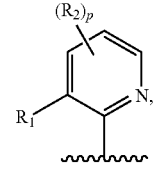

(iv)

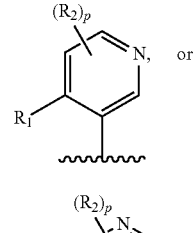

(v)

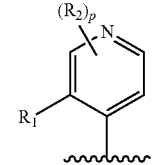

(vi)

Ar$^2$ is

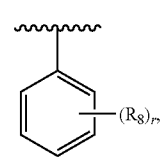

(a)

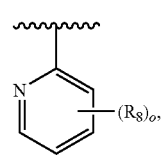

(b)

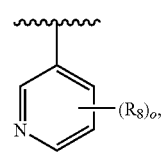

(c)

-continued (e)
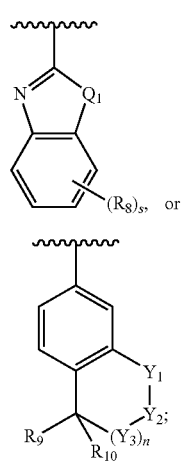

(f)
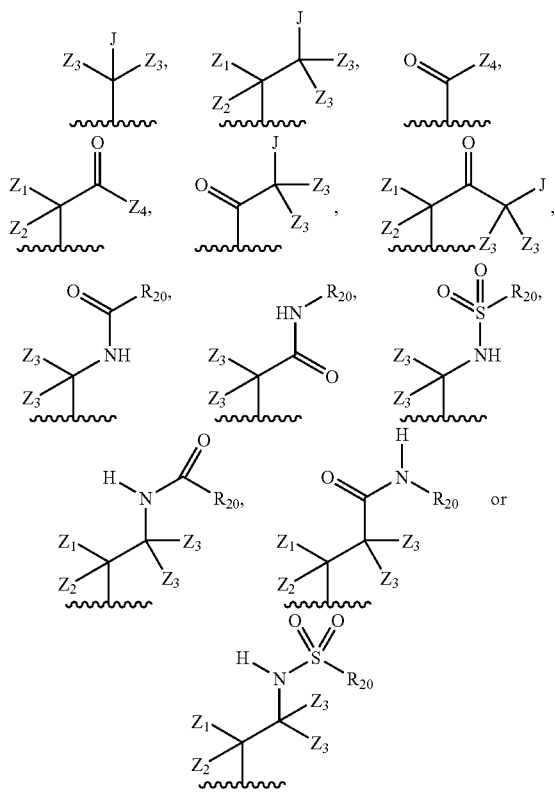

X is O or S;

$Q_1$ is O, S, or NH;

$R_1$ is hydrogen, halo, $(C_1-C_4)$alkyl, methyl, nitro, cyano, hydroxy, methoxy, amino, trihalomethyl, dihalomethyl, halomethyl, OC(halo)$_3$, OCH(halo)$_2$, or OCH$_2$(halo);

each $R_2$ is independently:
(a) halo, OH, O$(C_1-C_4)$alkyl, CN, NO$_2$, or NH$_2$;
(b) $(C_1-C_{10})$alkyl, $(C_2-C_{10})$alkenyl, or $(C_2-C_{10})$alkynyl;
(c) phenyl; or
(d) a group of Formula $Q_2$:

wherein $Q_2$ is $Z_1$ is H, OR$_7$, SR$_7$, CH$_2$—OR$_7$, CH$_2$—SR$_7$, CH$_2$—N(R$_{20}$)$_2$, or halo;

$Z_2$ is H, $(C_1-C_6)$alkyl, $(C_2-C_6)$alkenyl, $(C_2-C_6)$alkynyl, —CH$_2$OR$_7$, phenyl, or halo;

each $Z_3$ is independently H, $(C_1-C_6)$alkyl, $(C_2-C_6)$alkenyl, $(C_2-C_6)$alkynyl, or phenyl;

$Z_4$ is H, OH, OR$_{20}$, $(C_1-C_6)$alkyl, or N(R$_{20}$)$_2$;

J is OR$_{20}$, SR$_{20}$, N(R$_{20}$)$_2$ or CN;

provided that at least one $R_2$ group is a group of Formula $Q_2$, and provided that when $Z_1$ is OR$_7$ or SR$_7$, $Z_2$ is not halo;

each of $Y_1$, $Y_2$, and $Y_3$ is C or NR', provided that at least one of $Y_1$, $Y_2$, and $Y_3$ is CR', wherein R' is H or $(C_1-C_6)$alkyl;

each $R_3$ is independently
(a) hydrogen, CH$_2$OR$_7$, or $(C_1-C_6)$alkyl;
(b) two $R_3$ groups together form a $(C_2-C_6)$bridge, which is unsubstituted or substituted with 1, 2 or 3 independently selected $R_8$ groups, and which bridge optionally contains —HC═CH— within the $(C_2-C_6)$bridge; or
(c) two $R_3$ groups together form a —CH$_2$—N(R$_a$)—CH$_2$— bridge, a

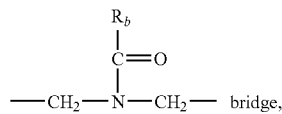

or a

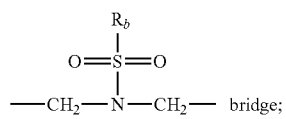

$R_a$ is —H, $(C_1-C_6)$alkyl, $(C_3-C_8)$cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;

each $R_b$ is independently:
(a) —H, $(C_1-C_6)$alkyl, $(C_3-C_8)$cycloalkyl, -(3- to 7-membered)heterocycle, —N(R$_c$)$_2$, —N(R$_c$)—$(C_3-C_8)$cycloalkyl, or —N(R$_c$)-(3- to 7-membered)heterocycle; or
(b) phenyl, (5- or 6-membered)heteroaryl, —N(R$_c$)-phenyl, or —N(R$_c$)-(5- to 10-membered)heteroaryl, each of which is unsubstituted or substituted with 1, 2 or 3 independently selected R$_7$ groups;

each R$_c$ is independently —H or $(C_1-C_4)$alkyl;

each R$_8$ is independently (a) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups, or (b) H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), O—CN, CN, OH, halo, N$_3$, NO$_2$, CH═NR$_7$, N(R$_7$)$_2$, NR$_7$OH, OR$_7$, C(O)R$_7$, C(O)OR$_7$, OC(O)R$_7$, OC(O)OR$_7$, SR$_7$, S(O)R$_7$, or S(O)$_2$R$_7$ or SO$_2$CH$_2$(halo)O$(C_1-C_6)$alkyl;

R$_7$ is H, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyalkyl, $(C_1-C_6)$alkoxy$(C_1-C_6)$alkyl, $(C_1-C_6)$alkyl-N(R$_{20}$)$_2$, or CON(R$_{20}$)$_2$;

each of R$_9$ and R$_{10}$ is independently hydrogen or $(C_1-C_6)$alkyl; or together with the carbon atom to which they are attached form a $(C_3-C_6)$ carbocycle;

R$_{20}$ is H, $(C_1-C_4)$alkyl, halo$(C_1-C_4)$alkyl, hydroxy$(C_1-C_4)$alkyl, $(C_1-C_4)$alkoxy$(C_1-C_4)$alkyl or $(C_3-C_8)$carbocycle;

n is 0, 1, or 2;

each of m, o, and s is independently 0, 1, 2, 3, or 4;

p is 1, 2, or 3; and each of q and r is independently 0, 1, 2, 3, 4, or 5.

In one embodiment, a compound of Formula I is a pharmaceutically acceptable derivative of a compound of Formula I.

In another embodiment, a compound of Formula I is a compound of Formula I wherein the derivative is a pharmaceutically acceptable salt.

In another embodiment, a compound of Formula I is a pharmaceutically acceptable salt of a compound of Formula I.

In one embodiment, $Ar^1$ is

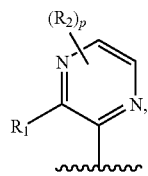
(i)

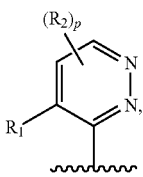
(ii)

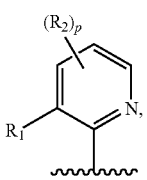
(iii)

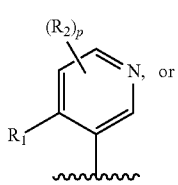
(iv)

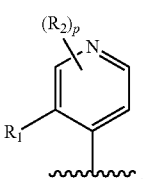
(v)

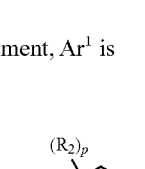
(vi)

In another embodiment, $Ar^1$ is

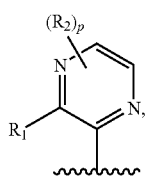
(i)

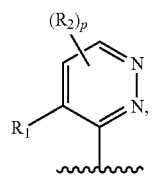
(iii)

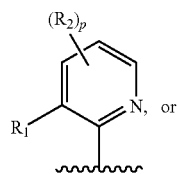
(iv)

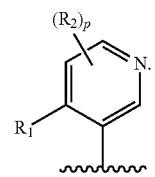
(v)

In one embodiment, $Ar^1$ is a pyrimidyl group, a pyrazinyl group, or a pyridazinyl group.

In another embodiment, $Ar^1$ is substituted with one or more $R_2$ groups wherein each $R_2$ group is an alkyl group substituted with at least one hydroxy group, preferably two hydroxy groups.

In another embodiment, $R_2$ is

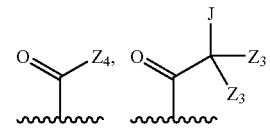

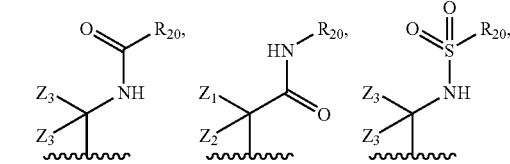

In another embodiment, R$_2$ is

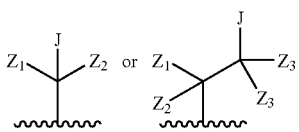

wherein Z$_1$, Z$_2$, Z$_3$, and J are defined above.

In another embodiment, R$_2$ is

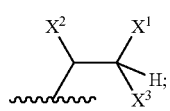

wherein each of X$^1$, X$^2$, and X$^3$ is independently hydroxy, (C$_1$-C$_6$)alkyl, amino, or (C$_1$-C$_6$)alkoxy provided that at least one of X$^1$, X$^2$, or X$^3$ is hydroxy.

In another embodiment R$_2$ is

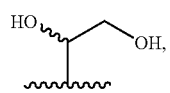

wherein the compound of Formula I is racemic.

In another embodiment R$_2$ is

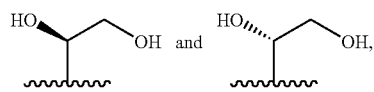

wherein the % ee of the R enantiomer is greater than 60%.

In another embodiment R$_2$ is

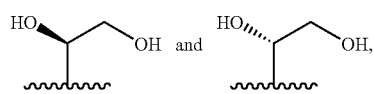

wherein the % ee of the R enantiomer is greater than 70%.

In another embodiment R$_2$ is

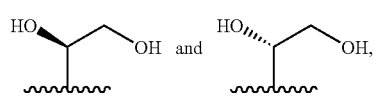

wherein the % ee of the R enantiomer is greater than 80%.

In another embodiment R$_2$ is

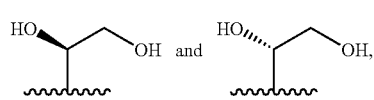

wherein the % ee of the R enantiomer is greater than 90%.

In another embodiment R$_2$ is

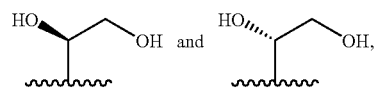

wherein the % ee of the R enantiomer is greater than 99%.

In another embodiment R$_2$ is

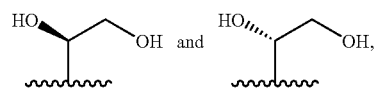

wherein the % ee of the S enantiomer is greater than 60%.

In another embodiment R$_2$ is

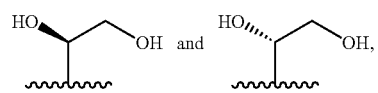

wherein the % ee of the S enantiomer is greater than 70%.

In another embodiment R$_2$ is

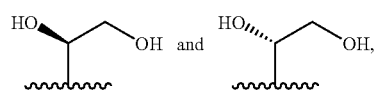

wherein the % ee of the S enantiomer is greater than 80%.

In another embodiment R$_2$ is

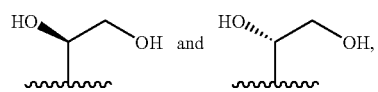

wherein the % ee of the S enantiomer is greater than 90%.

In another embodiment R$_2$ is

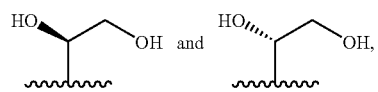

wherein the % ee of the S enantiomer is greater than 99%.

In another embodiment, R$_2$ is

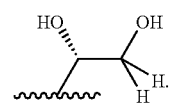

In another embodiment, $R_2$ is

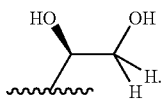

In another embodiment, each $R_3$ is independently —H, or $(C_1\text{-}C_6)$alkyl.

In another embodiment, two $R_3$ groups together form a $(C_2\text{-}C_6)$bridge, which is unsubstituted or substituted with 1, 2 or 3 independently selected $R_8$ groups, and which bridge optionally contains —HC=CH— within the $(C_2\text{-}C_6)$bridge.

In another embodiment, two $R_3$ groups together form a $(C_2\text{-}C_6)$bridge, which is unsubstituted or substituted with an $R_8$ group, and which bridge optionally contains —HC=CH— within the $(C_2\text{-}C_6)$bridge.

In another embodiment, two $R_3$ groups together form a $(C_2\text{-}C_3)$bridge, which is unsubstituted or substituted with an $R_8$ group, and which bridge optionally contains —HC=CH— within the $(C_2\text{-}C_3)$bridge.

In another embodiment, two $R_3$ groups together form a $(C_2\text{-}C_3)$bridge, which is unsubstituted and which bridge optionally contains —HC=CH— within the $(C_2\text{-}C_3)$bridge.

In another embodiment, two $R_3$ groups together form a $(C_2)$bridge, a —HC=CH— bridge, or a $(C_3)$bridge each of which is unsubstituted.

In another embodiment, two $R_3$ groups together form a $(C_2\text{-}C_6)$bridge, which is unsubstituted or substituted with 1, 2 or 3 independently selected $R_8$ groups, which bridge optionally contains —HC=CH— within the $(C_2\text{-}C_6)$bridge, and which bridge joins positions 2 and 6 of the 1,2,3,6-tetrahydropyridine ring.

In another embodiment, two $R_3$ groups together form a $(C_2\text{-}C_6)$bridge, which is unsubstituted or substituted with an $R_8$ group, which bridge optionally contains —HC=CH— within the $(C_2\text{-}C_6)$bridge, and which bridge joins positions 2 and 6 of the 1,2,3,6-tetrahydropyridine ring.

In another embodiment, two $R_3$ groups together form a $(C_2\text{-}C_3)$bridge, which is unsubstituted or substituted with an $R_8$ group, which bridge optionally contains —HC=CH— within the $(C_2\text{-}C_3)$bridge, and which bridge joins positions 2 and 6 of the 1,2,3,6-tetrahydropyridine ring.

In another embodiment, two $R_3$ groups together form a $(C_2\text{-}C_3)$bridge, which is unsubstituted, which bridge optionally contains —HC=CH— within the $(C_2\text{-}C_3)$bridge, and which bridge joins positions 2 and 6 of the 1,2,3,6-tetrahydropyridine ring.

In another embodiment, two $R_3$ groups together form a $(C_2)$bridge, a —HC=CH— bridge, or a $(C_3)$bridge each of which is unsubstituted, and which bridge joins positions 2 and 6 of the 1,2,3,6-tetrahydropyridine ring.

In another embodiment, two $R_3$ groups together form a —$CH_2$—$N(R_a)$—$CH_2$— bridge (B1), a

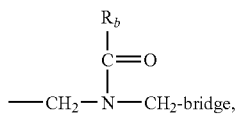

or a

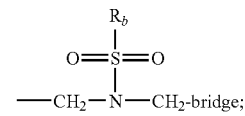

wherein $R_a$ is selected from —H, $(C_1\text{-}C_6)$alkyl, $(C_3\text{-}C_8)$cycloalkyl,
—$CH_2$—C(O)—$R_c$, —$(CH_2)$—C(O)—$OR_c$, —$(CH_2)$—C(O)—$N(R_c)_2$, —$(CH_2)_2$—O—$R_c$,
—$(CH_2)_2$—$S(O)_2$—$N(R_c)_2$, or —$(CH_2)_2$—$N(R_c)S(O)_2$—$R_c$;

$R_b$ is selected from:

(a) —H, $(C_1\text{-}C_6)$alkyl, $(C_3\text{-}C_8)$cycloalkyl, (3- to 7-membered)heterocycle, —$N(R_c)_2$, —$N(R_c)$—$(C_3\text{-}C_8)$cycloalkyl, or —$N(R_c)$-(3- to 7-membered)heterocycle; or (b) phenyl, (5- or 6-membered)heteroaryl, —$N(R_c)$-phenyl, or —$N(R_c)$-(5- to 10-membered)heteroaryl, each of which is unsubstituted or substituted with 1, 2 or 3 independently selected $R_7$ groups; and each $R_c$ is independently selected from —H or $(C_1\text{-}C_4)$alkyl;

In another embodiment, the B1, B2, or B3 bridge joins positions 2 and 6 of the 1,2,3,6-tetrahydropyridine ring.

In another embodiment, X is O.

In one embodiment, $Ar^1$ is

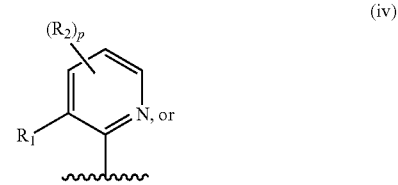

(iv)

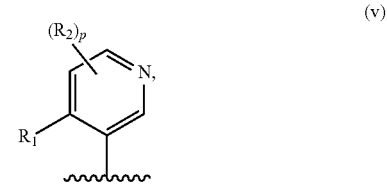

(v)

wherein $R_1$ is halo or trihalomethyl, and p is 1.

In another embodiment, $Ar^2$ is

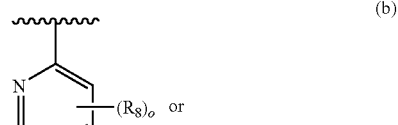

(b)

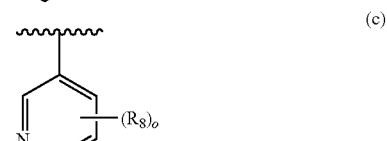

(c)

and each o is 0, 1, or 2; and $R_8$ is halo, trihalomethyl, or trihalomethoxy.

In another embodiment, Ar² is

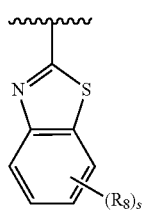
(e)

s is 0, 1, or 2; R₈ is halo, trihalomethyl, or trihalomethoxy.

In another embodiment, Ar² is

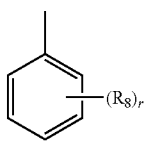
(a)

where o is 0, 1, or 2, and R₈ is halo, trihalomethyl or trihalomethoxy.

In another embodiment, R₁ is halo, CH₃, C(halo)₃, CH(halo)₂, CH₂(halo), or OC(halo)₃.

One embodiment is directed to compounds of Formula I above, or a pharmaceutically acceptable salt thereof, wherein:

Ar¹ is

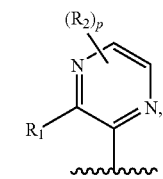
(i)

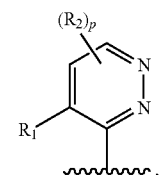
(iii)

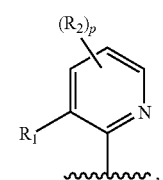
(iv)

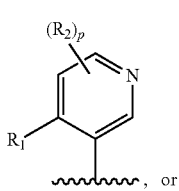
(v)
, or

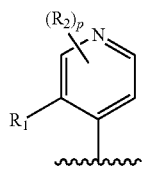
(vi)

Ar² is

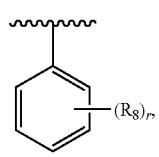
(a)

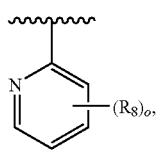
(b)

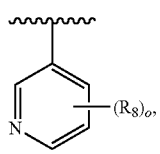
(c)

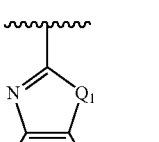
(e)

or

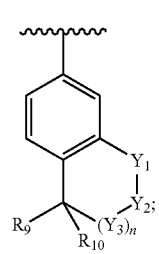
(f)

X is O or S;

Q₁ is O, S, or NH;

R₁ is hydrogen, halo, (C₁-C₄)alkyl, methyl, nitro, cyano, hydroxy, methoxy, amino, trihalomethyl, dihalomethyl, halomethyl, OC(halo)₃, OCH(halo)₂, or OCH₂(halo);

each R₂ is independently:
(a) halo, OH, O(C₁-C₄)alkyl, CN, NO₂, or NH₂;
(b) (C₁-C₁₀)alkyl, (C₂-C₁₀)alkenyl, or (C₂-C₁₀)alkynyl;
(c) phenyl; or (d) a group of formula $Q_2$:
wherein $Q_2$ is

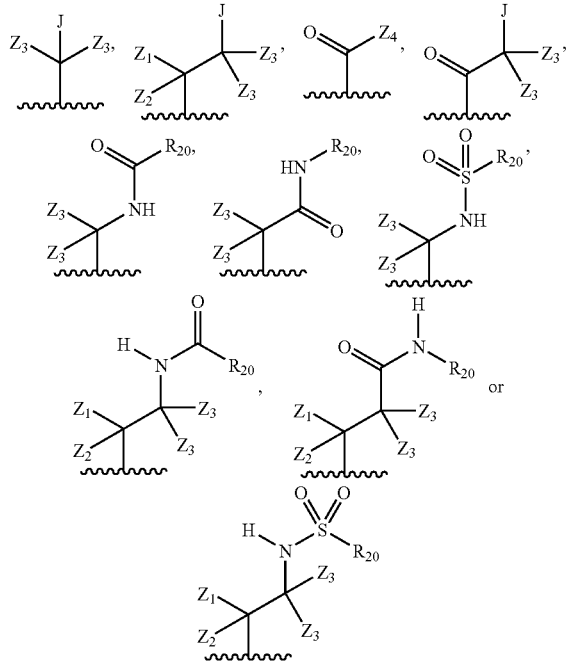

$Z_1$ is H, $OR_7$, $SR_7$, $CH_2$—$OR_7$, $CH_2$—$SR_7$, $CH_2$—$N(R_{20})_2$, or halo;

$Z_2$ is H, $(C_1$-$C_6)$alkyl, $(C_2$-$C_6)$alkenyl, $(C_2$-$C_6)$alkynyl, phenyl, or halo;

each $Z_3$ is independently H, $(C_1$-$C_6)$alkyl, $(C_2$-$C_6)$alkenyl, $(C_2$-$C_6)$alkynyl, or phenyl;

$Z_4$ is H, OH, $OR_{20}$, $(C_1$-$C_6)$alkyl, or $NR_{20}$;

J is $OR_{20}$, $SR_{20}$, or $N(R_{20})_2$;

provided that at least one $R_2$ group is a group of formula $Q_2$, and provided that when $Z_1$ is $OR_7$ or $SR_7$, $Z_2$ is not halo;

each of $Y_1$, $Y_2$, and $Y_3$ is C or NR' provided that at least one of $Y_1$, $Y_2$, and $Y_3$ is CR', wherein R' is H or $C_1$-$C_6$alkyl;

each $R_3$ is independently hydrogen or alkyl;

$R_7$ is H, $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, phenyl, $(C_1$-$C_6)$haloalkyl, $(C_1$-$C_6)$hydroxyalkyl, $(C_1$-$C_6)$alkoxy$(C_1$-$C_6)$alkyl, $(C_1$-$C_6)$alkyl-$N(R_{20})_2$, or $CON(R_{20})_2$;

each $R_8$ is independently H, $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, phenyl, $CH_2C(halo)_3$, $C(halo)_3$, $CH(halo)_2$, $CH_2(halo)$, $OC(halo)_3$, $OCH(halo)_2$, $OCH_2(halo)$, O—CN, OH, halo, $N_3$, $NO_2$, CH=$NR_7$, $N(R_7)_2$, $NR_7OH$, $OR_7$, $C(O)R_7$, $C(O)OR_7$, $OC(O)R_7$, $OC(O)OR_7$, $SR_7$, $S(O)R_7$, or $S(O)_2R_7$;

each of $R_9$ and $R_{10}$ is independently hydrogen or $C_1$-$C_6$ alkyl; or together with the carbon atom to which they are attached form a $C_3$-$C_6$ carbocycle;

$R_{20}$ is H, $(C_1$-$C_4)$alkyl, halo$(C_1$-$C_4)$alkyl, hydroxy$(C_1$-$C_4)$alkyl, or $(C_1$-$C_4)$alkoxy$(C_1$-$C_4)$alkyl;

each n is 0, 1, or 2;

each of m, o, and s is independently 0, 1, 2, 3, or 4;

p is 1, 2, or 3; and each of q and r is 0, 1, 2, 3, 4, or 5.

In certain embodiments, compounds of Formula I are highly soluble in aqueous solutions at either pH 6.8 or pH 1.2, are very potent at the TRPV1 receptor, are expected to have good bioavailability, and are believed to have a good therapeutic index Compounds of Formula (II)

The invention further encompasses compounds of Formula (II):

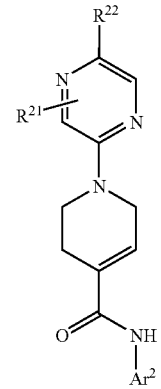

(II)

or a pharmaceutically acceptable derivative thereof, wherein:
$Ar^2$ is

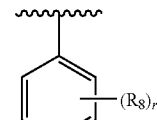

(a)

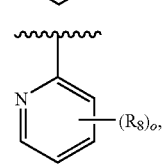

(b)

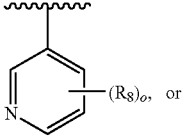

(c), or

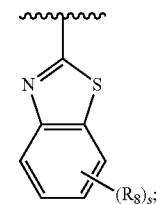

(e)

$R^{21}$ is hydrogen, halo, methyl, trihalomethyl, dihalomethyl, or halomethyl;

$R^{22}$ is

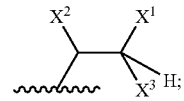

wherein each of $X^1$, $X^2$, and $X^3$ is independently hydroxy, alkyl, amino, or alkoxy, provided that at least one of $X^1$, $X^2$, or $X^3$ is hydroxy;

each $R_8$ is one or more of hydrogen, halo, $(C_1-C_6)$alkyl, $C(halo)_3$, $CH(halo)_2$, $CH_2(halo)$, $OC(halo)_3$, $OCH(halo)_2$, $OR_7$, $SC(halo)_3$, $OCH_2(halo)$, $SO_2C(halo)_3$, or $SO_2CH(halo)_2$; and each of o, r, and s is 1 or 2. Alternatively, each of each of o, r, and s is 0.

In another embodiment, $R^{22}$ is an alkyl group substituted with at least one hydroxy group, preferably two hydroxy groups.

In one embodiment, a compound of Formula II is a pharmaceutically acceptable derivative of a compound of Formula II.

In another embodiment, a compound of Formula II is a compound of Formula II wherein the derivative is a pharmaceutically acceptable salt.

In another embodiment, a compound of Formula II is a pharmaceutically acceptable salt of a compound of Formula II.

In another embodiment, $R^{22}$ is

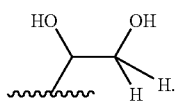

In another embodiment, $R^{22}$ is

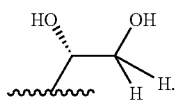

In another embodiment, $R_2$ is

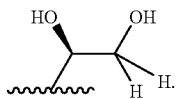

In another embodiment, $Ar^2$ is

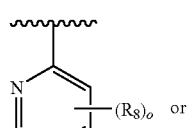

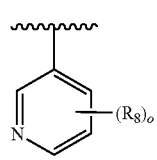

and each of o is 1, or 2; and $R_8$ is hydrogen, halo, trihalomethyl, or trihalomethoxy.

In another embodiment, $Ar^2$ is

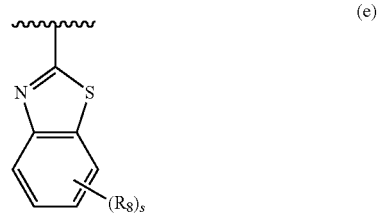

s is 1, or 2; $R_8$ is hydrogen, halo, trihalomethyl, or trihalomethoxy.

In another embodiment, $R^{21}$ is halo, $CH_3$, $C(halo)_3$, $CH(halo)_2$, $CH_2(halo)$, or $OC(halo)_3$.

Illustrative compounds of Formula II are listed below in Tables 1-6:

TABLE 1

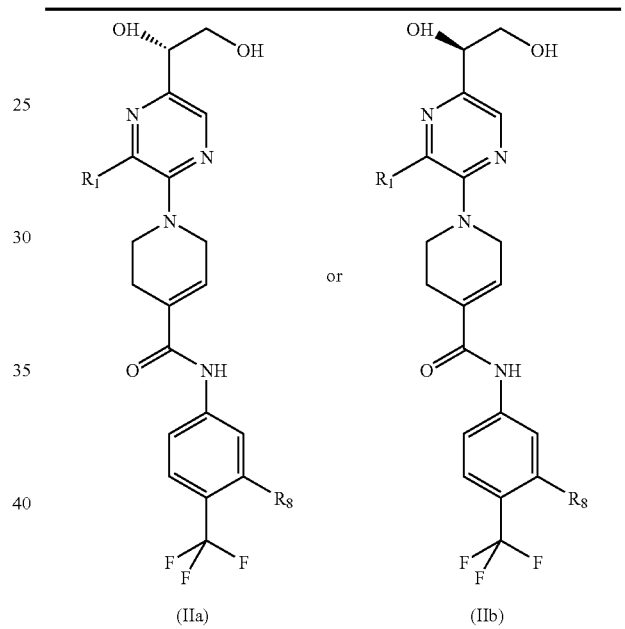

and pharmaceutically acceptable derivatives thereof, where:

| Compound | Formula | $R_1$ | $R_8$ |
|---|---|---|---|
| AA1 | IIa | —Cl | —Cl |
| AA2 | IIa | —Cl | —F |
| AA3 | IIa | —Cl | —OCH$_3$ |
| AA4 | IIa | —Cl | —OCH$_2$CH$_3$ |
| AA5 | IIa | —F | —Cl |
| AA6 | IIa | —F | —F |
| AA7 | IIa | —F | —OCH$_3$ |
| AA8 | IIa | —F | —OCH$_2$CH$_3$ |
| AA9 | IIa | —CF$_3$ | —Cl |
| AA10 | IIa | —CF$_3$ | —F |
| AA11 | IIa | —CF$_3$ | —OCH$_3$ |
| AA12 | IIa | —CF$_3$ | —OCH$_2$CH$_3$ |
| AA13 | IIa | —F | —H |
| AA14 | IIa | —CF$_3$ | —H |
| AA15 | IIa | —Cl | —H |
| B1 | IIb | —Cl | —Cl |
| BB2 | IIb | —Cl | —F |
| BB3 | IIb | —Cl | —OCH$_3$ |
| BB4 | IIb | —Cl | —OCH$_2$CH$_3$ |
| BB5 | IIb | —F | —Cl |
| BB6 | IIb | —F | —F |
| BB7 | IIb | —F | —OCH$_3$ |
| BB8 | IIb | —F | —OCH$_2$CH$_3$ |

TABLE 1-continued

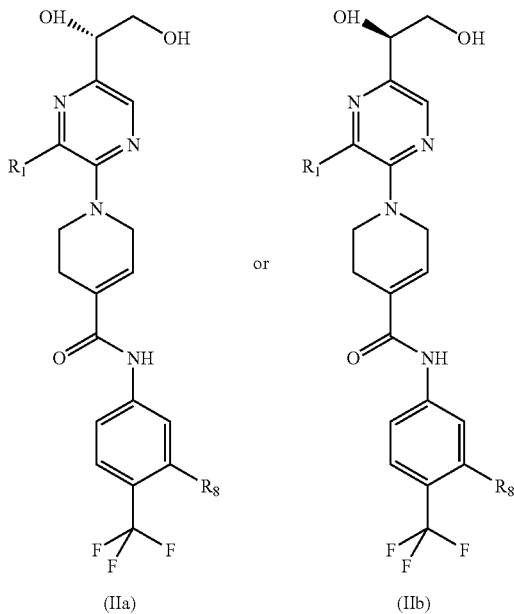

(IIa) or (IIb)

and pharmaceutically acceptable derivatives thereof, where:

| Compound | Formula | R₁ | R₈ |
|---|---|---|---|
| BB9 | IIb | —CF₃ | —Cl |
| BB10 | IIb | —CF₃ | —F |
| BB11 | IIb | —CF₃ | —OCH₃ |
| BB12 | IIb | —CF₃ | —OCH₂CH₃ |
| BB13 | IIb | —F | —H |
| BB14 | IIb | —CF₃ | —H |
| BB15 | IIb | —Cl | —H |

TABLE 2

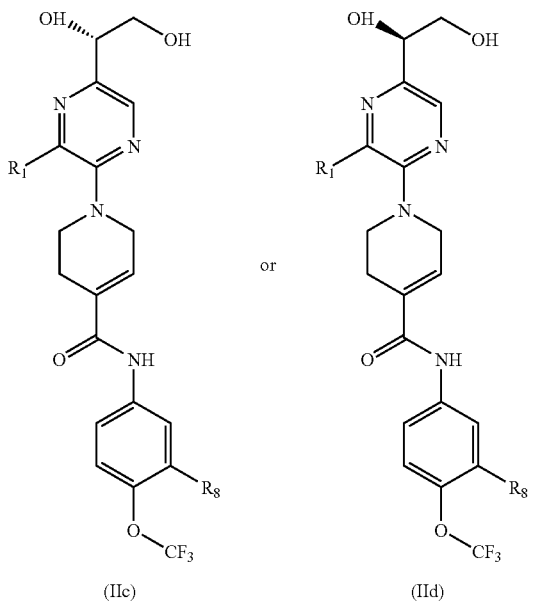

(IIc) or (IId)

and pharmaceutically acceptable derivatives thereof, where:

| Compound | Formula | R₁ | R₈ |
|---|---|---|---|
| CC1 | IIc | —Cl | —CH₃ |
| CC2 | IIc | —Cl | —CH₂CH₃ |

TABLE 2-continued

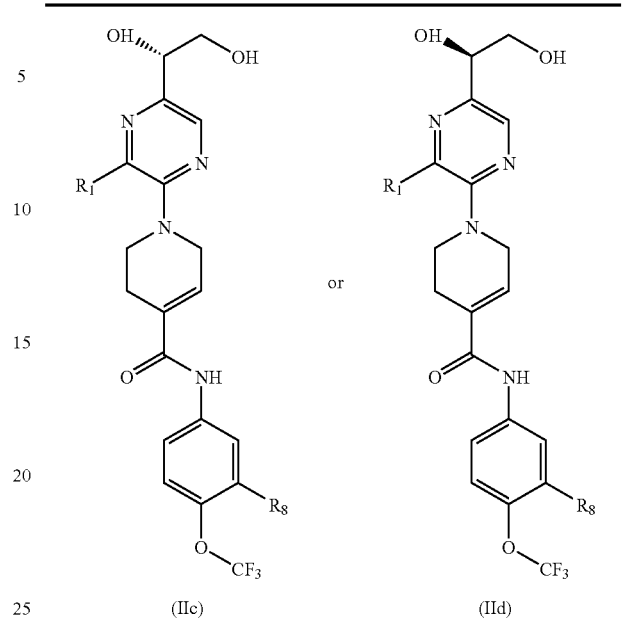

(IIc) or (IId)

and pharmaceutically acceptable derivatives thereof, where:

| Compound | Formula | R₁ | R₈ |
|---|---|---|---|
| CC3 | IIc | —Cl | —Cl |
| CC4 | IIc | —F | —CH₃ |
| CC5 | IIc | —F | —CH₂CH₃ |
| CC6 | IIc | —F | —Cl |
| CC7 | IIc | —CF₃ | —CH₃ |
| CC8 | IIc | —CF₃ | —CH₂CH₃ |
| CC9 | IIc | —CF₃ | —Cl |
| CC10 | IIc | —Cl | —H |
| CC11 | IIc | —F | —H |
| CC12 | IIc | —CF₃ | —H |
| DD1 | IId | —Cl | —CH₃ |
| DD2 | IId | —Cl | —CH₂CH₃ |
| DD3 | IId | —Cl | —Cl |
| DD4 | IId | —F | —CH₃ |
| DD5 | IId | —F | —CH₂CH₃ |
| DD6 | IId | —F | —Cl |
| DD7 | IId | —CF₃ | —CH₃ |
| DD8 | IId | —CF₃ | —CH₂CH₃ |
| DD9 | IId | —CF₃ | —Cl |
| DD10 | IId | —Cl | —H |
| DD11 | IId | —F | —H |
| DD12 | IId | —CF₃ | —H |

TABLE 3

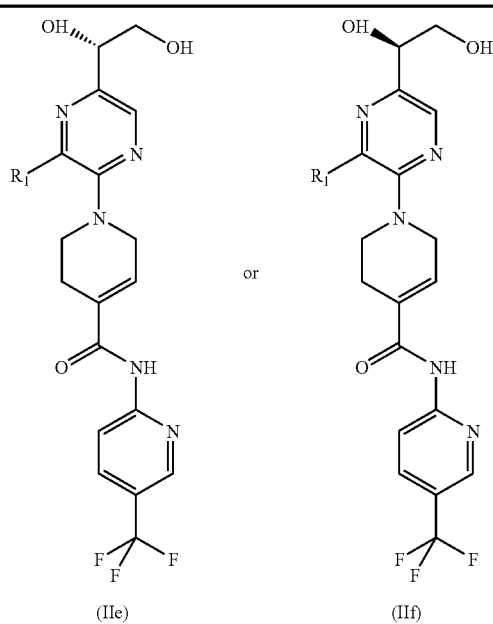

(IIe)     (IIf)

and pharmaceutically acceptable derivatives thereof, where:

| Compound | Formula | $R_1$ |
|---|---|---|
| EE1 | IIe | —Cl |
| EE2 | IIe | —F |
| EE3 | IIe | —$CF_3$ |
| FF1 | IIf | —Cl |
| FF2 | IIf | —F |
| FF3 | IIf | —$CF_3$ |

TABLE 4

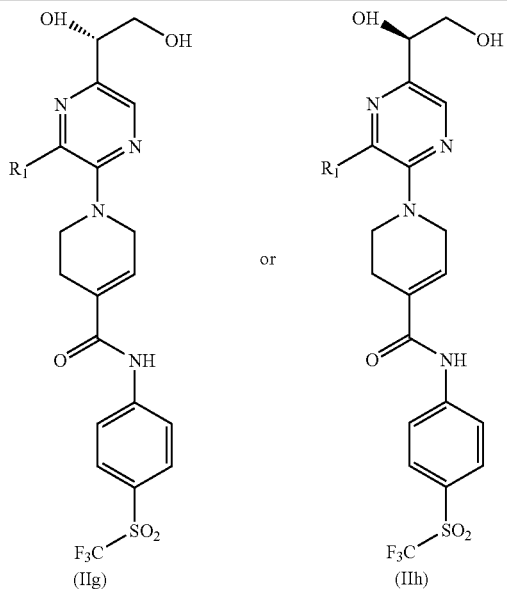

(IIg)     (IIh)

and pharmaceutically acceptable derivatives thereof, where:

| Compound | Formula | $R_1$ |
|---|---|---|
| GG1 | IIg | —Cl |
| GG2 | IIg | —F |
| GG3 | IIg | —$CF_3$ |
| HH1 | IIh | —Cl |

TABLE 4-continued

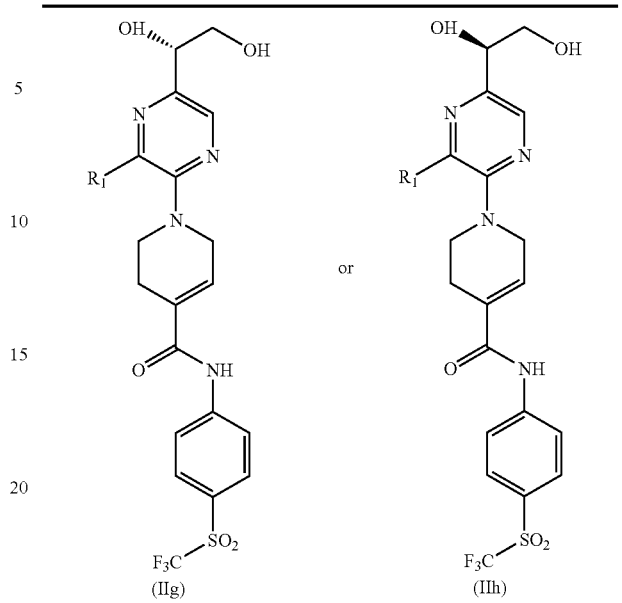

(IIg)     (IIh)

and pharmaceutically acceptable derivatives thereof, where:

| Compound | Formula | $R_1$ |
|---|---|---|
| HH2 | IIh | —F |
| HH3 | IIh | —$CF_3$ |

TABLE 5

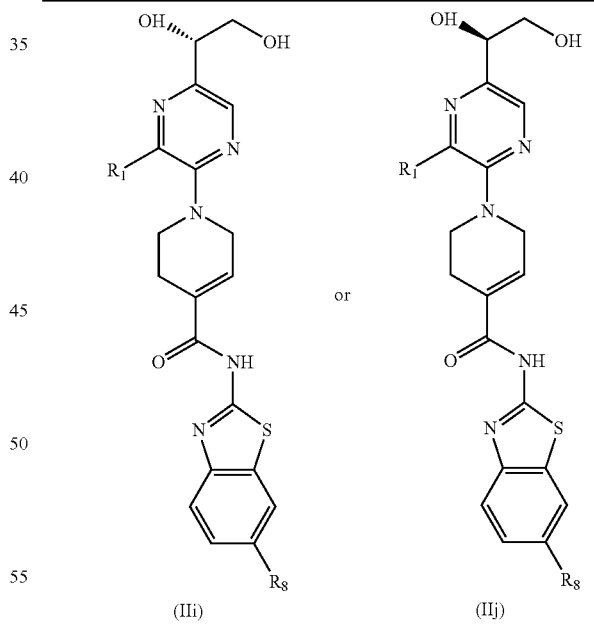

(IIi)     (IIj)

and pharmaceutically acceptable derivatives thereof, where:

| Compound | Formula | $R_1$ | $R_8$ |
|---|---|---|---|
| II1 | IIi | —Cl | —Cl |
| II2 | IIi | —Cl | —F |
| II3 | IIi | —Cl | —$CH_3$ |
| II4 | IIi | —F | —Cl |
| II5 | IIi | —F | —F |
| II6 | IIi | —F | —$CH_3$ |
| II7 | IIi | —$CF_3$ | —Cl |
| II8 | IIi | —$CF_3$ | —F |

TABLE 5-continued

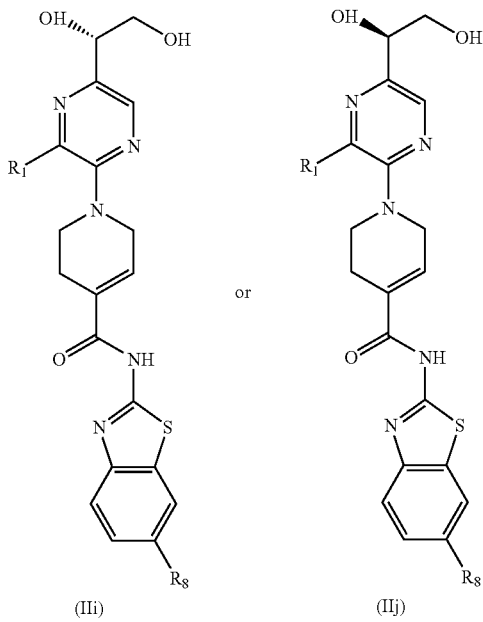

and pharmaceutically acceptable derivatives thereof, where:

| Compound | Formula | $R_1$ | $R_8$ |
|---|---|---|---|
| II9 | IIi | —$CF_3$ | —$CH_3$ |
| JJ1 | IIj | —Cl | —Cl |
| JJ2 | IIj | —Cl | —F |
| JJ3 | IIj | —Cl | —$CH_3$ |
| JJ4 | IIj | —F | —Cl |
| JJ5 | IIj | —F | —F |
| JJ6 | IIj | —F | —$CH_3$ |
| JJ7 | IIj | —$CF_3$ | —Cl |
| JJ8 | IIj | —$CF_3$ | —F |
| JJ9 | IIj | —$CF_3$ | —$CH_3$ |

TABLE 6

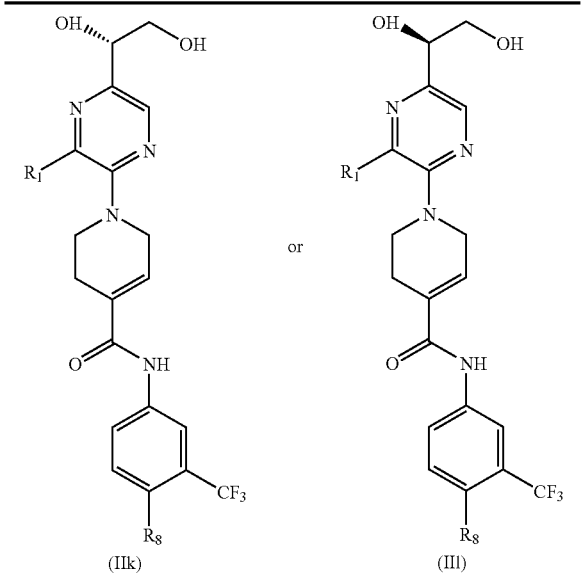

and pharmaceutically acceptable derivatives thereof, where:

| Compound | Formula | $R_1$ | $R_8$ |
|---|---|---|---|
| KK1 | IIk | —Cl | —Cl |
| KK2 | IIk | —Cl | —F |
| KK3 | IIk | —Cl | —Br |
| KK4 | IIk | —Cl | —$OCH_3$ |
| KK5 | IIk | —Cl | —$OCH_2CH_3$ |
| KK6 | IIk | —F | —Cl |
| KK7 | IIk | —F | —F |
| KK8 | IIk | —F | —Br |
| KK9 | IIk | —F | —$OCH_3$ |
| KK10 | IIk | —F | —$OCH_2CH_3$ |
| KK11 | IIk | —$CF_3$ | —Cl |
| KK12 | IIk | —$CF_3$ | —F |
| KK13 | IIk | —$CF_3$ | —Br |
| KK14 | IIk | —$CF_3$ | —$OCH_3$ |
| KK15 | IIk | —$CF_3$ | —$OCH_2CH_3$ |
| LL1 | III | —Cl | —Cl |
| LL2 | III | —Cl | —F |
| LL3 | III | —Cl | —Br |
| LL4 | III | —Cl | —$OCH_3$ |
| LL5 | III | —Cl | —$OCH_2CH_3$ |
| LL6 | III | —F | —Cl |
| LL7 | III | —F | —F |
| LL8 | III | —F | —Br |
| LL9 | III | —F | —$OCH_3$ |
| LL10 | III | —F | —$OCH_2CH_3$ |
| LL11 | III | —$CF_3$ | —Cl |
| LL12 | III | —$CF_3$ | —F |
| LL13 | III | —$CF_3$ | —Br |
| LL14 | III | —$CF_3$ | —$OCH_3$ |
| LL15 | III | —$CF_3$ | —$OCH_2CH_3$ |

In certain embodiments, compounds of Formula II are highly soluble in aqueous solutions at either pH 6.8 or pH 1.2, are very potent at the TRPV1 receptor, are expected to have good bioavailability, and are believed to have a good therapeutic index.

Compounds of Formula (III)

The invention further encompasses compounds of Formula (III):

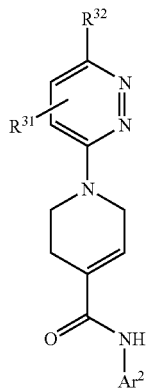
(III)

or a pharmaceutically acceptable derivative thereof, wherein:

$Ar^2$ is

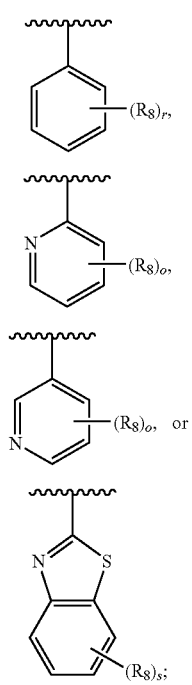

$R^{31}$ is hydrogen, halo, methyl, trihalomethyl, dihalomethyl, or halomethyl;

$R^{32}$ is

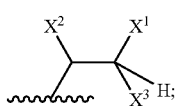

wherein each of $X^1$, $X^2$, and $X^3$ is independently hydroxy, alkyl, amino, or alkoxy, provided that at least one of $X^1$, $X^2$, or $X^3$ is hydroxy;

each $R_8$ is one or more of hydrogen, halo, $(C_1$-$C_6)$alkyl, $C(halo)_3$, $CH(halo)_2$, $CH_2(halo)$, $OC(halo)_3$, $OCH(halo)_2$, $OR_7$, $SC(halo)_3$, $OCH_2(halo)$, $SO_2C(halo)_3$, or $SO_2CH(halo)_2$; and each of o, r, and s is 1 or 2. Alternatively, each of each of o, r, and s is 0.

In one embodiment, a compound of Formula III is a pharmaceutically acceptable derivative of a compound of Formula III.

In another embodiment, a compound of Formula III is a compound of Formula III wherein the derivative is a pharmaceutically acceptable salt.

In another embodiment, a compound of Formula III is a pharmaceutically acceptable salt of a compound of Formula III.

In another embodiment, $R^{32}$ is an alkyl group substituted with at least one hydroxy group, preferably two hydroxy groups.

In another embodiment, $R^{32}$ is

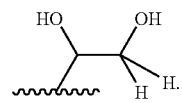

In another embodiment, $R^{32}$ is

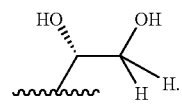

In another embodiment, $R_2$ is

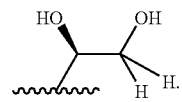

In another embodiment, $Ar^2$ is

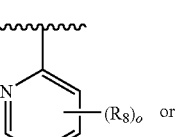

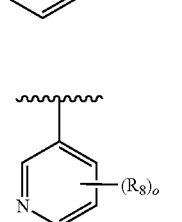

and each of o is 1, or 2; and $R_8$ is hydrogen, halo, trihalomethyl, or trihalomethoxy.

In another embodiment, $Ar^2$ is

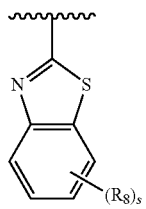

(e)

s is 1, or 2; and $R_8$ is hydrogen, halo, trihalomethyl, or trihalomethoxy.

In another embodiment, $R^{31}$ is halo, $CH_3$, $C(halo)_3$, $CH(halo)_2$, $CH_2(halo)$, or $OC(halo)_3$.

In certain embodiments, compounds of Formula III are highly soluble in aqueous solutions at either pH 6.8 or pH 1.2, are very potent at the TRPV1 receptor, are expected to have good bioavailability, and are believed to have a good therapeutic index.

Compounds of Formula (IV)

The invention further encompasses compounds of Formula (IV):

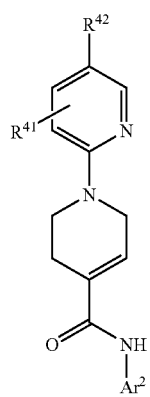

(IV)

or a pharmaceutically acceptable derivative thereof, wherein: $Ar^2$ is

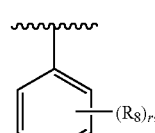

(a)

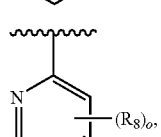

(b)

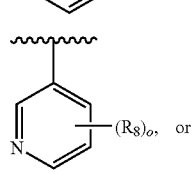

(c)

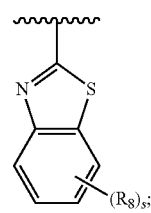

(e)

$R^{41}$ is hydrogen, halo, methyl, trihalomethyl, dihalomethyl, or halomethyl;

$R^{42}$ is

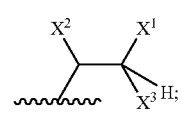

wherein each of $X^1$, $X^2$, and $X^3$ is independently hydroxy, alkyl, amino, or alkoxy, provided that at least one of $X^1$, $X^2$, or $X^3$ is hydroxy;

each $R_8$ is one or more of hydrogen, halo, $(C_1$-$C_6)$alkyl, $C(halo)_3$, $CH(halo)_2$, $CH_2(halo)$, $OC(halo)_3$, $OCH(halo)_2$, $OR_7$, $SC(halo)_3$, $OCH_2(halo)$, $SO_2C(halo)_3$, or $SO_2CH(halo)_2$; and each of o, r, and s is 1 or 2. Alternatively, each of each of o, r, and s is 0.

In one embodiment, a compound of Formula IV is a pharmaceutically acceptable derivative of a compound of Formula IV.

In another embodiment, a compound of Formula IV is a compound of Formula IV wherein the derivative is a pharmaceutically acceptable salt.

In another embodiment, a compound of Formula IV is a pharmaceutically acceptable salt of a compound of Formula IV.

In another embodiment, $R^{42}$ is an alkyl group substituted with at least one hydroxy group, preferably two hydroxy groups.

In another embodiment, $R^{42}$ is

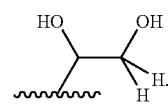

In another embodiment, $R^{42}$ is

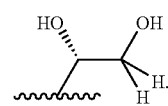

In another embodiment, $R_2$ is

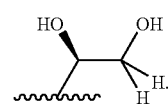

In another embodiment, Ar² is

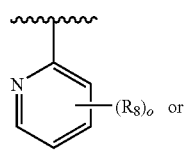
(b)

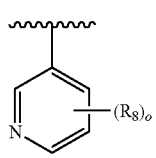
(c)

and each of o is 1, or 2; and R₈ is hydrogen, halo, trihalomethyl, or trihalomethoxy.

In another embodiment, Ar² is

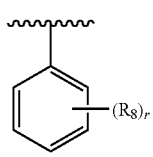

r is 1, or 2; and R₈ is hydrogen, halo, trihalomethyl, or trihalomethoxy.

In another embodiment, Ar² is

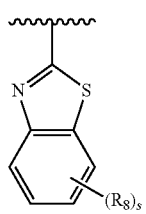
(e)

s is 1 or 2; and R₈ is hydrogen, halo, trihalomethyl, or trihalomethoxy.

In another embodiment, $R^{41}$ is halo, $CH_3$, $C(halo)_3$, $CH(halo)_2$, $CH_2(halo)$, or $OC(halo)_3$.

In certain embodiments, compounds of Formula IV are highly soluble in aqueous solutions at either pH 6.8 or pH 1.2, are very potent at the TRPV1 receptor, are expected to have good bioavailability, and are believed to have a good therapeutic index.

In another embodiment the compound of Formula IV is

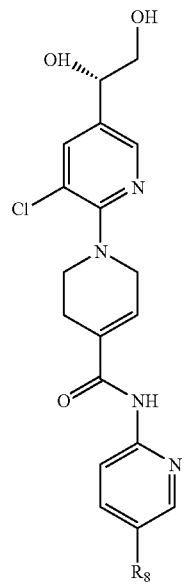

or a pharmaceutically acceptable derivative thereof, where R₈ is as defined above for the compounds of Formula I.

In another embodiment the compound of Formula IV is

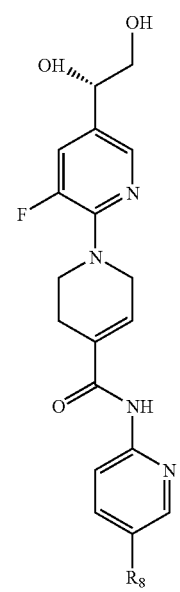

or a pharmaceutically acceptable derivative thereof, where R₈ is as defined above for the compounds of Formula I.

In another embodiment the compound of Formula IV is

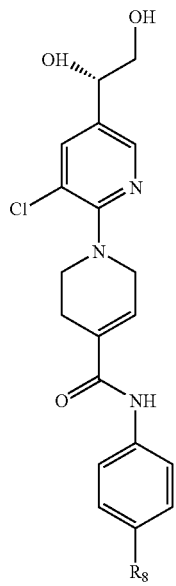

or a pharmaceutically acceptable derivative thereof, where R$_8$ is as defined above for the compounds of Formula I.

In another embodiment the compound of Formula IV is

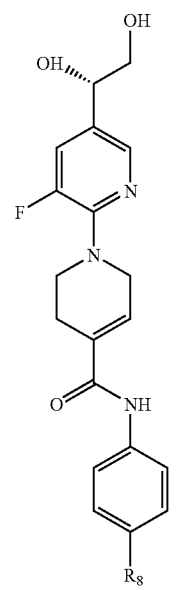

or a pharmaceutically acceptable derivative thereof, where R$_8$ is as defined above for the compounds of Formula I.

In another embodiment the compound of Formula IV is

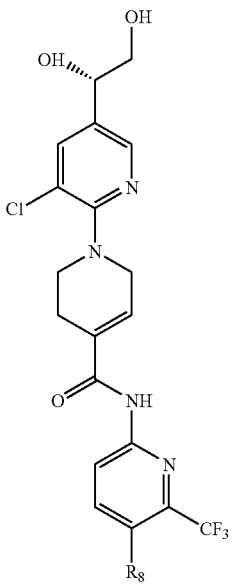

or a pharmaceutically acceptable derivative thereof, where R$_8$ is as defined above for the compounds of Formula I.

In another embodiment the compound of Formula IV is

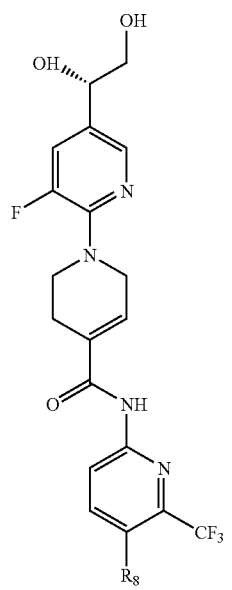

or a pharmaceutically acceptable derivative thereof, where R$_8$ is as defined above for the compounds of Formula I.

In another embodiment the compound of Formula IV is

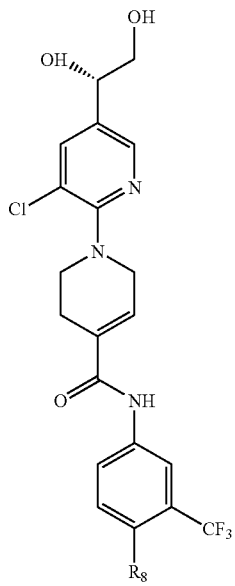

or a pharmaceutically acceptable derivative thereof, where $R_8$ is as defined above for the compounds of Formula I.

In another embodiment the compound of Formula IV is

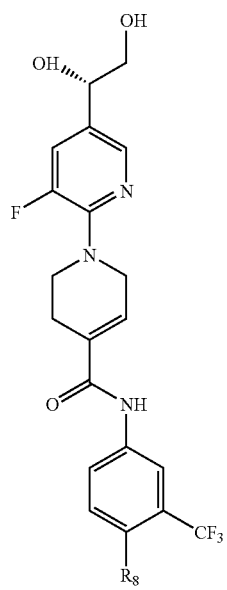

or a pharmaceutically acceptable derivative thereof, where $R_8$ is as defined above for the compounds of Formula I.

In another embodiment the compound of Formula IV is

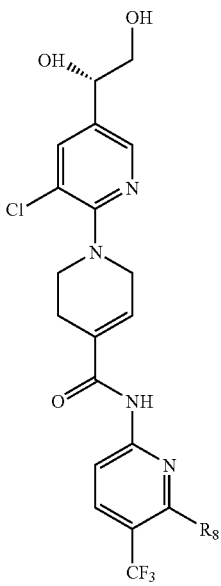

or a pharmaceutically acceptable derivative thereof, where $R_8$ is as defined above for the compounds of Formula I.

In another embodiment the compound of Formula IV is

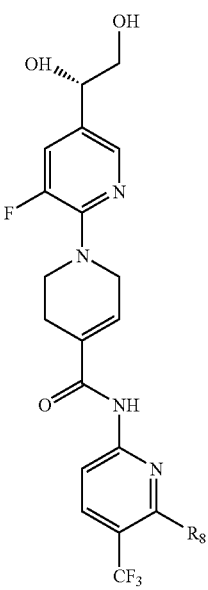

or a pharmaceutically acceptable derivative thereof, where $R_8$ is as defined above for the compounds of Formula I.

In another embodiment the compound of Formula IV is

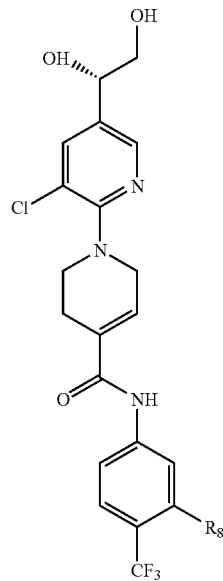

or a pharmaceutically acceptable derivative thereof, where $R_8$ is as defined above for the compounds of Formula I.

In another embodiment the compound of Formula IV is

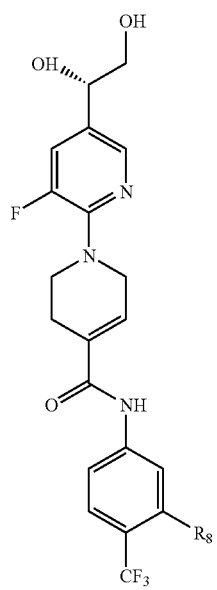

or a pharmaceutically acceptable derivative thereof, where $R_8$ is as defined above for the compounds of Formula I.

In another embodiment the compound of Formula IV is

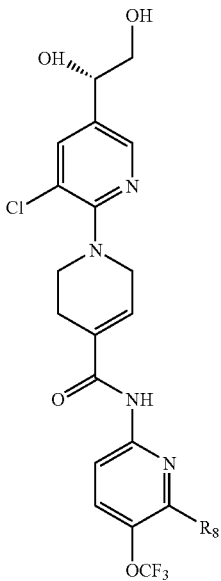

or a pharmaceutically acceptable derivative thereof, where $R_8$ is as defined above for the compounds of Formula I.

In another embodiment the compound of Formula IV is

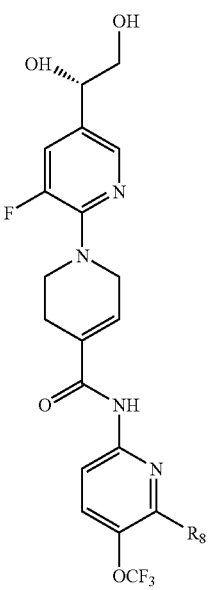

or a pharmaceutically acceptable derivative thereof, where $R_8$ is as defined above for the compounds of Formula I.

In another embodiment the compound of Formula IV is

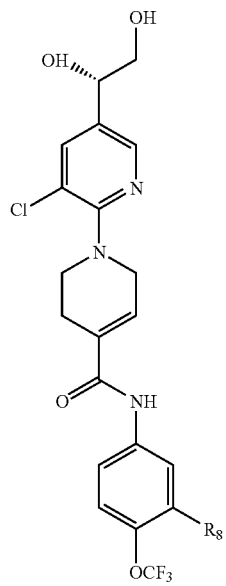

or a pharmaceutically acceptable derivative thereof, where $R_8$ is as defined above for the compounds of Formula I.

In another embodiment the compound of Formula IV is

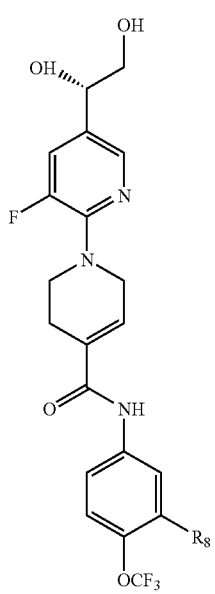

or a pharmaceutically acceptable derivative thereof, where $R_8$ is as defined above for the compounds of Formula I.

Illustrative compounds of Formula IV are listed below in Tables 7-18:

TABLE 7

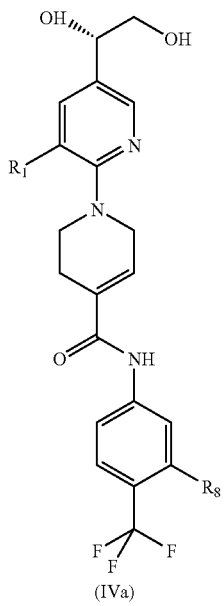

(IVa)

and pharmaceutically acceptable derivatives thereof, where:

| Compound | $R_1$ | $R_8$ |
|---|---|---|
| A1 | —Cl | —Cl |
| A2 | —Cl | —F |
| A3 | —Cl | —OCH$_3$ |
| A4 | —Cl | —OCH$_2$CH$_3$ |
| A5 | —F | —Cl |
| A6 | —F | —F |
| A7 | —F | —OCH$_3$ |
| A8 | —F | —OCH$_2$CH$_3$ |
| A9 | —CF$_3$ | —Cl |
| A10 | —CF$_3$ | —F |
| A11 | —CF$_3$ | —OCH$_3$ |
| A12 | —CF$_3$ | —OCH$_2$CH$_3$ |
| A13 | —Cl | —H |
| A14 | —F | —H |
| A15 | —CF$_3$ | —H |

TABLE 8

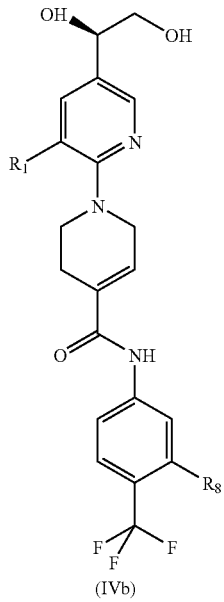

(IVb)

and pharmaceutically acceptable derivatives thereof, where:

| Compound | R₁ | R₈ |
| --- | --- | --- |
| B1 | —Cl | —Cl |
| B2 | —Cl | —F |
| B3 | —Cl | —OCH₃ |
| B4 | —Cl | —OCH₂CH₃ |
| B5 | —F | —Cl |
| B6 | —F | —F |
| B7 | —F | —OCH₃ |
| B8 | —F | —OCH₂CH₃ |
| B9 | —CF₃ | —Cl |
| B10 | —CF₃ | —F |
| B11 | —CF₃ | —OCH₃ |
| B12 | —CF₃ | —OCH₂CH₃ |
| B13 | —Cl | —H |
| B14 | —F | —H |
| B15 | —CF₃ | —H |

TABLE 9

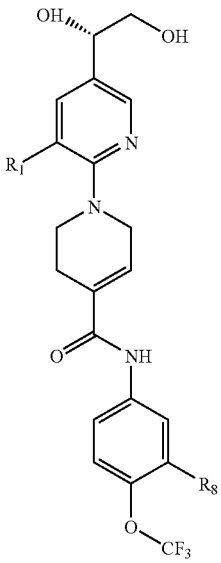

(IVc)

and pharmaceutically acceptable derivatives thereof, where:

| Compound | R₁ | R₈ |
| --- | --- | --- |
| C1 | —Cl | —CH₃ |
| C2 | —Cl | —CH₂CH₃ |
| C3 | —Cl | —Cl |
| C4 | —F | —CH₃ |
| C5 | —F | —CH₂CH₃ |
| C6 | —F | —Cl |
| C7 | —CF₃ | —CH₃ |
| C8 | —CF₃ | —CH₂CH₃ |
| C9 | —CF₃ | —Cl |
| C10 | —Cl | —H |
| C11 | —F | —H |
| C12 | —CF₃ | —H |

TABLE 10

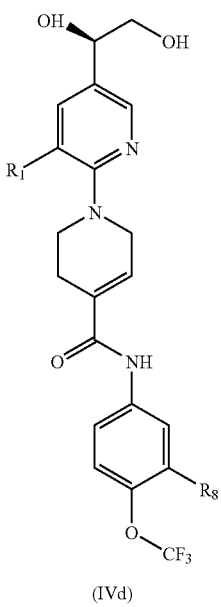

(IVd)

and pharmaceutically acceptable derivatives thereof, where:

| Compound | $R_1$ | $R_8$ |
|---|---|---|
| D1 | —Cl | —CH$_3$ |
| D2 | —Cl | —CH$_2$CH$_3$ |
| D3 | —Cl | —Cl |
| D4 | —F | —CH$_3$ |
| D5 | —F | —CH$_2$CH$_3$ |
| D6 | —F | —Cl |
| D7 | —CF$_3$ | —CH$_3$ |
| D8 | —CF$_3$ | —CH$_2$CH$_3$ |
| D9 | —CF$_3$ | —Cl |
| D10 | —Cl | —H |
| D11 | —F | —H |
| D12 | —CF$_3$ | —H |

TABLE 11

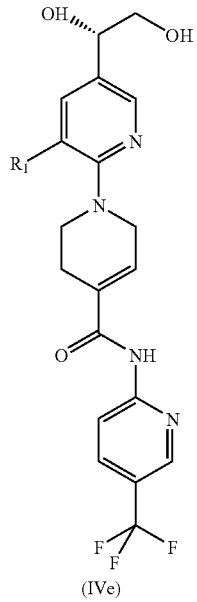

(IVe)

and pharmaceutically acceptable derivatives thereof, where:

| Compound | $R_1$ |
|---|---|
| E1 | —Cl |
| E2 | —F |
| E3 | —CF$_3$ |

TABLE 12

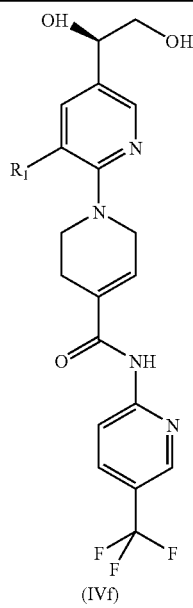

(IVf)

and pharmaceutically acceptable derivatives thereof, where:

| Compound | $R_1$ |
|---|---|
| F1 | —Cl |
| F2 | —F |
| F3 | —CF$_3$ |

TABLE 13

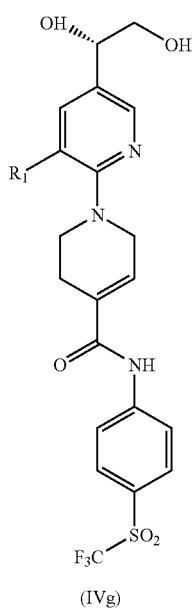

(IVg)

and pharmaceutically acceptable derivatives thereof, where:

| Compound | R₁ |
|---|---|
| G1 | —Cl |
| G2 | —F |
| G3 | —CF₃ |

TABLE 14

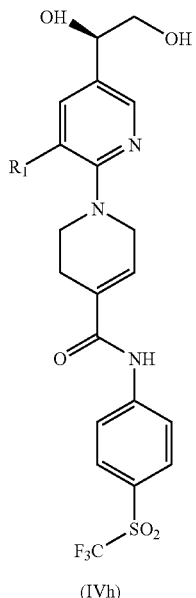

(IVh)

and pharmaceutically acceptable derivatives thereof, where:

| Compound | R₁ |
|---|---|
| H1 | —Cl |
| H2 | —F |
| H3 | —CF₃ |

TABLE 15

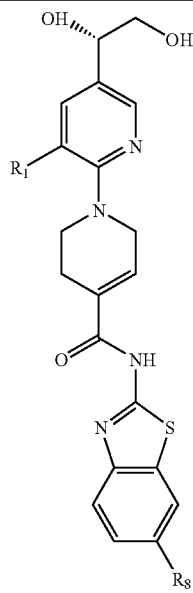

(IVi)

and pharmaceutically acceptable derivatives thereof, where:

| Compound | R₁ | R₈ |
|---|---|---|
| I1 | —Cl | —Cl |
| I2 | —Cl | —F |
| I3 | —Cl | —CH₃ |
| I4 | —F | —Cl |
| I5 | —F | —F |
| I6 | —F | —CH₃ |
| I7 | —CF₃ | —Cl |
| I8 | —CF₃ | —F |
| I9 | —CF₃ | —CH₃ |

TABLE 16

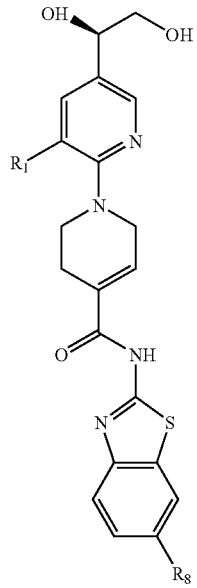

(IVj)

and pharmaceutically acceptable derivatives thereof, where:

| Compound | R₁ | R₈ |
|---|---|---|
| J1 | —Cl | —Cl |
| J2 | —Cl | —F |

TABLE 16-continued

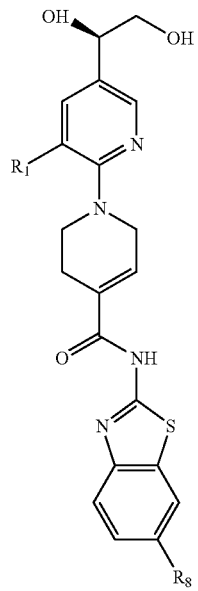

(IVj)

and pharmaceutically acceptable derivatives thereof, where:

| Compound | $R_1$ | $R_8$ |
|---|---|---|
| J3 | —Cl | —CH₃ |
| J4 | —F | —Cl |
| J5 | —F | —F |
| J6 | —F | —CH₃ |
| J7 | —CF₃ | —Cl |
| J8 | —CF₃ | —F |
| J9 | —CF₃ | —CH₃ |

TABLE 17

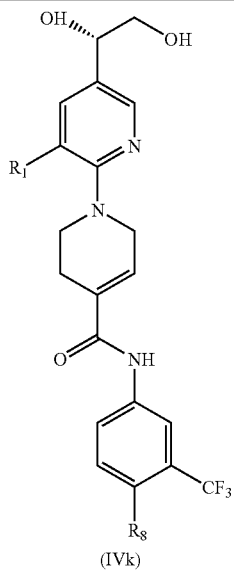

(IVk)

and pharmaceutically acceptable derivatives thereof, where:

| Compound | $R_1$ | $R_8$ |
|---|---|---|
| K1 | —Cl | —Cl |
| K2 | —Cl | —F |
| K3 | —Cl | —Br |
| K4 | —Cl | —OCH₃ |

TABLE 17-continued

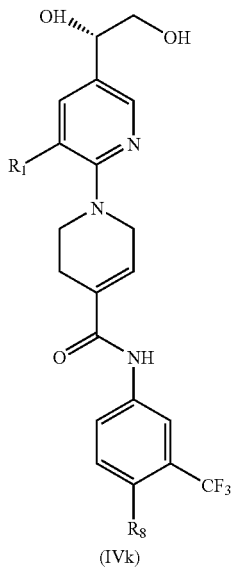

(IVk)

and pharmaceutically acceptable derivatives thereof, where:

| Compound | $R_1$ | $R_8$ |
|---|---|---|
| K5 | —Cl | —OCH₂CH₃ |
| K6 | —F | —Cl |
| K7 | —F | —F |
| K8 | —F | —Br |
| K9 | —F | —OCH₃ |
| K10 | —F | —OCH₂CH₃ |
| K11 | —CF₃ | —Cl |
| K12 | —CF₃ | —F |
| K13 | —CF₃ | —Br |
| K14 | —CF₃ | —OCH₃ |
| K15 | —CF₃ | —OCH₂CH₃ |

TABLE 18

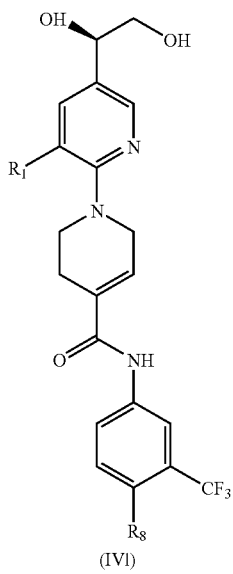

(IVl)

and pharmaceutically acceptable derivatives thereof, where:

| Compound | $R_1$ | $R_8$ |
|---|---|---|
| L1 | —Cl | —Cl |
| L2 | —Cl | —F |

TABLE 18-continued

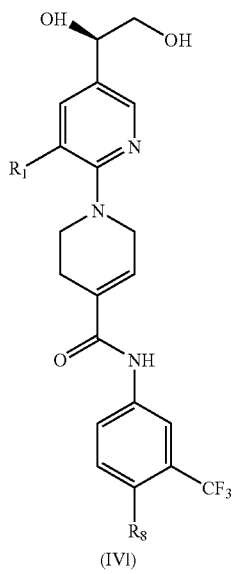

(IVl)

and pharmaceutically acceptable derivatives thereof, where:

| Compound | R$_1$ | R$_8$ |
|---|---|---|
| L3 | —Cl | —Br |
| L4 | —Cl | —OCH$_3$ |
| L5 | —Cl | —OCH$_2$CH$_3$ |
| L6 | —F | —Cl |
| L7 | —F | —F |
| L8 | —F | —Br |
| L9 | —F | —OCH$_3$ |
| L10 | —F | —OCH$_2$CH$_3$ |
| L11 | —CF$_3$ | —Cl |
| L12 | —CF$_3$ | —F |
| L13 | —CF$_3$ | —Br |
| L14 | —CF$_3$ | —OCH$_3$ |
| L15 | —CF$_3$ | —OCH$_2$CH$_3$ |

Compounds of Formula (V)

The invention further encompasses compounds of Formula (V):

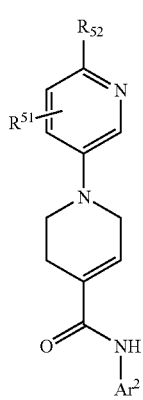

(V)

or a pharmaceutically acceptable salt thereof, wherein:

Ar$^2$ is

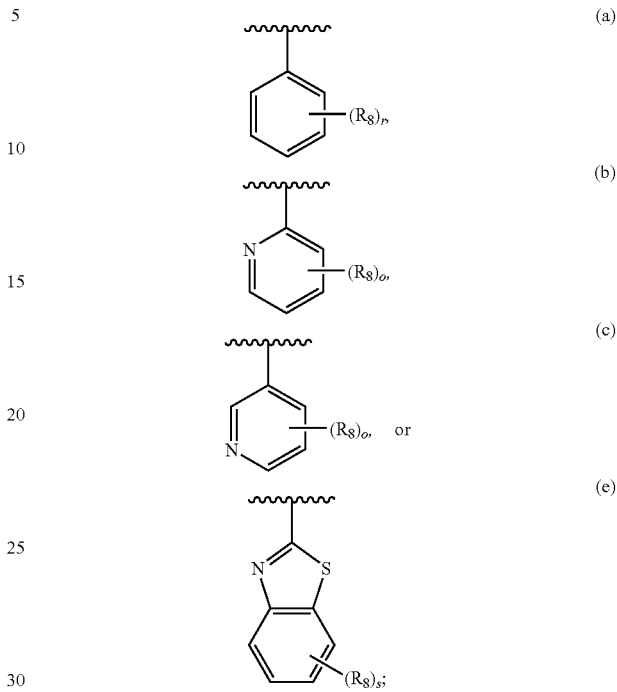

$R^{51}$ is hydrogen, halo, methyl, trihalomethyl, dihalomethyl, or halomethyl;

$R^{52}$ is

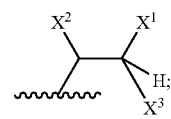

wherein each of $X^1$, $X^2$, and $X^3$ is independently hydroxy, alkyl, amino, or alkoxy, provided that at least one of $X^1$, $X^2$, or $X^3$ is hydroxy;

each R$_8$ is one or more of hydrogen, halo, (C$_1$-C$_6$)alkyl, C(halo)$_3$, CH(halo)$_2$, CH$_2$(halo), OC(halo)$_3$, OCH(halo)$_2$, OR$_7$, SC(halo)$_3$, OCH$_2$(halo), SO$_2$C(halo)$_3$, or SO$_2$CH(halo)$_2$; and each of o, r, and s is 1 or 2. Alternatively, each of each of o, r, and s is 0.

In one embodiment, a compound of Formula V is a pharmaceutically acceptable derivative of a compound of Formula V.

In another embodiment, a compound of Formula V is a compound of Formula V wherein the derivative is a pharmaceutically acceptable salt.

In another embodiment, a compound of Formula V is a pharmaceutically acceptable salt of a compound of Formula V.

In another embodiment, $R^{52}$ is an alkyl group substituted with at least one hydroxy group, preferably two hydroxy groups.

In another embodiment, $R^{52}$ is CH(OH)CH$_2$OH, CH(OH)CHOHCH$_3$, or CH(CH$_2$OH)$_2$.

In another embodiment, $R^{52}$ is

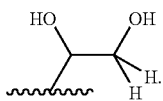

In another embodiment, $R^{52}$ is

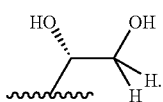

In another embodiment, $R_2$ is

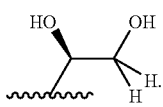

In another embodiment, $Ar^2$ is

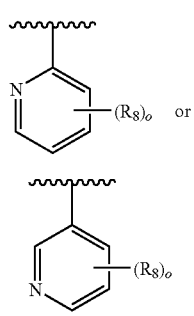

and each of o is 1, or 2; and $R_8$ is hydrogen, halo, trihalomethyl, or trihalomethoxy.

In another embodiment, $Ar^2$ is

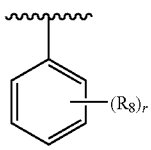

where r is 1 or 2; $R_8$ is hydrogen, halo, trihalomethyl, or trihalomethoxy.

In another embodiment, $Ar^2$ is

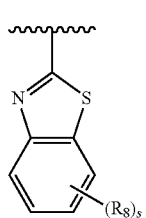

s is 1, or 2; $R_8$ is hydrogen, halo, trihalomethyl, or trihalomethoxy.

In another embodiment, $R^{51}$ is halo, $CH_3$, $C(halo)_3$, $CH(halo)_2$, $CH_2(halo)$, or $OC(halo)_3$.

In certain embodiments, compounds of Formula V are highly soluble in aqueous solutions at either pH 6.8 or pH 1.2, are very potent at the TRPV1 receptor, are expected to have good bioavailability, and are believed to have a good therapeutic index.

DEFINITIONS

As used in connection with the compounds of Formulae (I)-(V) herein, the terms used above having following meaning:

"$(C_1-C_{10})$alkyl" means a straight chain or branched non-cyclic hydrocarbon having from 1 to 10 carbon atoms. Representative straight chain $(C_1-C_{10})$alkyls include methyl, ethyl, n-propyl, n-butyl, n-pentyl, n-hexyl, n-heptyl, n-octyl, n-nonyl, and n-decyl. Representative branched $(C_1-C_{10})$ alkyls include iso-propyl, sec-butyl, iso-butyl, tert-butyl, iso-pentyl, neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"$(C_1-C_6)$alkyl" means a straight chain or branched non-cyclic hydrocarbon having from 1 to 6 carbon atoms. Representative straight chain $(C_1-C_6)$alkyls include methyl, ethyl, n-propyl, n-butyl, n-pentyl, and n-hexyl. Representative branched $(C_1-C_6)$alkyls include iso-propyl, sec-butyl, iso-butyl, tert-butyl, iso-pentyl, neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"$(C_1-C_4)$alkyl" means a straight chain or branched non-cyclic hydrocarbon having from 1 to 4 carbon atoms. Representative straight chain $(C_1-C_4)$alkyls include methyl, ethyl, n-propyl, and n-butyl. Representative branched $(C_1-C_4)$ alkyls include iso-propyl, sec-butyl, iso-butyl, and tert-butyl.

"$(C_1-C_6)$haloalkyl" means a straight chain or branched non-cyclic hydrocarbon having from 1 to 6 carbon atoms as defined above for $(C_1-C_6)$alkyl that is substituted with 1, 2 or 3 independently selected halo groups, for example, $C(halo)_3$, $CH(halo)_2$, $CH_2(halo)$, $CH_2CH(halo)_2$, etc.

"$(C_1-C_6)$hydroxyalkyl" means a straight chain or branched non-cyclic hydrocarbon having from 1 to 6 carbon atoms as defined above for $(C_1-C_6)$alkyl that is substituted with 1, 2 or 3 hydroxyl groups.

"$(C_2-C_{10})$alkenyl" means a straight chain or branched non-cyclic hydrocarbon having from 2 to 10 carbon atoms and including at least one carbon-carbon double bond. Representative straight chain and branched $(C_2-C_{10})$alkenyls include vinyl, allyl, 1-butenyl, 2-butenyl, iso-butylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like.

"($C_2$-$C_6$)alkenyl" means a straight chain or branched non-cyclic hydrocarbon having from 2 to 6 carbon atoms and including at least one carbon-carbon double bond. Representative straight chain and branched ($C_2$-$C_6$)alkenyls include vinyl, allyl, 1-butenyl, 2-butenyl, iso-butylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl and the like.

"($C_2$-$C_6$)haloalkenyl" means a straight chain or branched non-cyclic hydrocarbon having from 2 to 6 carbon atoms and including at least one carbon-carbon double bond as defined above for ($C_2$-$C_6$)alkenyl that is substituted with 1, 2 or 3 independently selected halo groups.

"($C_2$-$C_6$)haloalkynyl" means a straight chain or branched non-cyclic hydrocarbon having from 2 to 6 carbon atoms and including at least one carbon-carbon triple bond that is substituted with 1, 2 or 3 independently selected halo groups.

"($C_2$-$C_6$)hydroxyalkynyl" means a straight chain or branched non-cyclic hydrocarbon having from 2 to 6 carbon atoms and including at least one carbon-carbon triple bond that is substituted with 1, 2 or 3 hydroxyl groups.

"($C_1$-$C_6$)alkoxy" means a straight chain or branched non cyclic hydrocarbon having one or more ether groups and from 1 to 6 carbon atoms. Representative straight chain and branched ($C_1$-$C_6$)alkoxys include methoxy, ethoxy, propoxy, butoxy, pentoxy, hexoxy, methoxymethyl, 2-methoxyethyl, 5-methoxypentyl, 3-ethoxybutyl, and the like.

"($C_1$-$C_6$)alkoxy($C_2$-$C_6$)alkyl" means a straight chain or branched non cyclic hydrocarbon having one or more ether groups and from 1 to 6 carbon atoms as defined above for ($C_1$-$C_6$)alkoxy group that is substituted with a ($C_2$-$C_6$)alkyl group.

"($C_1$-$C_6$)alkoxy($C_2$-$C_6$)alkenyl" means a straight chain or branched non cyclic hydrocarbon having one or more ether groups and from 1 to 6 carbon atoms as defined above for ($C_1$-$C_6$)alkoxy group that is substituted with a ($C_2$-$C_6$)alkenyl group.

"($C_1$-$C_6$)alkoxy($C_2$-$C_6$)alkynyl" means a straight chain or branched non cyclic hydrocarbon having one or more ether groups and from 1 to 6 carbon atoms that is substituted with a ($C_2$-$C_6$)alkynyl group.

"($C_1$-$C_6$)alkoxy($C_3$-$C_8$)cycloalkyl" means a straight chain or branched non cyclic hydrocarbon having one or more ether groups and from 1 to 6 carbon atoms as defined above for ($C_1$-$C_6$)alkyl group that is substituted with a ($C_3$-$C_8$)cycloalkyl group "($C_2$-$C_6$)hydroxyalkenyl" means a straight chain or branched non-cyclic hydrocarbon having from 2 to 6 carbon atoms and including at least one carbon-carbon double bond as defined above for ($C_2$-$C_6$)alkenyl that is substituted with 1, 2 or 3 hydroxyl groups.

"($C_2$-$C_{10}$)alkynyl" means a straight chain or branched non-cyclic hydrocarbon having from 2 to 10 carbon atoms and including at least one carbon-carbon triple bond. Representative straight chain and branched ($C_2$-$C_{10}$)alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like.

"($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl and the like.

"($C_3$-$C_{10}$)cycloalkyl" means a saturated cyclic hydrocarbon having from 3 to 10 carbon atoms. Representative ($C_3$-$C_{10}$)cycloalkyls are cyclopropyl, cyclobutyl, cyclopentyl, cyclohexyl, cycloheptyl, cyclooctyl, cyclononyl, and cyclodecyl.

"($C_3$-$C_8$)cycloalkyl" means a saturated cyclic hydrocarbon having from 3 to 8 carbon atoms. Representative ($C_3$-$C_8$) cycloalkyls include cyclopropyl, cyclobutyl, cyclopentyl, cyclohexyl, cycloheptyl, and cyclooctyl.

"($C_8$-$C_{14}$)bicycloalkyl" means a bi-cyclic hydrocarbon ring system having from 8 to 14 carbon atoms and at least one saturated cyclic alkyl ring. Representative ($C_8$-$C_{14}$)bicycloalkyls include indanyl, 1,2,3,4-tetrahydronaphthyl, 5,6,7, 8-tetrahydronaphthyl, perhydronaphthyl and the like.

"($C_8$-$C_{14}$)tricycloalkyl" means a tri-cyclic hydrocarbon ring system having from 8 to 14 carbon atoms and at least one saturated ring. Representative ($C_8$-$C_{14}$)tricycloalkyls include pyrenyl, 1,2,3,4-tetrahydroanthracenyl, perhydroanthracenyl aceanthrenyl, 1,2,3,4-tetrahydropenanthrenyl, 5,6,7,8-tetrahydrophenanthrenyl, perhydrophenanthrenyl and the like.

"($C_5$-$C_{10}$)cycloalkenyl" means a cyclic non-aromatic hydrocarbon having at least one carbon-carbon double bond in the cyclic system and from 5 to 10 carbon atoms. Representative ($C_5$-$C_{10}$)cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

"($C_5$-$C_8$)cycloalkenyl" means a cyclic non-aromatic hydrocarbon having at least one carbon-carbon double bond in the cyclic system and from 5 to 8 carbon atoms. Representative ($C_5$-$C_8$)cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl and the like.

"($C_8$-$C_{14}$)bicycloalkenyl" means a bi-cyclic hydrocarbon ring system having at least one carbon-carbon double bond in each ring and from 8 to 14 carbon atoms. Representative ($C_8$-$C_{14}$)bicycloalkenyls include indenyl, pentalenyl, naphthalenyl, azulenyl, heptalenyl, 1,2,7,8-tetrahydronaphthalenyl and the like.

"($C_8$-$C_{14}$)tricycloalkenyl" means a tri-cyclic hydrocarbon ring system having at least one carbon-carbon double bond in each ring and from 8 to 14 carbon atoms. Representative ($C_8$-$C_{14}$)tricycloalkenyls include anthracenyl, phenanthrenyl, phenalenyl, acenaphthalenyl, as-indacenyl, s-indacenyl and the like.

"(3- to 7-membered)heterocycle" or "(3- to 7-membered) heterocyclo" means a 3- to 7-membered monocyclic heterocyclic ring which is either saturated, unsaturated non-aromatic, or aromatic. A 3- or a 4-membered heterocycle can contain up to 3 heteroatoms, a 5-membered heterocycle can contain up to 4 heteroatoms, a 6-membered heterocycle can contain up to 6 heteroatoms, and a 7-membered heterocycle can contain up to 7 heteroatoms. Each heteroatom is independently selected from nitrogen, which can be quaternized; oxygen; and sulfur, including sulfoxide and sulfone. The (3- to 7-membered)heterocycle can be attached via a nitrogen or carbon atom. Representative (3- to 7-membered)heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrimidinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"(3- to 5-membered)heterocycle" or "(3- to 5-membered) heterocyclo" means a 3- to 5-membered monocyclic heterocyclic ring which is either saturated, unsaturated non-aromatic, or aromatic. A 3- or a 4-membered heterocycle can contain up to 3 heteroatoms, and a 5-membered heterocycle can contain up to 4 heteroatoms. Each heteroatom is independently selected from nitrogen, which can be quaternized; oxygen; and sulfur, including sulfoxide and sulfone. The (3- to 5-membered)heterocycle can be attached via a nitrogen or carbon atom. Representative (3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"(7- to 10-membered)bicycloheterocycle" or "(7- to 10-membered)bicycloheterocyclo" means a 7- to 10-membered bicyclic, heterocyclic ring which is either saturated, unsaturated non-aromatic, or aromatic. A (7- to 10-membered)bicycloheterocycle contains from 1 to 4 heteroatoms independently selected from nitrogen, which can be quaternized; oxygen; and sulfur, including sulfoxide and sulfone. The (7- to 10-membered)bicycloheterocycle can be attached via a nitrogen or carbon atom. Representative (7- to 10-membered)bicycloheterocycles include quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl and the like.

"$(C_{14})$aryl" means a 14-membered aromatic carbocyclic moiety such as anthryl or phenanthryl.

"(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur. In one embodiment, one of the (5- to 10-membered)heteroaryl's rings contain at least one carbon atom. In another embodiment, both of the (5- to 10-membered)heteroaryl's rings contain at least one carbon atom. Representative (5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrimidinyl, thiadiazolyl, triazinyl, cinnolinyl, phthalazinyl, and quinazolinyl.

"$CH_2$(halo)" means a methyl group where one of the hydrogens of the methyl group has been replaced with a halogen. Representative $CH_2$(halo) groups include $CH_2F$, $CH_2Cl$, $CH_2Br$, and $CH_2I$.

"CH(halo)$_2$" means a methyl group where two of the hydrogens of the methyl group have been replaced with a halogen. Representative CH(halo)$_2$ groups include $CHF_2$, $CHCl_2$, $CHBr_2$, $CHBrCl$, $CHClI$, and $CHI_2$.

"C(halo)$_3$" means a methyl group where each of the hydrogens of the methyl group has been replaced with a halogen. Representative C(halo)$_3$ groups include $CF_3$, $CCl_3$, $CBr_3$, and $CI_3$.

"Halogen" or "halo" means F, Cl, Br, or I.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative," as used herein, includes any pharmaceutically acceptable salt, solvate, radiolabeled, stereoisomer, enantiomer, diastereomer, other stereoisomeric form, racemic mixture, geometric isomer, and/or tautomer, e.g., of a compound of Formula I-V of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a compound of Formula I-V of the invention. In another embodiment, the pharmaceutically acceptable derivative is a pharmaceutically acceptable salt, e.g., of a compound of Formula I of the invention.

The phrase "pharmaceutically acceptable salt," as used herein, is any pharmaceutically acceptable salt that can be prepared from a compound of Formulae (I)-(V), including a salt formed from an acid and a basic functional group, such as a nitrogen group, of one of the compounds of Formulae (I)-(V). Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of Formulae (I)-(V) having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine and the like.

The invention disclosed herein is also meant to encompass all prodrugs of the compounds of the invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a compound of Formula I-V which is readily convertible in vivo, e.g., by being metabolized, into the required compound of Formula I-V. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs*. 8:1-38 (1992); Bundgaard et al., *J. Pharmaceut. Sci.* 77:285 (1988); and Kakeya et al., *Chem. Pharm. Bull.* 32:692 (1984).

The phrase "effective amount," when used in connection with a compound of Formulae (I)-(V) means an amount effective for: (a) treating or preventing a Condition; or (b) inhibiting TRPV1 function in a cell.

The phrase "effective amount," when used in connection with the another therapeutic agent means an amount for providing the therapeutic effect of the therapeutic agent.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The term "ALS" means amyotrophic lateral sclerosis.

The term "LiHMDS" means lithium hexamethyldisilazide.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

The invention disclosed herein is also meant to encompass prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Some of the compounds disclosed herein may contain one or more asymmetric centers and may thus give rise to enantiomers, diastereomers, and other stereoisomeric forms. The present invention is also meant to encompass all such possible forms, as well as their racemic and resolved forms and mixtures thereof. The individual enantiomers may be separated according to methods that are well known to those of ordinary skill in the art. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "enantiomerically enriched" refers to a mixture of enantiomers in which one of the enantiomers has been selectively synthesized through asymmetric synthesis or separated in preference over the other enantiomer. Asymmetric synthesis involves at least one enantioselective step whereby one of the two enantiomers is preferentially prepared. Alternatively, a mixture of two enantiomers (e.g., a racemic mixture or a mixture with an enantiomeric excess lower than the desired level) may be enriched in one of the two enantiomers using a separation technique, e.g., chiral chromatography. Thus an "enantiomerically enriched" product will have an enantiomeric excess (i.e., % ee), in which one enantiomer is present in an amount larger than the other. Thus, "enantiomerically enriched" refers to having an enantiomeric excess of more than 0% but less than 100%. "Enantiomeric excess" is equal to 100 times the mole fraction of the major enantiomer minus the more fraction of the minor enantiomer. Thus, a racemate has a 0% ee while an enantiomerically pure product has 100% ee.

Certain embodiments of the invention include compounds and compositions wherein the enantiomer is present at an e.e. of greater than 50%, 60%, 70%, 80%, 90%, 95%, or 99%.

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The invention disclosed is also meant to encompass all pharmaceutically acceptable salts thereof of the disclosed compounds. Examples of pharmaceutically acceptable addition salts include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, aspartginate, glutamate and the like.

Examples of prodrugs include esters or amides of Formulae (I)-(V) with any of $R_2$-$R_8$ as hydroxyalkyl or aminoalkyl, and these may be prepared by reacting such compounds with anhydrides such as succinic anhydride.

Methods for Making the Compounds of Formulae (I)-(V)

The compounds of Formulae (I)-(V) can be made using conventional organic synthesis or by the following illustrative methods shown in the schemes below.

The compounds of Formulae (I)-(V) where X is O can be obtained by the following illustrative method shown below in Scheme 1.

Scheme 1

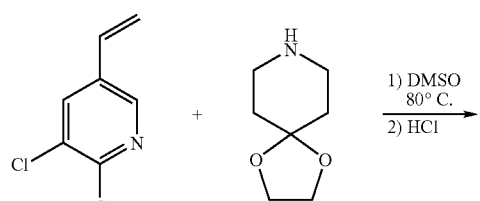

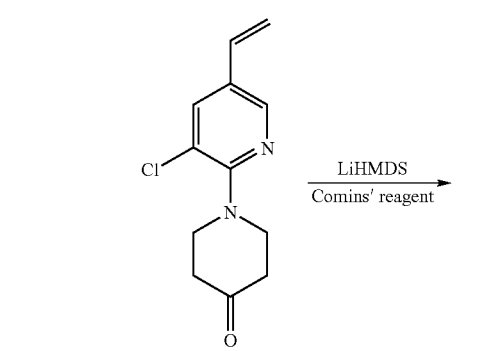

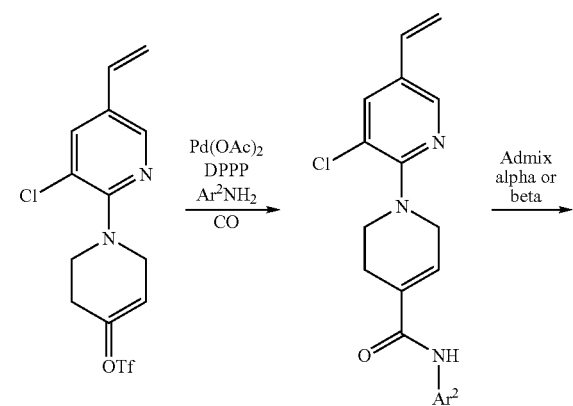

Preparation of 2,3-Dichloro-5-formylpyridine 2

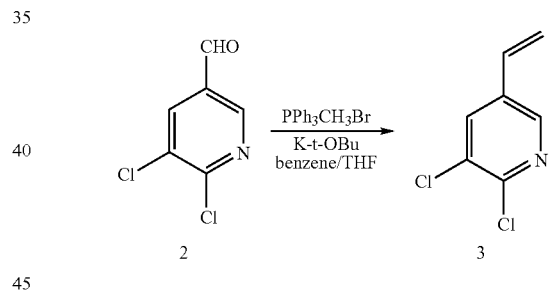

To a 500 mL round-bottom flask, manganese oxide (43.5 g, 0.50 mol) was added to a solution of 2,3-dichloro-5-hydroxylmethylpyridine (1, 8.10 g, 50.0 mMol) in anhydrous $CH_2Cl_2$ (150 mL). The resulting mixture was stirred at room temperature for 2 days, which was filtered through Celite and concentrated. The crude mixture was purified by a silica gel chromatography column eluting with a gradient of ethyl acetate (0-40%)/hexanes to give 7.2 g of the desired product 2 (90%). $^1$H NMR (400 MHz, $CDCl_3$) δ 10.08 (1H, s), 8.77 (1H, d, J=1.97 Hz), 8.25 (1H, d, J=1.97 Hz). LC/MS (M+1): 176.

Preparation of 2,3-Dichloro-5-vinylpyridine 3

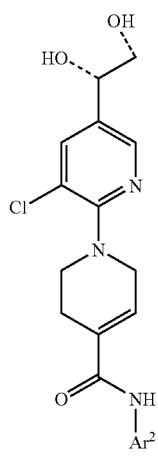

To a cooled 0° C., stirred slurry of methyltriphenylphosphonium bromide (10.0 g) in toluene (200 mL) was added potassium t-butoxide (3.07 g) portionwise to produce a yellow slurry. After 1 hr, the reaction mixture was cooled to −20° C. and 2,3-dichloro-5-formylpyridine (2, 4.0 grams, 22.72 mMol) which dissolved in tetrahydrofuran (6 mL) was added dropwise to produce a purple colored slurry. The reaction mixture was warmed to 0° C. and stirred for additional 1 hr. Then the reaction mixture was treated with saturated aqueous brine (150 mL) and diluted with ethyl acetate (200 mL). The resulting organic layer was washed with brine, dried over anhydrous sodium sulfate and concentrated in vacuo. The crude product was purified by silica gel chromatography column eluting with a gradient of ethyl acetate (0-10%)/hexanes to afford 2.77 g of the desired product 3 (70%). $^1$H NMR (400 MHz, $CDCl_3$) δ 8.30 (1H, d, J=2.19 Hz), 7.80 (1H, d, J=2.19 Hz), 6.63 (1H, dd, J=10.96, 17.80 Hz), 5.86 (1H, d, J=17.80 Hz), 5.45 (1H, d, J=10.96 Hz). LC/MS (M+1): 174.

Synthesis of Ketal 5

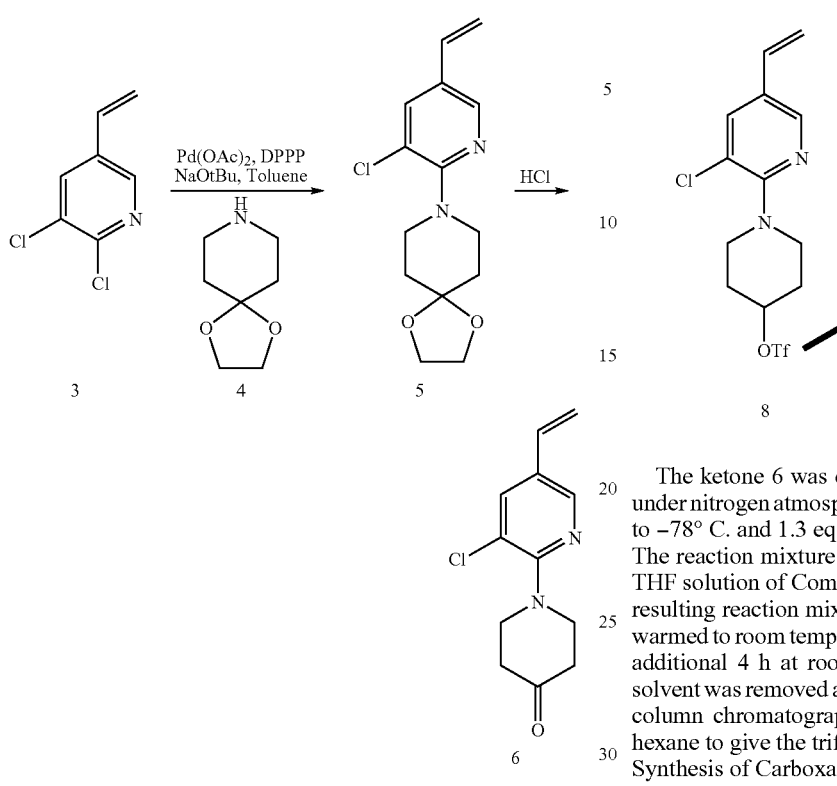

A 1.1 eq. portion of the piperidinyl ketal 4 was added to a solution of the 2,3-dichloro-4-vinyl-pyridine 3 in toluene, followed by 1.1 eq. NaOtBu, 0.05 eq. Pd(OAc)$_2$, and 0.05 eq. 1,3-bis(diphenylphosphino)propane (DPPP). The resulting solution was stirred with a magnetic stir bar and heated to 65° C. under nitrogen. The reaction mixture was stirred at this temperature for 3 h. The mixture was then cooled and filtered through Celite with EtOAc. The solution was concentrated and the residue was passed through a pad of silica gel with a solution of 50% EtOAc in hexane to give the desired ketal 5.

Synthesis of Ketone 6

Compound 5 was dissolved in THF and treated with and equal volume of 4N aq. HCl. The reaction mixture was stirred and heated to 60° C. for 3 h. The mixture was allowed to cool to r.t. The solution was then made basic with aq. K$_2$CO$_3$ and extracted with EtOAc, dried over Na$_2$SO$_4$, and concentrated to give ketone 6.

Synthesis of Triflate 8

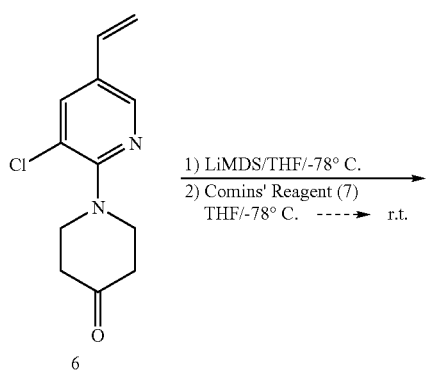

The ketone 6 was dissolved in THF at room temperature under nitrogen atmosphere. The resulting solution was cooled to −78° C. and 1.3 eq. of LiHMDS (1M in THF) was added. The reaction mixture was stirred at −78° C. for 1.5 h and a THF solution of Comins' reagent 7 (1.0 eq.) was added. The resulting reaction mixture was stirred at −78° C. for 1 h and warmed to room temperature over 1 h period and stirred for an additional 4 h at room temperature. After this period, the solvent was removed and the resulting residue was purified by column chromatography using a gradient of ethyl acetate/hexane to give the triflate 8.

Synthesis of Carboxamide 9

Compound 8, 2.0 eq of an aniline, and 2.2 eq. of triethylamine are dissolved in THF at room temperature under nitrogen atmosphere. The resulting solution was stirred for 2-10 min and 0.2 eq of Pd(OAc)$_2$ and 0.2 eq of DPPP are added. The reaction mixture was flushed with nitrogen gas. The reaction mixture was flushed with carbon monoxide gas. The resulting reaction mixture was stirred at 72° C. for 35 minutes. After this period, the solvent was removed and the resulting residue was purified by column chromatography using hexane and ethyl acetate gradient as eluent to give carboxamide 9.

Synthesis of Diol 10

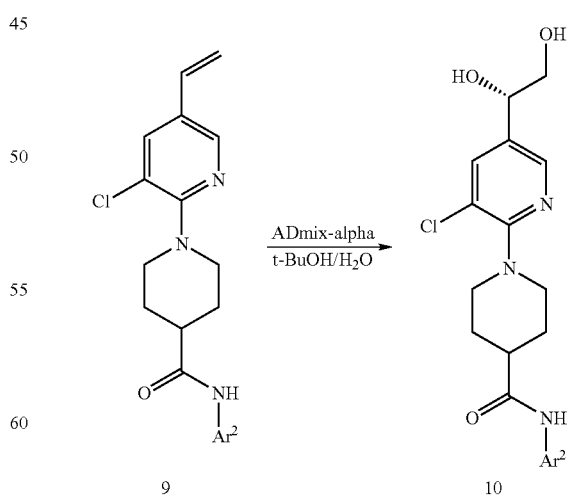

A 1 M t-butanol solution of vinylpyridine-carboxamide formed above 9 was added to a cooled (° C.) mixture of ADmix-α (1.34 gm ADmix-α for each mmol of vinylpyridine-carboxamide 9) in t-butanol and water (1:1 ratio). The reaction mixture was stirred for 24 hrs and sodium sulphite was added. The resulting slurry was allowed to stir at ambient temperature for 30 min. The mixture was extracted with ethyl acetate, the combined organic layers were washed with brine, dried over $Na_2SO_4$ and concentrated in vacuo. The resulting mixture was purified by a silica gel chromatography column eluting with ethyl acetate/hexanes gradient to afford the desired product 10.

Alternative Method for Preparing of
2,3-Dichloro-5-vinylpyridine 3

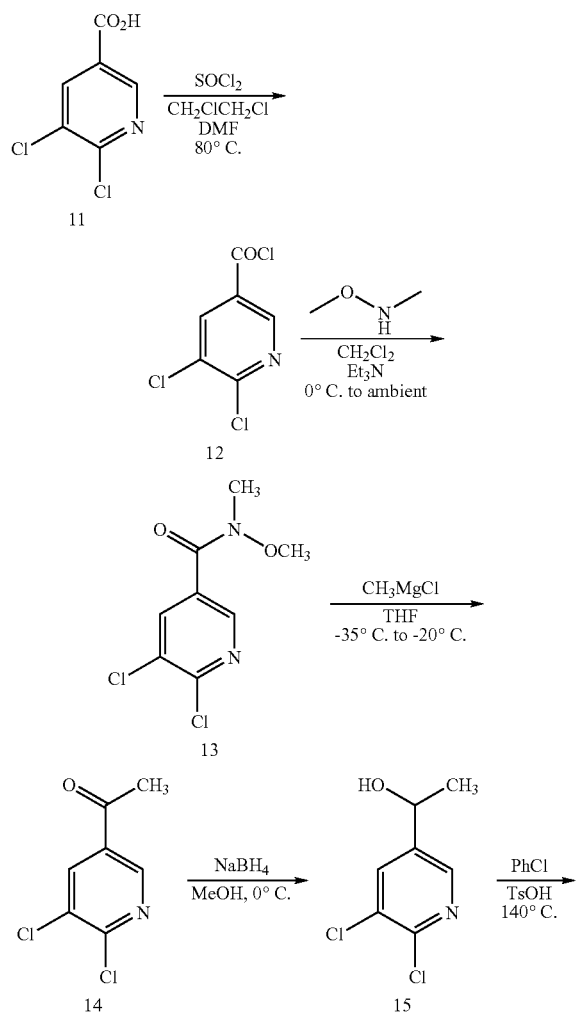

5,6-Dichloro-N-methoxy-N-methyl-nicotinamide 13

To a well stirred suspension of 5,6-dichloronicotinic acid 11 (600 g, 3.125 mole) and N,N-dimethylformamide (20.0 mL) in dichloroethane (1.2 L) was added drop wise with stirring thionyl chloride (743.56 g, 6.25 mole). The reaction mixture was set up for heating with reflux, fitted with a gas trap filled with saturated aqueous sodium bicarbonate and heated at 75° C. until the reaction mixture formed a clear solution, about 3 h. LC/MS of a sample quenched in methanol showed only methyl ester. The reaction mixture was cooled to ambient and concentrated under reduced pressure to yield 5,6-dichloronicotinoyl chloride 12 as a thick paste.

A suspension of N,O-dimethylhydroxylamine hydrochloride (350.53 g, 3.59 mole) in methylene chloride was cooled to 0° C. (internal temp, Dry Ice/acetone bath), and triethyl amine (711.5 g, 7.03 mole) was added. The 5,6-dichloronicotinoyl chloride from above was dissolved in methylene chloride (2.4 L) and added to the mixture at a rate such that the internal temperature did not exceed 15° C. After addition of the acid chloride, the reaction mixture was allowed to warm slowly to ambient overnight.

The crude reaction mixture was poured into 2 L water, the layers were separated, and the aqueous was extracted 2×500 mL with methylene chloride. The combined organic layers were dried ($MgSO_4$) and concentrated under reduced pressure to yield a brown solid. The solid was then treated with 1 L of boiling hexanes and heated at reflux for ~10 min. The resulting pale orange solution was decanted from the dark yellow-brown tar and allowed to cool. This step was repeated with the tar 2×500 mL. The hexane mixtures were allowed to cool first to ambient then cooled on ice/water baths. The resulting yellow needles were collected by vacuum filtration and air dried to yield 730 g (99%) of the desired amide, which was suitable to be carried on to the next step. $^1$H NMR (400 MHz, $CDCl_3$) δ 8.68 (m, 1H), 8.18 (m, 1H), 3.59 ($OCH_3$, 3H), 3.40 ($NCH_3$, 3H).

2-Propanol recrystallization of
5,6-dichloro-N-methoxy-N-methyl-nicotinamide 3

The procedure above was followed using 600 g of 5,6-dichloronicotinic acid 11 and keeping all other reagents and ratios the same until the crude product was isolated. The crude product was dissolved in hot 2-propanol, 1.4 mL/g, and allowed to cool slowly to room temperature. The resulting pale yellow solid was isolated by filtration, and the resulting supernatant was cooled to 0° C. to yield a second crop. The supernatant was subsequently reduced in volume by approximately 70% and cooled to 0° C. to yield a slightly darker yellow third crop that was identical by LC/MS to the first two crops. Overall 730 g was isolated for a 97% yield.

1-(5,6-Dichloro-pyridin-3-yl)-ethanone 14

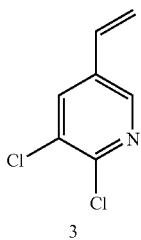

To a solution of 5,6-dichloro-N-methoxy-N-methyl-nicotinamide 13 (549 g, 2.335 mole) in dry THF (2.335 L) cooled to −35° C. (internal temperature, Dry Ice/acetone bath) was added slowly drop wise methylmagnesium chloride solution (913 g, 2.68 mole) at a rate such that the internal temperature did not exceed −10° C. The reaction mixture was allowed to stir for 3 h between −25 and −15° C., at which point an aliquot was analyzed by LC/MS to insure the reaction had gone to completion.

The reaction mixture was poured into 2.3 L of 1N HCl. The layers were separated, the aqueous layer was washed 2×500 mL with diethyl ether, and the combined organic layers were dried (MgSO$_4$) and concentrated under reduced pressure to yield a pale yellow solid.

The solid was taken up in about 450 mL of hot 2-propanol. Upon cooling, the solution deposited pale yellow needles. The mixture was further cooled (ice/water bath) and the resulting solid was collected by vacuum filtration and air dried. The 2-propanol supernatant was concentrated to produce an additional crop of needles. Total yield 431 g, 97%. $^1$H NMR (400 MHz, CDCl$_3$) δ 8.82 (m, 1H), 8.29 (m, 1H), 2.62 (COCH$_3$, 3H).

1-(5,6-Dichloro-pyridin-3-yl)-ethanol 15

To a well stirred suspension of sodium borohydride (66.21 g, 1.75 mole) in methanol (3.5 L) cooled to 0° C. with a Dry Ice/acetone bath was added 1-(5,6-dichloro-pyridin-3-yl)-ethanone 14 (665 g, 3.5 mole) at a rate such that the temperature remained at 0° C. After solid addition was complete, the reaction mixture was stirred an additional 1 h, after which time LC/MS analysis of an aliquot showed that the reaction was complete.

The methanol was removed under reduced pressure, and the residue was taken up in 2 L diethyl ether and 2 L 1 N HCl. The layers were separated, the aqueous was extracted 2×250 mL with ether, and the combined organic layers were dried (MgSO$_4$) and concentrated under reduced pressure to yield a pale yellow oil, 670 g, 99%, which was carried on without further purification. $^1$H NMR (400 MHz, CDCl$_3$) δ 8.20 (m, 1H), 7.82 (m, 1H) 4.96 (m, 1H), 3.57 (s, 1H), 1.51 (d, J=6.5 Hz, 3H).

1-(5,6-Dichloro-pyridin-3-yl)-ethanol (15) hydrochloride salt formation

To a solution of 1-(5,6-dichloro-pyridin-3-yl)-ethanol 15 (200 g, 1.04 mole) in ethyl acetate (200 mL) was added a solution of hydrogen chloride in dioxane/ethyl acetate prepared by diluting 4N HCl in dioxane (265 mL, 1.06 mole) in ethyl acetate (265 mL) with manual stirring. After a few moments, a cream colored solid began to precipitate. The resulting mixture was allowed to cool to ambient and was then further cooled in an ice/water bath. The solid was isolated by vacuum filtration, washed with additional ethyl acetate (250 mL), and allowed to air dry for about 20 min. This solid (231 g, 97% yield) contained traces of ethyl acetate and was suitable for further reaction without additional drying. $^1$H NMR (400 MHz, CD$_3$OD) δ 8.36 (m, 1H), 8.03 (m, 1H) 4.92 (m, 1H), 1.47 (d, J=6.5 Hz, 3H).

2,3-Dichloro-5-vinyl-pyridine 3

To a solution of the 1-(5,6-dichloro-pyridin-3-yl)-ethanol 15 (311 g. 1.62 mole) in chlorobenzene (3 L) was added p-toluene sulfonic acid (431 g, 2.5 mole) and the reaction mixture was heated at reflux with concomitant removal of water. When the reaction was complete the mixture was concentrated to about 500 mL, diluted with 2 L water, and extracted with 3×1 L ethyl acetate. The organic layer was dried (Na$_2$SO$_4$), concentrated under reduced pressure with low heat, dissolved in 500 mL methylene chloride, and applied to the top of 2 Kg silica column. The purified vinyl pyridine was eluted with a slight gradient of ethyl acetate in hexane, 0% to 10%. 178.55 g, 100% pure 2,3-dichloro-5-vinylpyridine was collected as a clear oil which solidified upon cooling to 4° C. 63% yield. $^1$H NMR (400 MHz, CDCl$_3$) δ 8.27 (m, 1H), 7.80 (dd, J=12, 18 Hz, 1H), 6.62 (d, J=18 Hz, 1H), 5.46 (d, J=12 Hz, 1H).

Synthesis of Intermediate Fluoro-3,6-dihydro-2H-[1,2']bipyridinyl-4-carboxylic acid (21)

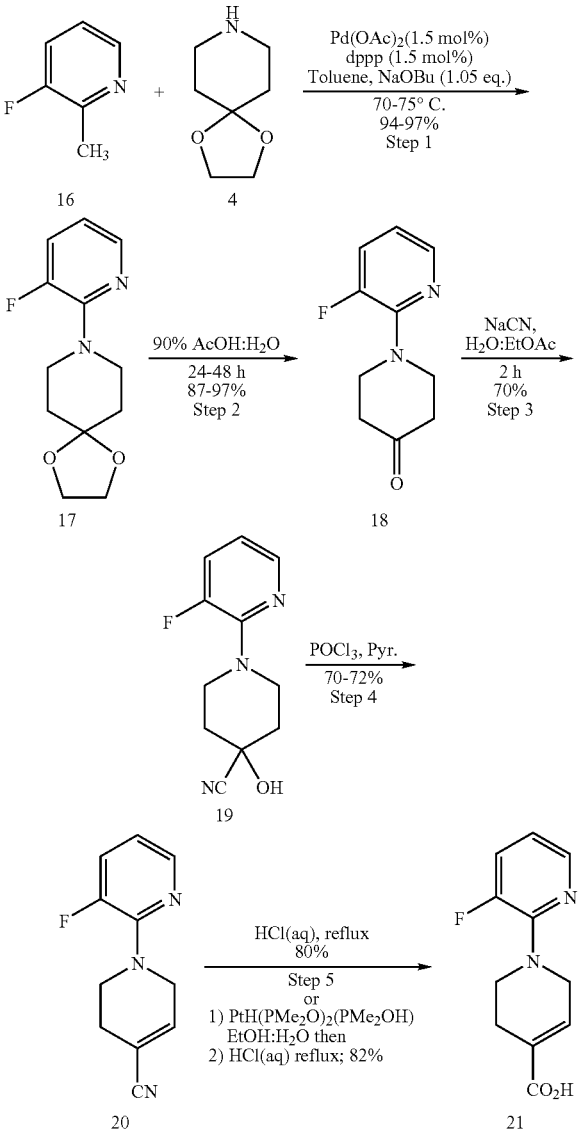

Step 1: Preparation of 8-(3-fluoro-pyridin-2-yl)-2,3-dioxa-8-azaspiro[4.5]decane (17)

1,4-Dioxa-8-azaspiro[4.5]decane 4 (114.29 g, 798.23 mMol) was dissolved in dry toluene (900 mL) under nitrogen. Palladium acetate (1.706 g, 7.6 mMol) was added followed by 1,3-bis(diphenylphosphino)propane (3.14 g, 7.6 mMol), and sodium t-butoxide (76.7 g, and the mixture warmed to 70° C. with mechanical stirring (paddle stirrer) using a heating mantle. 2-Chloro-3-fluoropyridine 16 (100 g, 760.2 mMol) in toluene (500 mL) was added dropwise ensuring the temperature did not rise above 75° C. LC/MS of the reaction were taken at 0.5 hourly intervals during the course of the reaction.

After 300 mL of the solution had been added during 1 hour, LC/MS showed the reaction to have stopped, so a further portion of palladium acetate (426.5 mg, 1.8 mMol) and 1,3-bis(diphenylphosphino)propane (785 mg, 1.8 mMol) were added. At the 500 ml time point (2 h) a further portion of palladium acetate (426.5 mg, 1.8 mMol) and 1,3-bis(diphenylphosphino)propane (785 mg, 1.8 mMol) were added. The final 100 ml of solution was added and the mixture stirred for a further 1 h at 75° C. The mixture was cooled to room temperature and filtered through silica gel (500 g) using a sintered funnel. The filter pad was washed with hexane:ethyl acetate (4:1, 4 L) and the filtrate evaporated to dryness in vacuo to leave a yellow oil, which solidified on standing. This was purified by distillation under vacuum at 2 mmHg (2.7 mbar) to give the title compound 17 (176 g, 97%) boiling point=114-117° C., melting point=45-47° C. $\delta_H$ {400 MHz, $CDCl_3$} 7.98 (1H, dt, J=5, 1 Hz), 7.20 (1H, dq, J=7.5, 1 Hz), 6.72 (1H, dt, J=7.5, 1 Hz), 4.00 (4H, s), 3.61 (4H, m), 1.82 (4H, m).

Step 2: 3'-Fluoro-2,3,5,6-tetrahydro-[1,2']bipyridinyl-4-one (18)

8-(3-fluoro-pyridin-2-yl)-2,3-dioxa-8-azaspiro[4.5]decane 17 (347 g, 1.456 Mol) was dissolved in acetic acid (700 mL) and water (140 mL) and the mixture heated to 85° C. under nitrogen for 18 h. LC/MS shows the reaction at 92% conversion at this stage. The mixture was evaporated to dryness in vacuo, to leave orange oil. This material was used directly in the next step without further purification Step 3: 3'-Fluoro-4-hydroxy-3,4,5,6-tetrahydro-2H-[1,2']bipyridinyl-4-carbonitrile (19)

The oil was diluted with water (1,000 mL) and carefully neutralized using sodium bicarbonate to pH 8. Ethyl acetate (1 L) was added followed by sodium cyanide (85.7 g, 1.747 Mol) and the mixture stirred vigorously at room temperature for 2 h. The organic phase was separated, and the aqueous phase extracted with ethyl acetate (2×1 L), the combined organics dried ($MgSO_4$) and the solvent evaporated to dryness in vacuo to leave an orange oil. This material was chromatographed over a pad of flash silica (ca 1 Kg) eluting with hexanes:ethyl acetate (12:1) (20 L, discarded) to remove higher running impurities, followed by hexanes:ethyl acetate (5:1) (20 L) to give pale yellow oil. This was suspended in hexanes (1 L) and a seed crystal of the desired product added, and the mixture stirred vigorously with ice-water cooling for ca 2 h. The mixture was filtered to give the title compound 19 (225 g, 70%) as a white solid, m.p.=76-78° C. $\delta_H$ {400 MHz, $CDCl_3$} 8.00 (1H, dt, J=5, 1 Hz), 7.25 (1H, dq, J=7.5, 1 Hz), 6.80 (1H, dt, J=5, 1 Hz), 3.85 (2H, m), 3.45 (2H, m), 2.92 (1H, s), 2.23 (2H, m), 2.02 (2H, m).

Step 4: 3'-Fluoro-3,6-dihydro-2H-[1,2']bipyridinyl-4-carbonitrile (20)

3: 3'-Fluoro-4-hydroxy-3,4,5,6-tetrahydro-2H-[1,2']bipyridinyl-4-carbonitrile 19 (100 g, 450.2 mMol) was dissolved in dry pyridine (1,000 mL) and cooled to 0° C. under nitrogen. Phosphorus oxychloride (85 mL, 940 mMol) was added dropwise ensuring the temperature did not rise above 10° C. during the addition, and the resulting mixture stirred at 0° C. overnight using a lagged cooling bath. The mixture was cautiously poured into ice-water (3,000 mL) with stirring, and the pH adjusted to 6.0 using potassium phosphate buffer. The mixture was extracted with ethyl acetate (3×2,000 mL), dried ($MgSO_4$) and the solvent evaporated to dryness in vacuo to leave orange oil. Flash chromatography of the residue eluting with hexanes:ethyl acetate (10:1) gave the title compound 20 (65 g, 72%) as a white solid m.p.=76-77° C. $\delta_H$ {400 MHz, $CDCl_3$} 8.01 (1H, d, J=5 Hz), 7.27 (1H, dd, J=20, 8 Hz), 6.79 (1H, m), 6.71 (1H, m), 4.16 (2H, dd, J=12, 3 Hz), 3.65 (2H, t, J=6 Hz), 2.50 (2H, m).

Step 5: 3'-Fluoro-3,6-dihydro-2H-[1,2']bipyridinyl-4-carboxylic acid (21)

3'-Fluoro-3,6-dihydro-2H-[1,2']bipyridinyl-4-carbonitrile (165 g, 811.9 mMol) was dissolved in 6M hydrochloric acid (800 mL) and the solution heated to 105° C. for 28 h using a heating mantle. The reaction was followed by LC/MS, which showed the reaction to be 98% complete after this time. The mixture was evaporated to dryness, and the residue dissolved in water (2,000 mL) and basified to pH 4.9 using potassium carbonate. The solid was filtered off, washed with water (500 mL) and dried under vacuum. The solid was dissolved in dichloromethane (2,000 mL), dried ($MgSO_4$) and the solvent evaporated to dryness to give a pale yellow solid. This was triturated with hexanes:ethyl acetate (3:1) (1,000 ml) to give the title compound 21 (143 g, 79.5%) as a white solid, m.p.=119-120° C. $\delta_H$ {400 MHz, $CDCl_3$} 8.02 (1H, dt, J=5, 2 Hz), 7.25 (1H, ddd, J=20, 10, 1 Hz), 7.17 (1H, m), 6.76 (1H, m), 4.21 (2H, m), 3.65 (2H, t, J=5 Hz), 2.55 (2H, m).

Alternate Step 5: Preparation of platinum catalyst $PtH(PMe_2O)_2(PMe_2OH)$

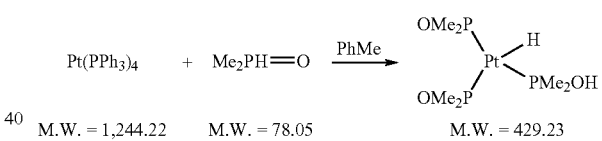

M.W. = 1,244.22   M.W. = 78.05   M.W. = 429.23

Dimethylphosphine oxide (1.6 g, 20.5 mMol) was added to a stirred suspension of tetrakis-triphenylphosphine platinum (5.0 g, 4.02 mMol) in dry toluene (100 mL) under nitrogen. After about 15 minutes a solution was formed and after a further 10 minutes the product began to precipitate from solution. The mixture was diluted with dry diethyl ether (100 mL) and stirred for a further 1 h. The mixture was filtered and dried in vacuo to give the desired product (1.3 g) as a buff colored solid. The filtrate was concentrated in vacuo to about (20 ml) and ether (100 mL) added to precipitate further product, which was filtered off and dried in vacuo to give a further (200 mg).

3'-Fluoro-3,6-dihydro-2H-[1,2']bipyridinyl-4-carboxamide (22)

3'-Fluoro-3,6-dihydro-2H-[1,2']bipyridinyl-4-carbonitrile 20 (10.0 g, 49.2 mMol) was dissolved in ethanol:water (2:1, 150 mL) with stirring and heating. $PtH(PMe_2O)_2(PMe_2OH)$ (50 mg, 0.025 mol %) was added and the solution stirred under reflux for 2 h. LC/MS showed the reaction to be 100% complete after this time. The cooled solution was evaporated to dryness in vacuo to leave a white solid. The solid was filtered through a flash pad of silica gel to remove the catalyst to give the title compound as a white solid (10.9 g, 100%).

3'-Fluoro-3,6-dihydro-2H-[1,2']bipyridinyl-4-carboxylic acid (21)

3'-Fluoro-3,6-dihydro-2H-[1,2']bipyridinyl-4-carboxamide (8.75 g, 39.5 mMol) was dissolved in 6M hydrochloric acid (100 mL) and heated to 100° C. with stirring for 2 h. LC/MS showed the reaction to be complete after this time. The solvent was removed in vacuo and the residue dissolved in water (100 mL). The solution was basified to pH 5.8 with potassium carbonate, at which point a precipitate formed. This was filtered off and washed with water (20 mL). The solid was dissolved in dichloromethane (200 mL), dried (MgSO$_4$) and the solvent evaporated to dryness in vacuo to give the title compound 7 as a white solid (7.2 g, 82%).

This two step procedure to form 21 is preferred in that it is better than direct hydrolysis of the nitrile for two reasons. Firstly the two reactions are much cleaner giving an analytically pure colorless product, whereas the nitrile hydrolysis gives a yellow solid, which requires trituration to remove colored impurities. Secondly the two step procedure is much quicker requiring only 4 hours for 100% conversion, whereas the nitrile hydrolysis requires 28 hours and only goes 98% to completion.

Synthesis of Diols A14 and B14

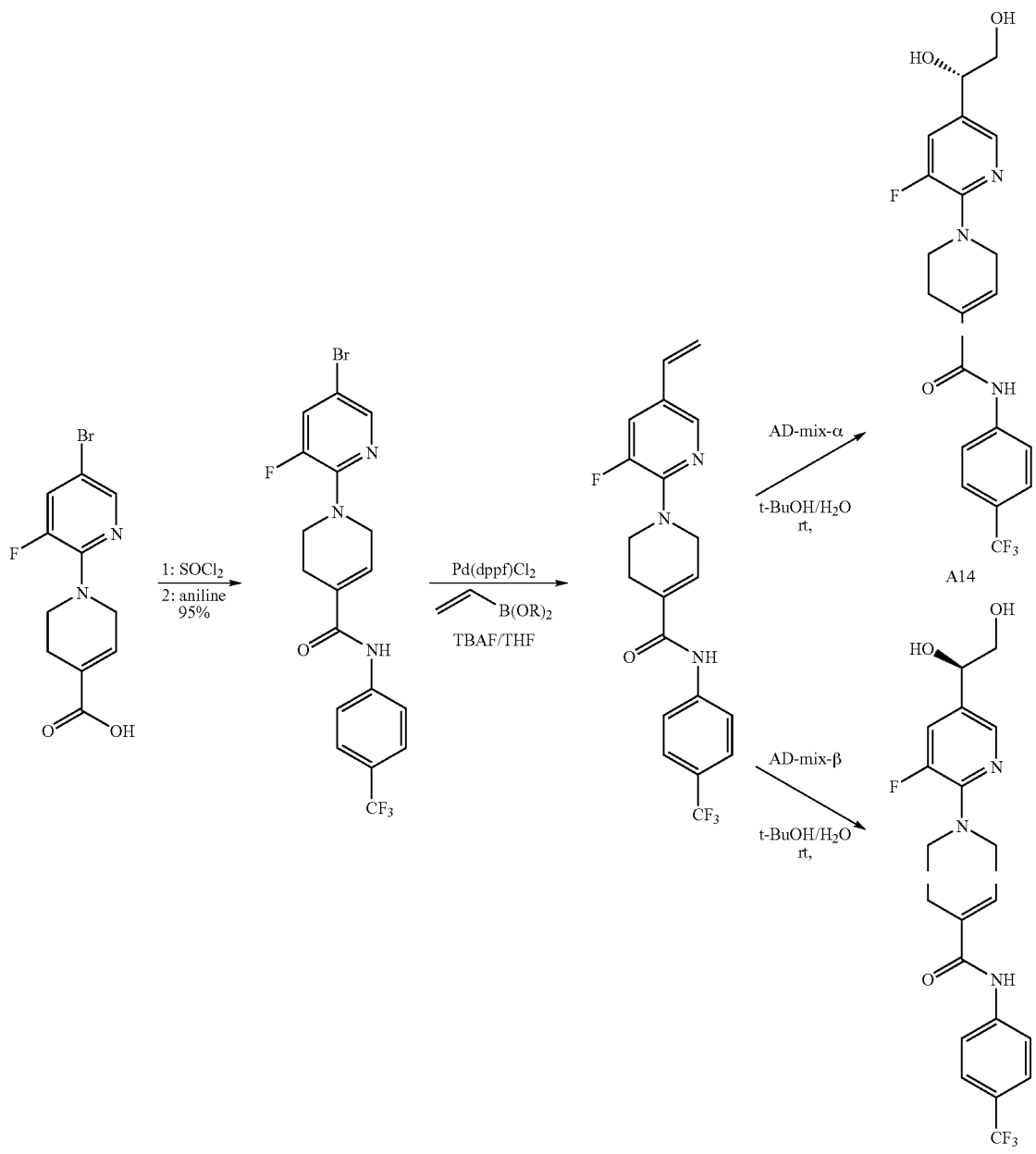

Synthesis of 24

The solution of acid 23 (1.96 g, 6.51 mMol) in thioyl chloride (10 mL) was stirred at 50° C. for 1 hour. Then the mixture was evaporated to dryness for next step.

To the above crude acid chloride was added DCM (30 mL) and 4-trifluoromethylaniline (1.20 g, 6.51 mMol) at 0° C. Then the resultant mixture was added dropwise pyridine (1.58 mL) and kept stirring for additional 2 hours at 0° C. After quenching with sodium bicarbonate aqueous solution, the mixture was extracted with dichloromethane and concentrated to dryness, obtaining the crude product 24, which was washed with 5% EtOAc/Hexanes to give a white solid in 95% yield. 24: $^1$H NMR (CDCl$_3$) δ 8.07 (m, 1H), 7.71 (d, J=8.0 Hz, 2H), 7.62 (d, J=8.0 Hz, 2H), 7.57 (br s, 1H), 7.43 (dd, J=2.2, 12.1 Hz, 1H), 6.80 (m, 1H), 4.22 (dd, J=3.0, 6.2 Hz, 2H), 3.72 (t, J=5.7 Hz, 2H), 2.66 (m, 2H), m/z (M+1): 444.2.

Synthesis of 25

To a solution of the compound 24 (0.89 g, 2.0 mMol) and tetrabutylammonium fluoride (10 ml, 1 M solution in tetrahydrofuran) was added 4,4,6-trimethyl-2-vinyl-1,3,2-dioxaborinane (0.62 g, 4.0 mMol) and [1,1-bis(diphenylphosphino)ferrocene]dichloropalladium(II) complex with dichloromethane (1:1) (0.082 g, 0.1 mmol) at room temperature. Then the mixture was heated to reflux overnight. After quenching with water, the mixture was extracted with EtOAc and concentrated to dryness, obtaining the crude product, which was purified by flash chromatography with Hexanes/EtOAc (4:1) to afford a pure compound 25 as a white solid in 48% yield. 25: $^1$H NMR (CD$_3$OD) δ 7.98 (s, 1H), 7.84 (m, 2H), 6.82 (m, 3H), 6.82 (m, 1H), 6.70 (m, 1H), 5.73 (m, 1H), 5.25 (m, 1H), 4.23 (m, 2H), 3.72 (t, J=5.4 Hz, 2H), 2.62 (m, 2H) ppm, m/z (M+1): 392.2.

Synthesis of A14

To a suspension of the compound 25 (0.16 g, 0.409 mMol) in tert-butanol (4 mL) and water (4 mL) was add AD-mix-α (0.68 g, 0.409 mMol) at 0° C. Then the resultant mixture was warmed up to room temperature and kept stirring for 48 hours. After quenching with sodium bicarbonate aqueous solution, the mixture was extracted with EtOAc and concentrated to dryness, obtaining the crude product A14, which was purified by flash chromatography with EtOAc to afford a pure compound A14 as a white solid. The enantiomeric excess (ee) was detected to be >99%. A14: $^1$H NMR (CD$_3$OD) δ 8.01 (s, 1H), 7.85 (d, J=8.5 Hz, 2H), 7.63 (d, J=8.5 Hz, 2H), 7.47 (dd, J=1.8, 13.8 Hz, 1H), 6.82 (m, 1H), 4.67 (t, J=6.0 Hz, 1H), 4.19 (dd, J=2.9, 6.1 Hz, 2H), 3.70-3.62 (m, 4H), 2.61 (m, 2H) ppm, m/z (M+1): 426.5.

Synthesis of B14

To a suspension of the compound 25 (0.16 g, 0.409 mMol) in tert-butanol (4 mL) and water (4 mL) was add AD-mix-β (0.68 g, 0.409 mMol) at 0° C. Then the resultant mixture was warmed up to room temperature and kept stirring for 48 hours. After quenching with sodium bicarbonate aqueous solution, the mixture was extracted with EtOAc and concentrated to dryness, obtaining the crude product B14, which was purified by flash chromatography with EtOAc to afford a pure compound B14 as a white solid. The enantiomeric excess (ee) was detected to be >99%. B14: $^1$H NMR (CD$_3$OD) δ 8.01 (s, 1H), 7.85 (d, J=8.5 Hz, 2H), 7.63 (d, J=8.5 Hz, 2H), 7.47 (dd, J=1.8, 13.8 Hz, 1H), 6.82 (m, 1H), 4.67 (t, J=6.0 Hz, 1H), 4.19 (dd, J=2.9, 6.1 Hz, 2H), 3.70-3.62 (m, 4H), 2.61 (m, 2H) ppm, m/z (M+1): 426.5.

Synthesis of Diols E2 and F2

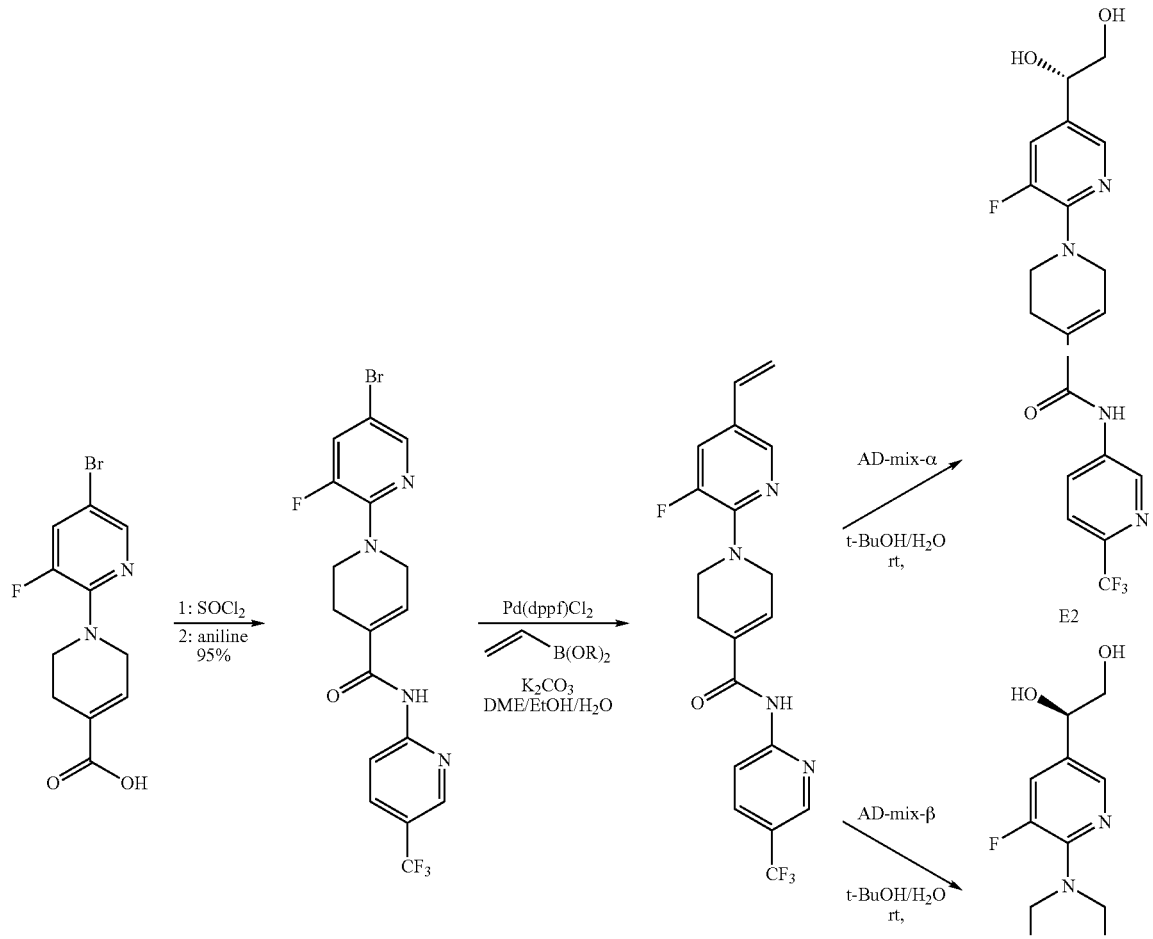

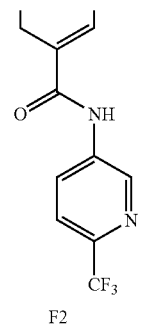

26 was synthesized using the same procedure as 24. 26: ¹H NMR (CDCl₃) δ 8.82 (m, 1H), 8.56 (m, 1H), 8.08 (m, 1H), 7.97 (m, 1H), 7.43 (m, 1H), 6.91 (m, 1H), 4.24 (dd, J=2.8, 6.1 Hz, 2H), 3.72 (t, J=6.5 Hz, 2H), 2.67 (m, 2H), m/z (M+1): 445.2.

To a solution of the compound 26 (1.34 g, 3.0 mMol) and potassium carbonate (1.40 g, 10.1 mMol) in 1,2-dimethoxyethane/ethanol/water (9 mL/4.5 mL/9 mL) was added vinylboronic acid pinacol ester (1.0 mL, 6.0 mMol) and dichlorobis(triphenylphosphine)palladium (0.60 g, 0.85 mMol) at room temperature. Then the mixture was heated to 95° C. for 1 hour. After quenching with water, the mixture was extracted with EtOAc and concentrated to dryness, obtaining the crude product, which was purified by flash chromatography with Hexanes/EtOAc (4:1) to afford a pure compound 27 as a white solid in 88% yield. 27: ¹H NMR (CD₃OD) δ 8.64 (m, 1H), 8.37 (d, J=8.9 Hz, 1H), 8.08 (d, J=1.8, 8.8 Hz, 1H), 7.99 (s, 1H), 7.60 (dd, J=1.6, 14.4 Hz, 1H), 6.91 (m, 1H), 6.68 (m, 1H), 5.71 (d, J=17.4 Hz, 1H), 5.24 (d, J=11.5 Hz, 1H), 4.24 (dd, J=2.9, 6.4 Hz, 2H), 3.72 (t, J=5.6 Hz, 2H), 2.64 (m, 2H) ppm, m/z (M+1): 393.2.

E2 was synthesized using the same procedure as A14. E2: ¹H NMR (CD₃OD) δ 8.64 (m, 1H), 8.36 (d, J=8.0 Hz, 1H), 8.08 (m, 1H), 8.01 (s, 1H), 7.49 (m, 1H), 6.91 (m, 1H), 4.67 (t, J=6.0 Hz, 1H), 4.20 (dd, J=2.9, 6.2 Hz, 2H), 3.71-3.62 (m, 4H), 2.63 (m, 2H) ppm, m/z (M+1): 427.5. ee: >99%.

F2 was synthesized using the same procedure as B14. F2: ¹H NMR (CD₃OD) δ 8.64 (m, 1H), 8.36 (d, J=8.0 Hz, 1H), 8.08 (m, 1H), 8.01 (s, 1H), 7.49 (m, 1H), 6.91 (m, 1H), 4.67 (t, J=6.0 Hz, 1H), 4.20 (dd, J=2.9, 6.2 Hz, 2H), 3.71-3.62 (m, 4H), 2.63 (m, 2H) ppm, m/z (M+1): 427.5. ee: >99%.

Synthesis of (S)-1-(5-(1,2-dihydroxyethyl)-3-fluoropyridin-2-yl)-N-(6-fluorobenzo[d]thazol-2-yl)-1,2,3,6-tetrahydropyridine-4-carboxamide (I5)

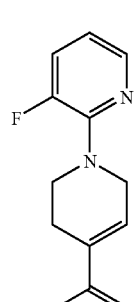

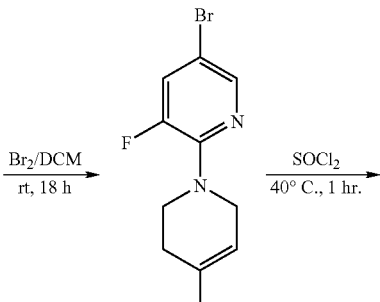

-continued

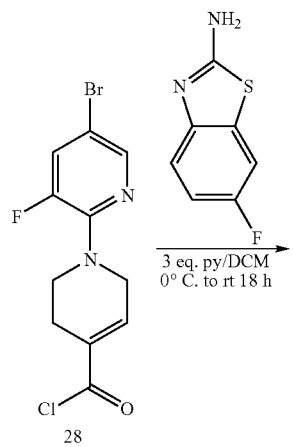

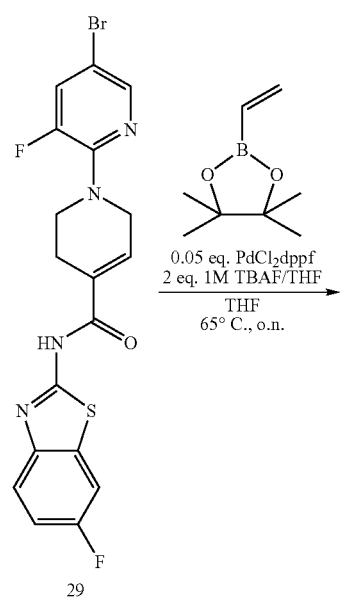

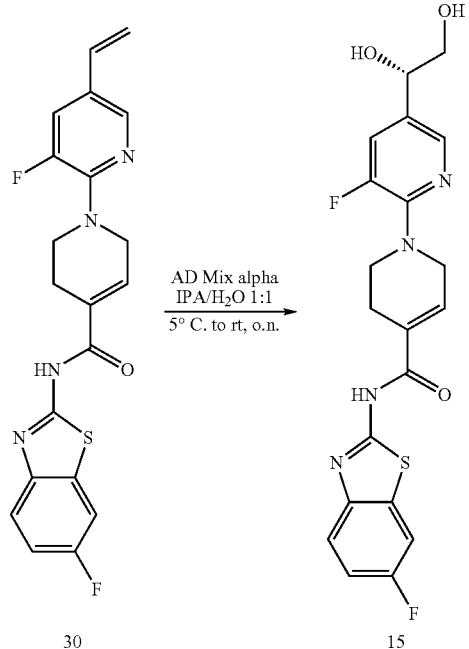 [SMILES: C=Cc1cnc(N2CC=C(C(=O)Nc3nc4ccc(F)cc4s3)CC2)c(F)c1 ; O=C(Nc1nc2ccc(F)cc2s1)C1=CCN(c2ncc([C@H](O)CO)cc2F)CC1]

Synthesis of 1-(5-bromo-3-fluoropyridin-2-yl)-1,2,3,6-tetrahydropyridine-4-carboxylic acid (23)

A 500 mL round bottom flask fitted with a rubber septum was charged with 10 grams of 1-(3-fluoropyridin-2-yl)-1,2,3,6-tetrahydropyridine-4-carboxylic acid 21 (45 mMol) and dissolved in 170 mL dichloromethane (DCM). With a syringe, 1.1 equivalents bromine (49.5 mMol) was added slowly to the solution. The reaction was allowed to progress at room temperature for 18 hours. The precipitate was collected by vacuum filtration and washed with 2×100 mL DCM. The filter cake was transferred to a 2 L beaker and covered with 300 mL 1N aq. sodium hydroxide, and stirred with a magnetic stir bar until all solids dissolved. The solution was transferred to a 1000 mL extraction funnel and shaken with 2×100 mL ethyl acetate (EtOAc). The organic layer was discarded and the aqueous layer was acidified with 50 mL 2N aq.HCl. The crude compound 23 was extracted with 2×100 mL EtOAc. The organic layer was dried over sodium sulfate, concentrated under vacuum, and crystallized as white needles from hot EtOAc. 23: (55% white solid): m/z 301, $^1$H NMR (DMSO) δ 12.42 (s, 1H), 8.14-8.11 (m, 1H), 7.93-7.87 (m, 1H), 6.94-6.89 (m, 1H), 4.13-4.07 (m, 2H), 3.58-3.52 (m, 2H), 2.40-2.33 (m, 2H).

Synthesis of 1-(5-bromo-3-fluoropyridin-2-yl)-N-(6-fluorobenzo[d]thiazol-2-yl)-1,2,3,6-tetrahydropyridine-4-carboxamide (29)

In a 50 mL vial with a screw-top septum, 1.03 grams 1-(5-bromo-3-fluoropyridin-2-yl)-1,2,3,6-tetrahydropyridine-4-carboxylic acid 23 (3.32 mMol) were cooled to 0° C. Ten milliliters thionyl chloride were poured directly onto the solid and stirred until the vial reached room temperature. The vial was heated to 45° C. for one hour. The reaction was confirmed complete by LC/MS using the methyl ester of the acid in methanol. Volatiles were removed under vacuum until the yellow solid was dry. All material was used as is in the next reaction without further characterization. In a 50 mL vial with a screw-top septum, 1-(5-bromo-3-fluoropyridin-2-yl)-1,2,3,6-tetrahydropyridine-4-carbonyl chloride (28) was dissolved in 10 mL tetrahydrofuran (THF), stirred with a magnetic stir bar, and cooled to 0° C. 1.1 eq. 2-amino-6-fluorobenzothiazole (3.65 mMol) were dissolved in 2 mL dimethylformamide (DMF) and the solution slowly added to the vial. After the reaction stirred for 10 minutes, 3 eq. pyridine (9.96 mMol) were added to the mixture dropwise and the reaction progressed for 18 hours. The precipitate was collected by vacuum filtration and washed with 2×15 mL EtOAc. (30% white solid): m/z 451, $^1$H NMR (DMSO) δ 12.43 (s, 1H), 8.17-8.10 (m, 1H), 7.96-7.95 (m, 1H), 7.86-7.78 (m, 1H), 7.71-7.64 (m, 1H), 7.28-7.19 (m, 1H), 7.09-7.04 (m, 1H), 4.19-4.12 (m, 2H), 3.64-3.51 (m, 2H), 2.59-2.53 (m, 2H).

Synthesis of 1-(3-fluoro-5-vinylpyridin-2-yl)-N-(6-fluorobenzo[d]thiazol-2-yl)-1,2,3,6-tetrahydropyridine-4-carboxamide (30)

687 mg of 1-(5-bromo-3-fluoropyridin-2-yl)-N-(6-fluorobenzo[d]thiazol-2-yl)-1,2,3,6-tetrahydropyridine-4-carboxamide 29 (1.52 mmol) and 0.05 eq. PdCl$_2$dppf catalyst ([1,1'-bis(diphenylphosphino)ferrocene] dichloropalladium (II), 0.08 mMol, Sigma-Aldrich) were placed in a 50 mL vial with a screw-top septum and suspended in 2 mL dry THF. 2 Eq. 1M tetrabutylammonium fluoride in THF (3.04 mL, Sigma-Aldrich) were then added and the vial heated to 65° C. 1.1 Eq. vinylboronic acid pinacol ester (1.6 mMol, Sigma-Aldrich) were added to the vial via a syringe and the reaction progressed over 18 hours. The reaction mixture was transferred to a 500 mL extraction funnel and diluted with 250 mL water. The compound was extracted with 2×100 mL EtOAc. The organic layer was dried over sodium sulfate and concentrated under vacuum. The residue was chromatographed with a gradient of EtOAc in hexane. The fractions containing desired product (visualized by LC/MS) were concentrated and used without further purification or characterization.

Synthesis of (S)-1-(5-(1,2-dihydroxyethyl)-3-fluoropyridin-2-yl)-N-(6-fluorobenzo[d]thiazol-2-yl)-1,2,3,6-tetrahydropyridine-4-carboxamide (I5)

In a 100 mL round bottom flask the crude residue of 1-(3-fluoro-5-vinylpyridin-2-yl)-N-(6-fluorobenzo[d]thiazol-2-yl)-1,2,3,6-tetrahydropyridine-4-carboxamide 30 was dissolved in a solution of 15 mL isopropyl alcohol and 15 mL water. After the solution was cooled to 5° C. in an ice bath, 1.7 grams AD Mix α (Sigma-Aldrich) was added in one portion. The reaction was allowed to progress for 18 hours, at which time all starting material was consumed. The reaction mixture was diluted with 250 mL water in a 500 mL extraction funnel and washed with 2×100 mL EtOAc. The organic layer was dried over sodium sulfate, concentrated to a residue, and chromatographed first with a gradient of EtOAc in hexane, and then a gradient of methyl alcohol in DCM. After the fractions containing desired product were concentrated, the final product was precipitated from a heated solution of DCM, methyl alcohol, and hexane. 0.6% yield over the last two reactions. m/z: 432, $^1$H NMR (DMSO) δ 12.40 (s, 1H), 8.00-7.95 (m, 1H), 7.94-7.87 (m, 1H), 7.80-7.72 (m, 1H), 7.50-7.41 (m, 1H), 7.34-7.26 (m, 1H), 7.17-7.13 (m, 1H), 5.36-5.31 (m, 1H), 4.79-4.72 (m, 1H), 4.55-4.48 (m, 1H), 4.17-4.11 (m, 2H), 3.61-3.53 (m, 2H), 3.53-3.37 (m, 2H), 2.59-2.52 (m, 2H).

The compounds of Formula (I) where X is S can be obtained by methods analogous to that described in Scheme 1 to provide the compounds of Formulae (I)-(V) where X is O, except that an isothiocyanate of Formula Ar₂—NCS is used in place of the isocyanate Ar₂—NCO.

Where m=1, a mixture of compounds of Formulae (I)-(V) is generally obtained. The mixture can be separated via conventional methods, for example, column chromatography.

Isothiocyanates are commercially available or can be prepared by reacting an amine of Formula Ar₂NH₂ with thiophosgene as shown in the scheme below (See, e.g., *Tetrahedron Lett.*, 41(37):7207-7209 (2000); *Org. Prep. Proced., Int.*, 23(6):729-734 (1991); *J. Heterocycle Chem.*, 28(4):1091-1097 (1991); *J. Fluorine Chem.*, 41(3):303-310 (1988); and *Tetrahedron. Lett.*, 42(32):5414-5416 (2001).

Alternatively, isothiocyanates of Formula Ar₂—NCS can be prepared by reacting an amine of Formula Ar₂NH₂ with carbon disulfide in the presence of triethylamine in THF, followed by reaction with hydrogen peroxide and hydrochloric acid in water as shown in the scheme below (See, e.g., *J. Org. Chem.*, 62(13):4539-4540 (1997)).

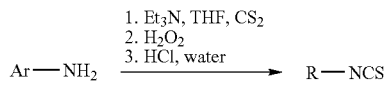

Therapeutic Uses of the Compounds of Formulae (I)-(V)

In accordance with the invention, the compounds of Formulae (I)-(V) are administered to an animal in need of treatment or prevention of a Condition.

In one embodiment, an effective amount of a compound of Formulae (I)-(V) can be used to treat or prevent any condition treatable or preventable by inhibiting TRPV1. Examples of conditions that are treatable or preventable by inhibiting TRPV1 include, but are not limited to, pain, UI, an ulcer, IBD, and IBS.

The compounds of Formulae (I)-(V) or a pharmaceutically acceptable derivative thereof can be used to treat or prevent acute or chronic pain. Examples of pain treatable or preventable using the compounds of Formulae (I)-(V) include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The compounds of Formulae (I)-(V) or a pharmaceutically acceptable derivative thereof can also be used for treating or preventing pain associated with inflammation or with an inflammatory disease in an animal. Such pain can arise where there is an inflammation of the body tissue which can be a local inflammatory response and/or a systemic inflammation. For example, the compounds of Formulae (I)-(V) can be used to treat or prevent pain associated with inflammatory diseases including, but not limited to: organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory disease of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer.

The compounds of Formulae (I)-(V) or a pharmaceutically acceptable derivative thereof can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The compounds of Formulae (I)-(V) or a pharmaceutically acceptable derivative thereof can be used to treat or prevent UI. Examples of UI treatable or preventable using the compounds of Formulae (I)-(V) include, but are not limited to, urge incontinence, stress incontinence, overflow incontinence, neurogenic incontinence, and total incontinence.

The compounds of Formulae (I)-(V) or a pharmaceutically acceptable derivative thereof can be used to treat or prevent an ulcer. Examples of ulcers treatable or preventable using the compounds of Formulae (I)-(V) include, but are not limited to, a duodenal ulcer, a gastric ulcer, a marginal ulcer, an esophageal ulcer, or a stress ulcer.

The compounds of Formulae (I)-(V) or a pharmaceutically acceptable derivative thereof can be used to treat or prevent IBD, including Crohn's disease and ulcerative colitis.

The compounds of Formulae (I)-(V) or a pharmaceutically acceptable derivative thereof can be used to treat or prevent IBS. Examples of IBS treatable or preventable using the compounds of Formulae (I)-(V) include, but are not limited to, spastic-colon-type IBS and constipation-predominant IBS.

Compounds of Formulae (I)-(V) or a pharmaceutically acceptable derivative thereof are believed to function mechanistically as antagonists for TRPV1.

The invention also relates to methods for inhibiting TRPV1 function in a cell comprising contacting a cell capable of expressing TRPV1 with an effective amount of a compound of Formulae (I)-(V) or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. The method is also useful for inhibiting TRPV1 function in a cell in vivo, in an animal, a human in one embodiment, by contacting a cell, in an animal, with an effective amount of a compound of Formulae (I)-(V) or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

Therapeutic/Prophylactic Administration and Compositions of the Invention

Due to their activity, the compounds of Formulae (I)-(V) or a pharmaceutically acceptable derivative thereof are advantageously useful in veterinary and human medicine. As described above, the compounds of Formulae (I)-(V) or a pharmaceutically acceptable derivative thereof are useful for treating or preventing a condition in an animal in need thereof.

When administered to an animal, the compounds of Formulae (I)-(V) or a pharmaceutically acceptable derivative thereof are administered as a component of a composition that comprises a pharmaceutically acceptable carrier or excipient. The present compositions, which comprise a compound of Formulae (I)-(V), can be administered orally. The compounds of Formulae (I)-(V) of the invention can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the compound of Formulae (I)-(V).

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the compounds of Formulae (I)-(V) into the bloodstream.

In specific embodiments, it can be desirable to locally administer the compounds of Formulae (I)-(V) or a pharmaceutically acceptable derivative thereof. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the compounds of Formulae (I)-(V) or a pharmaceutically acceptable derivative thereof into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and Formulation with an aerosolizing agent, or via perfusion in a fluorocarbon or synthetic pulmonary surfactant. In certain embodiments, the compounds of Formulae (I)-(V) or a pharmaceutically acceptable derivative thereof can be formulated as a suppository, with traditional binders and excipients such as triglycerides.

In another embodiment, the compounds of Formulae (I)-(V) can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the compounds of Formulae (I)-(V) or a pharmaceutically acceptable derivative thereof can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg,* 71:105 (1989)). In yet another embodiment, a controlled- or sustained-release system can be placed in proximity of a target of the compounds of Formulae (I)-(V), e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the compound of Formulae (I)-(V) is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release Formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the compounds of Formulae (I)-(V) or a pharmaceutically acceptable derivative thereof are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release Formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the compounds of Formulae (I)-(V) or a pharmaceutically acceptable derivative thereof can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the compounds of Formulae (I)-(V) or a pharmaceutically acceptable derivative thereof are to be administered by infusion, they can be dispensed, for example, with an infusion bottle containing sterile pharmaceutical grade water or saline. Where the compounds of Formulae (I)-(V) or a pharmaceutically acceptable derivative thereof are administered by injection, an ampule of sterile water for injection or saline can be provided so that the ingredients can be mixed prior to administration.

The compounds of Formulae (I)-(V) or a pharmaceutically acceptable derivative thereof can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release Formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a compound of Formulae (I)-(V) or a pharmaceutically acceptable derivative thereof to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the compound of Formulae (I)-(V) or a pharmaceutically acceptable derivative thereof, and can thus reduce the occurrence of adverse side effects.

Controlled- or sustained-release compositions can initially release an amount of a compound of Formulae (I)-(V) or a pharmaceutically acceptable derivative thereof that promptly produces the desired therapeutic or prophylactic effect, and gradually and continually release other amounts of the compound of Formulae (I)-(V) to maintain this level of therapeutic or prophylactic effect over an extended period of time. To maintain a constant level of the compound of Formulae (I)-(V) in the body, the compound of Formulae (I)-(V) can be released from the dosage form at a rate that will replace the amount of compound of Formulae (I)-(V) being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the compound of Formulae (I)-(V) or a pharmaceutically acceptable derivative thereof that is effective in the treatment or prevention of a condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a compound of Formulae (I)-(V), in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one compound of Formulae (I)-(V) is administered, the effective dosage amounts correspond to the total amount administered.

Where a cell capable of expressing TRPV1 is contacted with a compound of Formulae (I)-(V) in vitro, the amount effective for inhibiting the TRPV1 receptor function in a cell will typically range from about 0.01 µg/L to about 5 mg/L, in one embodiment, from about 0.01 µg/L to about 2.5 mg/L, in another embodiment, from about 0.01 µg/L to about 0.5 mg/L, and in another embodiment, from about 0.01 µg/L to about 0.25 mg/L of a solution or suspension of a pharmaceutically acceptable carrier or excipient. In one embodiment, the volume of solution or suspension comprising the compound of Formulae (I)-(V) is from about 0.01 µL to about 1 mL. In another embodiment, the volume of solution or suspension is about 200 µL.

Where a cell capable of expressing TRPV1 is contacted in vivo with a compound of Formulae (I)-(V) or a pharmaceutically acceptable derivative thereof, the amount effective for inhibiting the receptor function in a cell will typically range from about 0.01 mg/kg of body weight to about 2500 mg/kg of body weight, although it typically ranges from about 100 mg/kg of body weight or less. In one embodiment, the effective dosage amount ranges from about 0.01 mg/kg of body weight to about 100 mg/kg of body weight of a compound of Formulae (I)-(V) or a pharmaceutically acceptable derivative thereof, in another embodiment, about 0.020 mg/kg of body weight to about 50 mg/kg of body weight, and in another embodiment, about 0.025 mg/kg of body weight to about 20 mg/kg of body weight. In one embodiment, an effective dosage amount is administered about every 24 h. In another embodiment, an effective dosage amount is administered about every 12 h. In another embodiment, an effective dosage amount is administered about every 8 h. In another embodiment, an effective dosage amount is administered about every 6 h. In another embodiment, an effective dosage amount is administered about every 4 h.

The compounds of Formulae (I)-(V) or a pharmaceutically acceptable derivative thereof can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering to the animal being administered a compound of Formulae (I)-(V) or a pharmaceutically acceptable derivative thereof another therapeutic agent. In one embodiment, the other therapeutic agent is administered in an effective amount.

The present methods for inhibiting TRPV1 function in a cell capable of expressing TRPV1 can further comprise contacting the cell with an effective amount of another therapeutic agent.

Effective amounts of the other therapeutic agents are known to those skilled in the art. However, it is within the skilled artisan's purview to determine the the other therapeutic agent's optimal effective-amount range. In one embodiment of the invention, where another therapeutic agent is administered to an animal, the effective amount of the compound of Formulae (I)-(V) or a pharmaceutically acceptable derivative thereof is less than its effective amount would be where the other therapeutic agent is not administered. In this case, without being bound by theory, it is believed that the compounds of Formulae (I)-(V) or a pharmaceutically acceptable derivative thereof and the other therapeutic agent act synergistically to treat or prevent a Condition.

The other therapeutic agent can be, but is not limited to, an opioid agonist, a non-opioid analgesic, a non-steroidal anti-inflammatory agent, an antimigraine agent, a Cox-II inhibitor, an antiemetic, a β-adrenergic blocker, an anticonvulsant, an antidepressant, a Ca2+-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for inhibiting vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin;

para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman'S the Pharmacological Basis of Therapeutics 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can also be an agent useful for reducing any potential side effects of compounds of Formulae (I)-(V). For example, the other therapeutic agent can be an antiemetic agent. Examples of useful antiemetic agents include, but are not limited to, metoclopromide, domperidone, prochlorperazine, promethazine, chlorpromazine, trimethobenzamide, odansteron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrochloride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimelidine.

Examples of useful Ca$^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cyclopiatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazine; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbiturates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrigine, phenobarbital, phenytoin, primidone, valproic acid, trimethadione, benzodiazepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as odansteron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of Formulae (I)-(V) or a pharmaceutically acceptable derivative thereof and the other therapeutic agent can act additively or, in one embodiment, synergistically. In one embodiment, a compound of Formulae (I)-(V) or a pharmaceutically acceptable derivative thereof is administered concurrently with another therapeutic agent; for example, a composition comprising an effective amount of a compound of Formulae (I)-(V) or a pharmaceutically acceptable derivative thereof and an effective amount of another therapeutic agent can be administered. Alternatively, a composition comprising an effective amount of a compound of Formulae (I)-(V) or a pharmaceutically acceptable derivative thereof and a different composition comprising an effective amount of another therapeutic agent can be concurrently administered. In another embodiment, an effective amount of a compound of Formulae (I)-(V) or a pharmaceutically acceptable derivative thereof is administered prior or subsequent to administration of an effective amount of another therapeutic agent. In this embodiment, the compound of Formulae (I)-(V) or a pharmaceutically acceptable derivative thereof is administered while the other therapeutic agent exerts its therapeutic effect, or the other therapeutic agent is administered while the compound of Formulae (I)-(V) or a pharmaceutically acceptable derivative thereof exerts its therapeutic effect for treating or preventing a Condition.

A composition of the invention is prepared by a method comprising admixing a compound of Formulae (I)-(V) or a pharmaceutically acceptable derivative and a pharmaceutically acceptable carrier or excipient. Admixing can be accomplished using methods known for admixing a compound (or salt) and a pharmaceutically acceptable carrier or excipient. In one embodiment the compound of Formulae (I)-(V) or a pharmaceutically acceptable derivative thereof is present in the composition in an effective amount.

Kits

The invention encompasses kits that can simplify the administration of a compound of Formulae (I)-(V) to an animal.

A typical kit of the invention comprises a unit dosage form of a compound of Formulae (I)-(V). In one embodiment, the unit dosage form is a container, which can be sterile, containing an effective amount of a compound of Formulae (I)-(V) or a pharmaceutically acceptable derivative thereof and a pharmaceutically acceptable carrier or excipient. The kit can further comprise a label or printed instructions instructing the use of the compound of Formulae (I)-(V) or a pharmaceutically acceptable derivative thereof to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a compound of Formulae (I)-(V) or a pharmaceutically acceptable derivative thereof, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in Formulation or minor changes in experimental design, are to be considered to fall within the scope of the invention incorporated herein.

In Vivo Assays for Prevention or Treatment of Pain

Test Animals: Each experiment uses rats weighing between 200-260 g at the start of the experiment. The rats are group-housed and have free access to food and water at all times, except prior to oral administration of a compound of Formulae (I)-(V) or a pharmaceutically acceptable derivative thereof, when food is removed for 16 hours before dosing. A control group acts as a comparison to rats treated with a compound of Formulae (I)-(V) or a pharmaceutically acceptable derivative thereof. The control group is administered the carrier for the compound of Formulae (I)-(V). The volume of carrier administered to the control group is the same as the volume of carrier and compound of Formulae (I)-(V) administered to the test group.

Acute Pain: To assess the actions of the compounds of Formulae (I)-(V) for the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of Formulae (I)-(V). Data are expressed as tail flick latency(s) and the percentage of the maximal possible effect (% MPE), i.e., 20 seconds, is calculated as follows:

$$\% \; MPE = \frac{[(\text{post administration latency}) - (\text{pre-administration latency})]}{(20 \; \text{s pre-administration latency})} \times 100$$

The rat tail flick test is described in F. E. D'Amour et al., "A Method for Determining Loss of Pain Sensation," *J. Pharmacol. Exp. Ther.*, 72:74-79 (1941).

Acute pain can also be assessed by measuring the animal's response to noxious mechanical stimuli by determining the paw withdrawal threshold ("PWT"), as described below.

Inflammatory Pain: To assess the actions of the compounds of Formulae (I)-(V) for the treatment or prevention of inflammatory pain the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-*

*Schmiedeberg's Archives of Pharmacol.*, 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/Kg of either a compound of Formulae (I)-(V); 30 mg/Kg of a control selected from Celebrex, indomethacin or naproxen; or carrier. Responses to noxious mechanical stimuli are then determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of the compounds of Formulae (I)-(V) for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain*, 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formulae (I)-(V) for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Binding of Compounds of Formulae (I)-(V) to TRPV1

Methods for assaying compounds capable of inhibiting TRPV1 are known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al. The results of these assays will demonstrate that compounds of Formulae (I)-(V) bind to and modulate the activity of TRPV1.

Biological Assays

For this Protocol, a Chinese Hamster Ovary cell line (CHO) that constitutively expresses human TRPV1 is used (TRPV1/CHO cells). The sequence of the cDNA encoding TRPV1 is available at GenBank accession number AJ277028.

Cell Culture

Cell Culture Media
1. Alpha-MEM (Gibco, CAT: 12561-056, LOT: 1285752): 450 mL
2. Fatal Bovine Serum, heat inactivated (Gibco, CAT: 16140-071, LOT: 1276457): 50 mL
3. HEPES Buffer Solution, 1 M stock (Gibco, CAT: 15630-080): 10 mL (final 20 mM)
4. Geneticin, 50 mg/ml stock (Gibco, CAT: 10135-035): 10 mL (final 1 mg/mL)
5. Antimicotic Antibiotic Mixed Solution, 100× stock (Nacalai Tesque, Japan, CAT: 02892-54): 5 mL Components 1-5 above are combined at the indicated amounts and stored at 4° C. The cell culture media are brought to ~37° C. before use. Optionally, component 5 can be replaced by penicillin-streptomycin solution (for example, Gibco 15140-122 or Sigma P-0781).

Thawing the Cells

TRPV1/CHO cells are frozen in Cellbanker™ (Juji-Field INC, Japan, CAT: BLC-1) and stored at −80° C. Optimized cryopreservation solution containing dimethyl sulphoxide and fetal bovine serum (FBS) is used.

Vials containing the TRPV1/CHO cells are stored at −80° C. After removal from −80° C., the vial is immediately transferred to a 37° C. water bath to thaw for ca. 1-2 minutes. Once completely thawed, the contents of the vial (1 mL/vial) is transferred to a sterile 15 mL test tube and 9 mL warm culture media are slowly added. The test tube is subsequently centrifuged at 1000 rpm for 4 min at room temperature. The supernatant is removed and the pellet resuspended in 10 mL of culture media. The cell suspension is transferred to a sterile 75 cm$^2$ plastic flask and incubated at humidified 5% $CO_2$/95% air at 37° C. To monitor viability, the cells are visually inspected and/or counted, beginning at approximately 1 hr after incubation.

Passaging the Cells

The cells in a flask should be close to confluence at the time of passaging. Cell culture media are removed from the culture flask and 10 mL of sterile PBS(−) added and the flask gently shaken. The PBS is removed from the flask and 2 mL of trypsin/EDTA solution (0.05% trypsin with EDTA-4Na; Gibco, CAT: 25300-054) is added and the flask gently shaken. The flask is incubated at 37° C. for ~2 min. 8 mL cell culture media are subsequently added to the flask and the flask shaken to ensure that all cells are in solution. The cell suspension is then transferred to a sterile 15 mL or 50 mL plastic tube, centrifuged at 1,000 rpm for 4 min at room temperature. The supernatant is removed and the pellet resuspended in ca. 5 mL of culture media. The cell count is measured using the Burker-Turk hemocytometer.

The cells are seeded into a sterile 75 cm$^2$ plastic flask in ca. 0.8×10$^5$ cells/ml for 72 hr and incubated in humidified 5% $CO_2$/95% air at 37° C.

Freezing the Cells

The procedure up to the measurement of the cell count is the same as in the section Passaging the Cells above. Subsequently, the cell suspension is centrifuged at 1,000 rpm for 4 min at room temperature. The supernatant is removed and the pellet resuspended in Cellbanker™ solution to get a final concentration of 5×10$^5$~5×10$^6$ cells/ml. The cell suspension is transferred into appropriately labeled 1 mL cryovials and then placed into the −80° C. freezer.

pH-Based Assay:

The following assay is conducted to determine the concentration of sulfuric acid that would give rise to a pH that induces a $Ca^{2+}$ response optimal to test compounds for their effect on TRPV1.

1. Cells

TRPV1/CHO cells are seeded in the 96-well clear-bottom black-wall plate (Nunc) at densities of 1-2×10$^4$ cells/well and grown in 100 μL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Different agonist solutions with sulfuric acid concentrations ranging from 15 mM to 18 mM are prepared by diluting 1M sulfuric acid with measuring buffer. The different sulfuric acid concentrations in the agonist solutions are selected such that a 1:4 dilution would result in a final sulfuric acid concentration of between 3.0 mM to 3.6 mM, respectively.

2.2. Assay pH dependent $Ca^{2+}$ responses in TRPV-1/CHO cells cultured in a 96-well plate are observed. In particular, $Ca^{2+}$ influx into TRPV-1/CHO cells in response to low pH as measured by Fura-2 AM fluorescence is observed. The cells are stimulated using 3.0 mM (well number B1-6), 3.1 mM (C1-6), 3.2 mM (D1-6), 3.3 mM (E1-6), 3.4 mM (F1-6), 3.5 mM (G1-6), or 3.6 mM (H1-6) $H_2SO_4$ or pH 7.2 measuring buffer without $H_2SO_4$ (A1-6).

(1) Culture medium is removed using an 8-channel-pipette (Rainin, USA) from the 96-well plate and the wells are refilled with 100 μL of loading buffer (20 mM HEPES, 115 mM NaCl, 5.4 mM KCl, 0.8 mM MgCl2, 1.8 mM CaCl2, 13.8 mM D-glucose, 2.5 mM probenecid, pH 7.4) containing 5 μM Fura-2 AM (Dojin, Japan).

(2) The 96-well plate is incubated at 37° C. for 45 min.

(3) The loading buffer is removed from each well. The cells are subsequently washed twice with 150 μL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells are then refilled with 80 μL of measuring buffer.

(4) After an incubation at 4° C. for 15 min, the 96-well plate is transferred to FDSS-3000 (Hamamatsu photonics, Japan).

(5) The Fura-2 fluorescent intensity is monitored at a wavelength of 340 nm and at 380 nm, respectively, at a rate of 0.5 Hz for a total of 240 seconds. After 16 time points (32 sec) of baseline detection, 20 μL of agonist solution is added to each well. The final volume should be 100 μL/well.

(6) Fluorescence intensity ratio refers to the fluorescence intensity at 340 nm over the fluorescence intensity at 380 nm at a particular time point. The baseline is set as the average of the fluorescent intensity ratios for the first 16 time points before the addition of agonist solution. The maximum response is the highest fluorescent intensity ratio during the 60 time points following addition of agonist solution.

(7) Maximal signal ratios from each well are calculated as output data using the FDSS-3000 analysis program. Data are analyzed using Excel (Microsoft) and XLfit (idbs) software.

2.3. pH Determination

After the observation of $Ca^{2+}$ responses, the buffer of each lane (50 μL/well, 8-20 wells/plate) is collected well by well and the pH values are measured using a portable pH meter (Shindengen, Japan).

Lanes optimal for testing the effects of compounds on the TRPV1 calcium channel are selected. The final sulfuric acid concentrations in the wells of these lanes are 3.2 mM and 3.3 mM, respectively. These final sulfuric acid concentrations are obtained using agonist solutions with 16.0 mM and 16.5 mM sulfuric acid concentrations, respectively. The pH obtained using these sulfuric acid concentrations is ca. 5.0-5.1.

Thus, agonist solutions with 16.0 mM and 16.5 mM sulfuric acid concentrations, respectively, are selected for the experiments described below in section 3.

3. pH Assay 3.1. Agonist

Two different agonist solutions with different $H_2SO_4$ concentrations are used for the pH assay. For one half of a 96-well plate one agonist solution is used, for the other half the other agonist solution. The agonist solutions are obtained by diluting sulfuric acid ($H_2SO_4$, 1M) with measuring buffer. The concentrations for the two agonist solutions are determined as described above in Section 2 of this Protocol.

The sulfuric acid concentrations between the two agonist solutions differed by 0.5 mM. In the experiment described in Section 2 of this Protocol, the sulfuric acid concentrations in the agonist solutions are determined to be 16 mM and 16.5 mM, respectively. After 1:4 dilution of the agonist solutions, the final sulfuric acid concentration is 3.2 mM and 3.3 mM, respectively. The resulting pH value for the pH assay is 5.0 to 5.1.

3.2. Test Compounds

Test compounds are dissolved in DMSO to yield 1 mM stock solutions. The stock solutions are further diluted using DMSO in 1:3 serial dilution steps with 6 points (1000 µM, 250 µM, 62.5 µM, 15.625 µM, 3.9062 µM and 0.977 µM). The thereby obtained solutions are further diluted in measuring buffer (1:100) as 10× stock serial dilutions with a DMSO concentration of 1%. 10 µL of a 10× stock is added into each well at step 3.3.(4) of this Protocol. Thus, the final concentrations of antagonists ranged from 1000-0.977 nM containing 0.1% DMSO.

3.3. Assay

Steps (1) and (2) are the same as steps 2.2.(1) and 2.2.(2) of this Protocol, respectively.

(3) The cells are washed twice with 150 µL of measuring buffer (mentioned in 2.2.(3) of this Protocol, no probenecid). The wells are subsequently refilled with 70 µL of measuring buffer.

(4) Either 10 µL of measuring buffer or 10 µL of 10× stock serial dilution of antagonist (described in 3.2. of this Protocol) are applied to each well. Usually, only one antagonist is tested per 96-well plate. The number of replicates per 96-well plate for a particular antagonist at a particular concentration is 7×2 since two different sulfuric acid concentrations are used per 96-well plate (N=7×2).

Step (5) is the same as 2.2.(4) in this Protocol.

(6) Fura-2 fluorescent intensity is monitored as described in 2.2.(5) of this Protocol. After 16 time points of baseline detection, 20 µL of agonist solution (measuring buffer titrated with $H_2SO_4$ to yield pH 5.0-5.1 when mixed 1:4 with the measuring buffer containing antagonists) is added to each well (final volume is 100 µL/well).

Steps (7) and (8) are as described in 2.2.(6) and 2.2.(7) of this Protocol, respectively.

3.4 pH Check (1) The pH values of the buffer in the wells of A1→H1 and A7→H7 are measured one by one using a portable pH meter.

(2) When a well is confirmed as pH 5.0 or 5.1, the next five wells to its right are checked one after another. The pH values after this assay tend to be equal between neighboring wells in a row.

(3) 6-12 additional wells per 96-well plate are randomly selected and checked again. However, few wells that are next to a well with an unsuitable pH in one row tend to show a proper pH.

(4) For $IC_{50}$ calculation, only the data from wells with pH values of 5.0-5.1 are used.

The number of wells tested for their pH varied among plates (about 16-60 wells/plate). The number depended on the results of 3.4.(1) of this Protocol and the $Ca^{2+}$ responses. When there are few wells measured as pH 5.0-5.1 in 3.4.(1) of this Protocol or the cells in only few wells showed a proper $Ca^{2+}$ responses, only the pH in a small number of wells is checked (<about 20 wells/plate) and the pH assay is repeated.

Capsaicin-Based Assay:

One day prior to assay, TRPV1/CHO cells are seeded in 96-well clear-bottom black plates (20,000 cells/well) in growth media. On the day of the experiment, the cells are washed with 0.2 ml 1× Hank's Balanced Salt Solution (Life Technologies) containing 1.6 mM $CaCl_2$ and 20 mM HEPES, pH 7.4 ("wash buffer"). Subsequently, the cells are loaded by incubation in 0.1 ml of wash buffer containing Fluo-4 at 3 µM final concentration. After 1 hour, the cells are washed twice with 0.2 ml wash buffer and resuspended in 0.1 ml wash buffer. The plates are then transferred to a Fluorescence Imaging Plate Reader (Molecular Devices). Fluorescence intensity is monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO are added to the cell plate and fluorescence is monitored for 2 minutes. The final concentration of the compound is adjusted to range from 100 µM to 1.5625 µM. If the antagonist is especially potent, the final concentration of the compound is adjusted to range from 10 µM to 156.25 nM. Human TRPV1 is then activated by the addition of 50 µL capsaicin (100 nM final concentration) and plates incubated for an additional 3 min. Data are collected over the entire time course and analyzed using Excel and the curve-fitting Formula GraphPad Prism.

The results of the pH-based assay and the capsaicin-based assay demonstrate that the test compounds of Formulae (I)-(V) bind to and modulate the activity of human TRPV1.

TABLE 20

Potency ($IC_{50}$(nM)) and Solubility (µM) of Diol Compounds

| | Potency, $IC_{50}$(nM) | | Solubility (µM) | |
|---|---|---|---|---|
| Compound | Capsaicin assay | pH assay | pH: 1.2 | pH: 6.8 |
| A14 | 23.8 ± 6.2 | 9.5 ± 2.5 | >50 | 19 |
| B14 | 29.4 ± 6.3 | 14.7 ± 1.01 | | |
| I5 | 35.6 ± 5.1 | | 46 | 1 |
| E2 | 45.9 ± 4.2 | | >50 | 25 |
| F2 | 108.6 ± 25.5 | | >50 | 21 |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:
1. A compound of Formula (I):

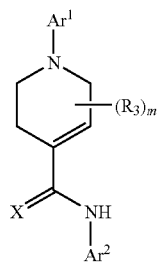
(I)

or a stereoisomer, or a pharmaceutically acceptable salt thereof, wherein:

$Ar^1$ is

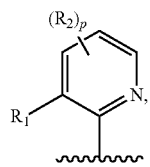
(iv)

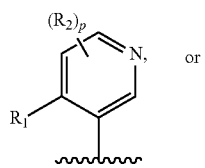
(v)

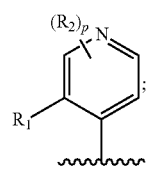
(vi)

$Ar^2$ is

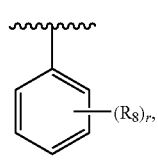
(a)

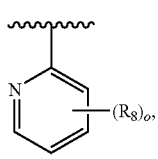
(b)

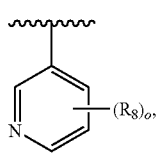
(c)

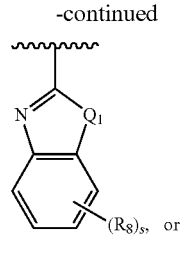
(e)

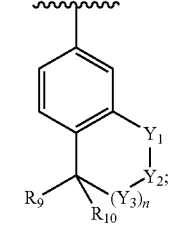
(f)

X is O or S;

$Q_1$ is O, S, or NH;

$R_1$ is hydrogen, halo, $(C_1-C_4)$alkyl, nitro, cyano, hydroxy, methoxy, amino, trihalomethyl, dihalomethyl, halomethyl, OC(halo)$_3$, OCH(halo)$_2$, or OCH$_2$(halo);

each $R_2$ is an alkyl group substituted with two hydroxy groups;

each of $Y_1$, $Y_2$, and $Y_3$ is C or NR', provided that at least one of $Y_1$, $Y_2$, and $Y_3$ is CR', wherein R' is H or $(C_1-C_6)$alkyl;

each $R_3$ is independently
(a) hydrogen, —CH$_2$OR$_7$, or $(C_1-C_6)$alkyl;
(b) two $R_3$ groups together form a $(C_2-C_6)$bridge, which is unsubstituted or substituted with 1, 2 or 3 independently selected $R_8$ groups, and which bridge optionally contains —HC═CH— within the $(C_2-C_6)$ bridge; or
(c) two $R_3$ groups together form a —CH$_2$—N(R$_a$)—CH$_2$— bridge, a

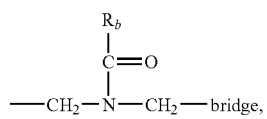

or a

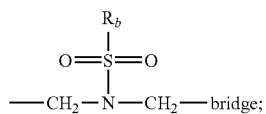

$R_a$ is —H, $(C_1-C_6)$alkyl, $(C_3-C_8)$cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;

each $R_b$ is independently:
(a) —H, $(C_1-C_6)$alkyl, $(C_3-C_8)$cycloalkyl, -(3- to 7-membered)heterocycle, —N(R$_c$)$_2$, —N(R$_c$)—(C$_3$-C$_8$)cycloalkyl, or —N(R$_c$)-(3- to 7-membered)heterocycle; or
(b) phenyl, (5- or 6-membered)heteroaryl, —N(R$_c$)-phenyl, or —N(R$_c$)-(5- to 10-membered)heteroaryl, each of which is unsubstituted or substituted with 1, 2 or 3 independently selected $R_7$ groups;

each $R_c$ is independently —H or $(C_1-C_4)$alkyl;

each $R_8$ is independently (a) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups, or (b) H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, O—CN, CN, OH, halo, $N_3$, $NO_2$, $CH=NR_7$, $N(R_7)_2$, $NR_7OH$, $OR_7$, $C(O)R_7$, $C(O)OR_7$, $OC(O)R_7$, $OC(O)OR_7$, $SR_7$, $S(O)R_7$, $S(O)_2R_7$ or $SO_2CH_2(halo)O(C_1-C_6)$alkyl;

$R_7$ is H, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyalkyl, $(C_1-C_6)$alkoxy$(C_1-C_6)$alkyl, $(C_1-C_6)$alkyl-$N(R_{20})_2$, or $CON(R_{20})_2$;

each of $R_9$ and $R_{10}$ is independently hydrogen or $(C_1-C_6)$alkyl; or together with the carbon atom to which they are attached form a $C_3-C_6$ carbocycle;

$R_{20}$ is H, $(C_1-C_4)$alkyl, halo$(C_1-C_4)$alkyl, hydroxy$(C_1-C_4)$alkyl, or $(C_1-C_4)$alkoxy$(C_1-C_4)$alkyl;

each n is 0, 1, or 2;

each of m, o, and s is independently 0, 1, 2, 3, or 4;

p is 1, 2, or 3; and each of q and r is independently 0, 1, 2, 3, 4, or 5.

2. The compound according to claim 1, wherein X is O.

3. The compound according to claim 1, wherein o, r or s is 1.

4. The compound according to claim 1, wherein o, r or s is 2.

5. The compound according to claim 1, wherein o, r or s is 0.

6. The compound according to claim 1, wherein m is 0.

7. The compound according to claim 1, wherein $Ar^2$ is:

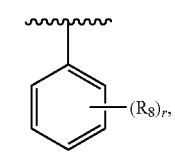
(a)

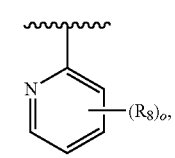
(b)

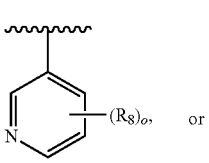
(c)

or

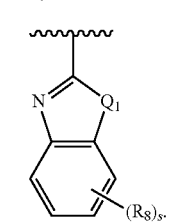
(e)

8. The compound according to claim 7, wherein $Ar^2$ is

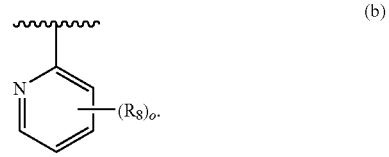
(b)

9. The compound according to claim 7, wherein $Ar^2$ is

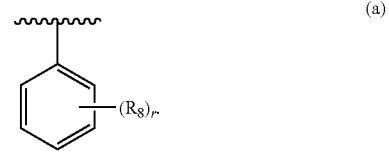
(a)

10. The compound according to claim 7, wherein $Ar^2$ is

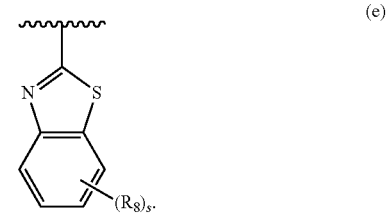
(e)

11. The compound according to claim 7, wherein $Ar^2$ is

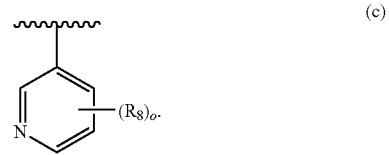
(c)

12. The compound according to claim 1, wherein $R_2$ is:

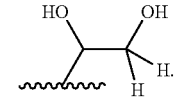

13. The compound according to claim 12, wherein $R_2$ is:

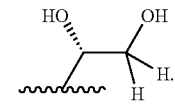

14. The compound according to claim 12, wherein $R_2$ is:

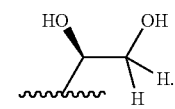

15. The compound according to claim 12, wherein the enantiomeric excess of either the (S)-enantiomer or the (R)-enantiomer or a pharmaceutically acceptable salt thereof is greater than 50%, 60%, 70%, 80%, 90%, 95%, or 99%.

16. The compound according to claim 1, wherein $R_1$ is H, halo, $(C_1-C_4)$alkyl, nitro, CN, OH, $OCH_3$, $NH_2$, trihalomethyl, dihalomethyl, or halomethyl.

17. The compound according to claim 16, wherein $R_1$ is halo, methyl or trifluoromethyl.

18. The compound according to claim 17, wherein $R_1$ is $CF_3$, F, or Cl.

19. The compound according to claim 1, wherein each $R_8$ is independently selected from the group consisting of H, halo, $(C_1-C_6)$alkyl, $C(halo)_3$, $CH(halo)_2$, $CH_2(halo)$, $OC(halo)_3$, $OCH(halo)_2$, $OCH_2(halo)$, $OR_7$, $SO_2C(halo)_3$, $SO_2CH(halo)_2$, $SO_2CH_2(halo)$, $SO_2CH_2(halo)O(C_1-C_6)$alkyl, $SC(halo)_3$, and $CH_2OH$.

20. The compound according to claim 19, wherein each $R_8$ is independently selected from the group consisting of $C(halo)_3$, $OC(halo)_3$, halo, and $OR_7$.

21. The compound according to claim 19, wherein each $R_3$ is independently selected from the group consisting of $CF_3$, $OCF_3$, F, $CH_3$, $OCH_3$, $OCH_2CH_3$, $C(CH_3)_3$, Br, Cl, and $SO_2CF_3$.

22. The compound according to claim 21, wherein each $R_8$ is independently selected from the group consisting of $CF_3$, $OCF_3$, and F.

23. A pharmaceutical composition, comprising a compound according to claim 1 or a stereoisomer, or a pharmaceutically acceptable salt thereof and a pharmaceutically acceptable carrier or excipient.

24. A method for inhibiting TRPV1 function in a cell, comprising contacting a cell capable of expressing TRPV1 with an effective amount of the compound or a stereoisomer, or a pharmaceutically acceptable salt of the compound of claim 1.

25. The compound having Formula (IV):

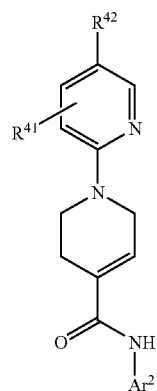

(IV)

or a stereoisomer, or a pharmaceutically acceptable salt thereof, wherein:
$Ar^2$ is

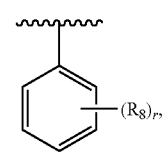

(a)

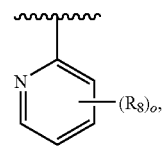

(b)

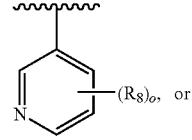

(c)

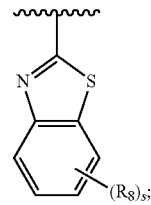

(e)

$R^{41}$ is hydrogen, halo, methyl, trihalomethyl, dihalomethyl, or halomethyl;

$R^{42}$ is

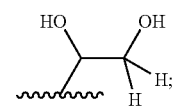

each $R_8$ is independently hydrogen, halo, $(C_1-C_6)$alkyl, $C(halo)_3$, $CH(halo)_2$, $CH_2(halo)$, $OC(halo)_3$, $OCH(halo)_2$, $OCH_2(halo)$, $OR_7$, $SC(halo)_3$, $SO_2C(halo)_3$, or $SO_2CH(halo)_2$; and each of o, r, and s is 1 or 2.

26. The compound according to claim 25, wherein $R^{41}$ is halo, methyl, or trifluoromethyl.

27. The compound according to claim 26, wherein $R^{41}$ is $CF_3$, F, or Cl.

28. The compound having Formula (V):

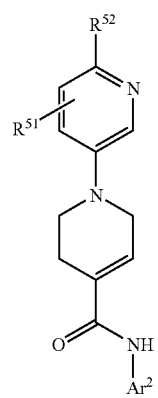

(V)

or a stereoisomer, or a pharmaceutically acceptable salt thereof, wherein:

Ar² is (a) 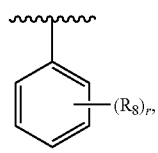

(b) 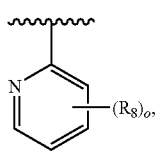

(c) 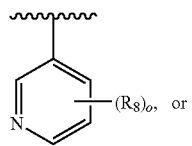, or

-continued (e) 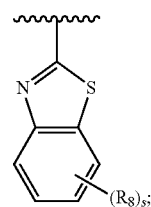

$R^{51}$ is hydrogen, halo, methyl, trihalomethyl, dihalomethyl, or halomethyl;

$R^{52}$ is

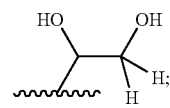

each $R_8$ is independently hydrogen, halo, $(C_1-C_6)$alkyl, $C(halo)_3$, $CH(halo)_2$, $CH_2(halo)$, $OC(halo)_3$, $OCH(halo)_2$, $OCH_2(halo)$, $OR_7$, $SC(halo)_3$, $SO_2C(halo)_3$, or $SO_2CH(halo)_2$; and each of o, r, and s is 1 or 2.

29. The compound according to claim 28, wherein $R^{51}$ is halo, methyl, or trifluoromethyl.

30. The compound according to claim 29, wherein $R^{51}$ is $CF_3$, F, or Cl.

* * * * *